United States Patent
Topczewski et al.

(10) Patent No.: US 10,941,153 B2
(45) Date of Patent: Mar. 9, 2021

(54) SUBSTITUTED PHENETHYLAMINE DERIVATIVES

(71) Applicant: REGENTS OF THE UNIVERSITY OF MINNESOTA, Minneapolis, MN (US)

(72) Inventors: Joseph John Topczewski, Minneapolis, MN (US); Matthew Ryan Porter, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 16/428,343

(22) Filed: May 31, 2019

(65) Prior Publication Data
US 2019/0367527 A1    Dec. 5, 2019

Related U.S. Application Data

(60) Provisional application No. 62/678,820, filed on May 31, 2018.

(51) Int. Cl.
| | |
|---|---|
| *C07D 491/052* | (2006.01) |
| *C07D 471/04* | (2006.01) |
| *C07C 217/54* | (2006.01) |
| *C07D 311/74* | (2006.01) |
| *C07D 311/92* | (2006.01) |
| *C07D 215/38* | (2006.01) |

(52) U.S. Cl.
CPC ........ *C07D 491/052* (2013.01); *C07C 217/54* (2013.01); *C07D 215/38* (2013.01); *C07D 311/74* (2013.01); *C07D 311/92* (2013.01); *C07D 471/04* (2013.01)

(58) Field of Classification Search
CPC .......................... C07D 491/052; C07D 215/38; C07D 311/74; C07C 217/54
USPC ....................................................... 546/173
See application file for complete search history.

(56) References Cited

U.S. PATENT DOCUMENTS 6,583,166 B1 * 6/2003 Starck .................... A61P 25/36
                                                                514/384

FOREIGN PATENT DOCUMENTS

| WO | WO-9220655 A1 * | 11/1992 | ........... C07D 221/10 |
| WO | WO-9631512 A1 * | 10/1996 | ........... C07D 491/04 |

OTHER PUBLICATIONS

Matthew Porter et al 3=Amino-chromanes and Tetrahydroquinolines as Selective 5HT2B, 5-HT7, or σ1 receptor Ligands. (Year: 2019).*

* cited by examiner

*Primary Examiner* — Rita J Desai
(74) *Attorney, Agent, or Firm* — Billion & Armitage

(57) ABSTRACT

Embodiments of the present disclosure describe substituted phenethylamine derivatives, compositions comprising the substituted phenethylamine derivatives, methods of making the substituted phenethylamine derivatives, and methods of using the phenethylamine derivatives, and the like. Exemplary compounds of the present disclosure include compounds of the formula (I) and (II):

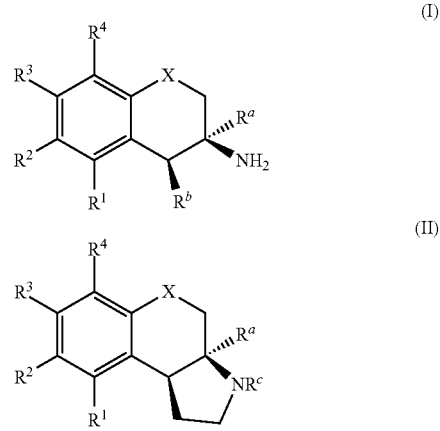

wherein X, $R^a$, $R^b$, $R^c$, $R^1$, $R^2$, $R^3$, and $R^4$ are defined elsewhere.

11 Claims, 29 Drawing Sheets a. Endogenous Phenethylamine GCPR Ligands b. Common Phenethylamine GCPR Ligands a. Prior Work b. This Work ■ >20 Compounds ■ Low nM Affinity ■ New 5-HT₇, and σ₁ Lead

Table A: Optimization of Tandem Rearrangement Friedel-Crafts Alkylation

| entry[a] | catalyst | yield %[b] | dr[c] |
|---|---|---|---|
| 1 | BF$_3$·OEt$_2$ | 35 | 28:1 |
| 2 | Cu(OTf)$_2$ | 75 | 9:1 |
| 3 | Zn(OTf)$_2$ | 58 | 9:1 |
| 4 | TFA | 4 | 4:1 |
| 5 | TsOH | 4 | 7:1 |
| 6 | Tf$_2$NH | 80 | 13:1 |
| 7 | TfOH | 49 | 7:1 |
| 8 | PdCl$_2$ | 0 | nd |
| 9 | [(COP)PdCl]$_2$ | 0 | nd |
| 10 | JohnPhosAuSbF$_6$ | 75 | 21:1 |
| 11 | AgOTs | 0 | nd |
| 12 | AgClO$_4$ | 81 | 7:1 |
| 13 | AgOTf | 80 | 7:1 |
| 14 | AgSbF$_6$ | 92 | 21:1 |
| 15[d] | AgSbF$_6$ | 3 | 3:1 |
| 16[e] | AgSbF$_6$ | 55 | 16:1 |
| 17[f] | AgSbF$_6$ | 71 | 21:1 |
| 18[g] | AgSbF$_6$ | 77 | 20:1 |

Table 1. Initial GCPR Screen

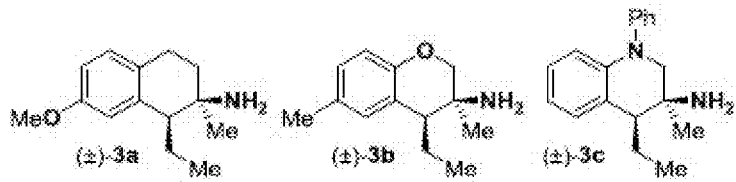

(±)-3a, (±)-3b, (±)-3c

| Receptor | $K_i$ (nM)[a] | | |
|---|---|---|---|
| | Compound 3a | Compound 3b | Compound 3c |
| 5-HT$_{1A}$ | 650 | 2,100 | <u>74</u> |
| 5-HT$_{1B}$ | >10,000 | >10,000 | >10,000 |
| 5-HT$_{1D}$ | >10,000 | >10,000 | >10,000 |
| 5-HT$_{1E}$ | >10,000 | >10,000 | >10,000 |
| 5-HT$_{2A}$ | >10,000 | >10,000 | >10,000 |
| 5-HT$_{2B}$ | <u>150</u> | <u>180</u> | 850 |
| 5-HT$_{2C}$ | 2,200 | 2,400 | 3,900 |
| 5-HT$_3$ | >10,000 | >10,000 | >10,000 |
| 5-HT$_6$ | >10,000 | >10,000 | >10,000 |
| 5-HT$_7$ | >10,000 | >10,000 | 1,100 |
| Alpha$_{1A}$ | >10,000 | >10,000 | 1,500 |
| Alpha$_{1B}$ | >10,000 | >10,000 | >10,000 |
| Alpha$_{1D}$ | >10,000 | >10,000 | >10,000 |
| Alpha$_{2A}$ | 6,600 | >10,000 | 380 |
| Alpha$_{2B}$ | 5,500 | >10,000 | 420 |
| Alpha$_{2C}$ | >10,000 | >10,000 | >10,000 |
| Beta$_1$ | >10,000 | >10,000 | >10,000 |
| Beta$_2$ | 5,300 | >10,000 | >10,000 |
| Beta$_3$ | >10,000 | >10,000 | 1,000 |
| BZP | 1,500 | >10,000 | 8,400 |
| D$_1$ | >10,000 | >10,000 | >10,000 |
| D$_2$ | >10,000 | >10,000 | >10,000 |
| D$_3$ | >10,000 | >10,000 | >10,000 |
| D$_4$ | >10,000 | >10,000 | 2,100 |
| D$_5$ | >10,000 | >10,000 | >10,000 |
| DAT | 5,300 | >10,000 | 3,200 |
| GABA$_A$ | >10,000 | >10,000 | >10,000 |
| H$_1$ | 3,900 | >10,000 | >10,000 |
| H$_2$ | >10,000 | >10,000 | >10,000 |
| H$_3$ | >10,000 | >10,000 | 3,800 |
| H$_4$ | >10,000 | >10,000 | >10,000 |
| M$_1$ | >10,000 | >10,000 | >10,000 |
| M$_2$ | >10,000 | >10,000 | >10,000 |
| M$_3$ | >10,000 | >10,000 | >10,000 |
| M$_4$ | >10,000 | >10,000 | >10,000 |
| M$_5$ | >10,000 | >10,000 | >10,000 |
| NET | 2,500 | 330 | 370 |
| δ-OR | >10,000 | >10,000 | >10,000 |
| κ-OR | <u>300</u> | >10,000 | >10,000 |
| μ-OR | >10,000 | >10,000 | >10,000 |
| PBR | >10,000 | >10,000 | >10,000 |
| σ$_1$ | <u>120</u> | 1,000 | 330 |
| σ$_2$ | >10,000 | >10,000 | 630 |

[a] $K_i$ values represent the average of at least triplicate trials. SEM <±20%.

*FIG. 6*

Table 2. $K_i$ Data for Primary Amino-Chromanes

| Compound | $K_i$ (nM)[a] | | | | |
|---|---|---|---|---|---|
| | 5-HT1A | 5-HT1B | 5-HT7 | σ1 | σ2 |
| (±)-3d | | >10,000 | | >10,000 | >10,000 |
| (±)-3e | 3,200 | 210 | | 350 | >10,000 |
| (±)-3f | 2,700 | 120 | | <u>16</u> | 340 |
| (±)-3g | 2,200 | <u>3.4</u> | 960 | 3,900 | 310 |
| (±)-3h | | <u>20</u> | 760 | 1,300 | 1,900 |

[a] $K_i$ values represent the average of at least triplicate trials. SEM ≤±20%.

FIG. 7

Table 3. $K_i$ Data for Pyrrolidine Containing Chromanes

| Compound | $K_i$ (nM)[a] | | | | |
|---|---|---|---|---|---|
| | 5-HT$_{1A}$ | 5-HT$_{2A}$ | 5-HT$_7$ | $\alpha_1$ | $\alpha_2$ |
| (±)-4a | 270 | 1,100 | 12 | | 120 |
| (±)-4b | 710 | 200 | 110 | | 2,700 |
| (±)-4c | 120 | | | 12 | 130 |
| (±)-4d | >10,000 | | >10,000 | | 1,200 |
| (±)-10a | 1,200 | | | 65 | 3,800 |
| (±)-11a | >10,000 | | >10,000 | | >10,000 |
| (±)-4e | 960 | 230 | 1,100 | 44 | >10,000 |
| (±)-4f | 2,300 | 77 | 1,100 | 63 | 430 |
| (±)-4g | 200 | 170 | 23 | 39 | 120 |
| (±)-10b | 270 | 410 | 24 | 66 | 290 |
| (±)-11b | | 530 | | >10,000 | 1,300 |
| (±)-4h | 1,200 | 23 | 390 | 500 | 700 |

[a] $K_i$ values represent the average of at least triplicate trials. SEM <±20%.

*FIG. 8*

Table 5. Broad GCPR Screen

| Receptor | Compound 4e | Compound 4i |
|---|---|---|
| 5-HT$_{1B}$ | >10,000 | >10,000 |
| 5-HT$_{1D}$ | >10,000 | >10,000 |
| 5-HT$_{1E}$ | >10,000 | >10,000 |
| 5-HT$_{2C}$ | 1400 | >10,000 |
| 5-HT$_3$ | >10,000 | >10,000 |
| 5-HT$_6$ | >10,000 | >10,000 |
| Alpha$_{1A}$ | >10,000 | >10,000 |
| Alpha$_{1B}$ | >10,000 | >10,000 |
| Alpha$_{1D}$ | >10,000 | 1,000 |
| Alpha$_{2B}$ | >10,000 | >10,000 |
| Alpha$_{2C}$ | >10,000 | 970 |
| Beta$_1$ | 940 | 3,300 |
| Beta$_2$ | 580 | >10,000 |
| Beta$_3$ | >10,000 | >10,000 |
| BZP | 6,700 | >10,000 |
| D$_1$ | >10,000 | >10,000 |
| D$_2$ | >10,000 | >10,000 |
| D$_3$ | >10,000 | >10,000 |
| D$_4$ | >10,000 | >10,000 |
| D$_5$ | >10,000 | >10,000 |
| DAT | >10,000 | >10,000 |
| GABA$_A$ | >10,000 | >10,000 |
| H$_1$ | >10,000 | >10,000 |
| H$_2$ | >10,000 | 1,900 |
| H$_4$ | >10,000 | >10,000 |
| M$_1$ | >10,000 | >10,000 |
| M$_2$ | >10,000 | >10,000 |
| M$_3$ | >10,000 | >10,000 |
| M$_4$ | >10,000 | >10,000 |
| M$_5$ | >10,000 | >10,000 |
| NET | >10,000 | >10,000 |
| δ-OR | >10,000 | >10,000 |
| κ-OR | >10,000 | >10,000 |
| μ-OR | >10,000 | 1,600 |
| PBR | >10,000 | >10,000 |

$^a K_i$ values represent the average of at least triplicate trials. SEM <±20%.

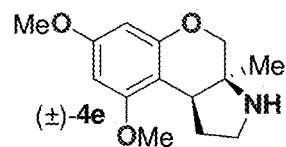
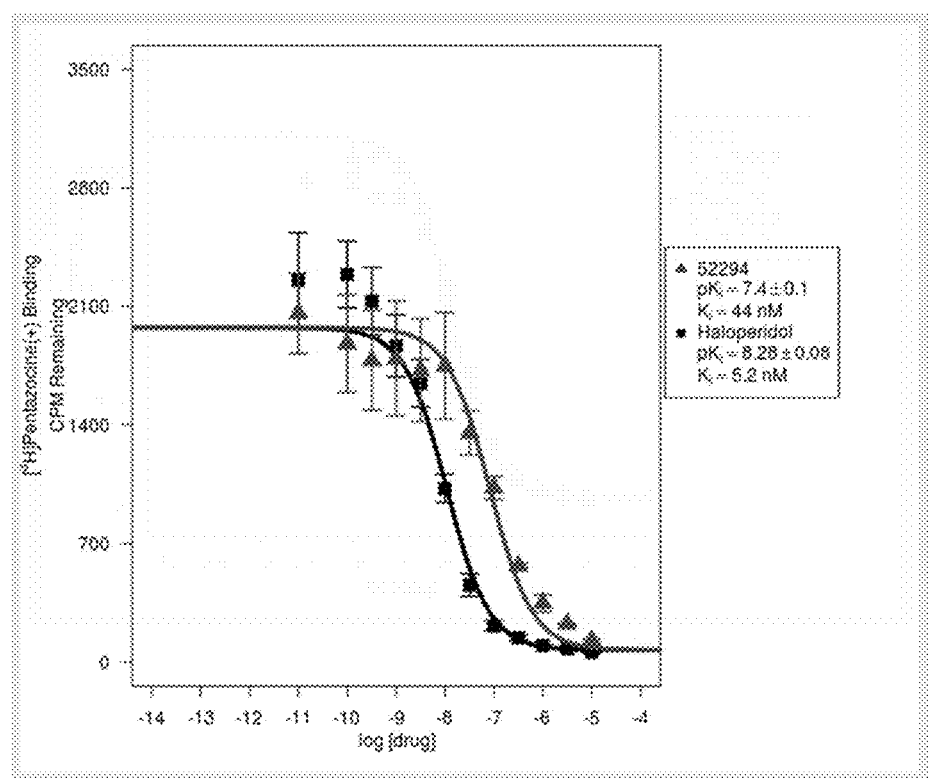
FIG. 11A

| Concentration | 4e | PDSP ID: | 52294 | Concentration | Haloperidol | | |
|---|---|---|---|---|---|---|---|
| -11 | 2529 | 1895 | 1756 | -11 | 2795 | 1851 | 2120 |
| -10 | 2408 | 1418 | 1818 | -10 | 2681 | 2106 | 2079 |
| -9.5 | 2246 | 1227 | 1873 | -9.5 | 2491 | 1803 | 2101 |
| -9 | 2266 | 1131 | 1979 | -9 | 1984 | 1509 | 2111 |
| -8.5 | 2154 | 1134 | 1880 | -8.5 | 1859 | 1378 | 1701 |
| -8 | 2251 | 1166 | 1832 | -8 | 1189 | 935 | 945 |
| -7.5 | 1470 | 1092 | 1491 | -7.5 | 401 | 377 | 586 |
| -7 | 1129 | 901 | 1049 | -7 | 192 | 179 | 272 |
| -6.5 | 564 | 549 | 592 | -6.5 | 120 | 141 | 171 |
| -6 | 432 | 349 | 260 | -6 | 92 | 87 | 115 |
| -5.5 | 221 | 225 | 232 | -5.5 | 57 | 83 | 98 |
| -5 | 134 | 108 | 139 | -5 | 56 | 57 | 61 |

*FIG. 11B*

| Concentration | 4i | PDSP ID: | 52293 | Concentration | Clozapine | | |
|---|---|---|---|---|---|---|---|
| -11 | 1606 | 1814 | 1727 | -11 | 1416 | 1759 | 1583 |
| -10 | 1661 | 1788 | 1914 | -10 | 1801 | 2028 | 1780 |
| -9.5 | 1652 | 1703 | 1662 | -9.5 | 1916 | 1904 | 1859 |
| -9 | 1802 | 1871 | 1806 | -9 | 1585 | 1758 | 1715 |
| -8.5 | 1585 | 1687 | 1589 | -8.5 | 1564 | 1509 | 1408 |
| -8 | 1252 | 1192 | 1074 | -8 | 1248 | 1146 | 1102 |
| -7.5 | 569 | 600 | 715 | -7.5 | 663 | 752 | 803 |
| -7 | 288 | 324 | 317 | -7 | 342 | 364 | 392 |
| -6.5 | 190 | 176 | 156 | -6.5 | 202 | 186 | 184 |
| -6 | 125 | 137 | 121 | -6 | 125 | 93 | 90 |
| -5.5 | 85 | 124 | 71 | -5.5 | 63 | 72 | 84 |
| -5 | 68 | 82 | 72 | -5 | 53 | 59 | 38 |

*FIG. 12B*

Table 6: Results From Pyschoactive Drug Screening Program
$K_i$ (nM) for GPCR
| Lab Book# | PDSP ID | Structure | 5-HT$_{1A}$ Avg | 5-HT$_{2B}$ Avg | 5-HT$_7$ Avg | $\sigma_1$ Avg | $\sigma_2$ Avg | Log P |
|---|---|---|---|---|---|---|---|---|
| (+)-MRP5013 | 53527 | 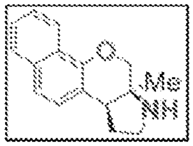 | | | | | 367.01 | 2.59 |
| (-)-MRP5013 | 53528 | 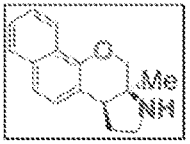 | | 4.6 | | | 198.66 | 2.59 |
| MRP4268 | 53529 | 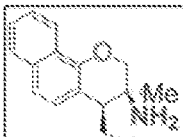 | | 3.4 | | | 506.08 | 3 |
| (+)-MRP5014 | 53530 | 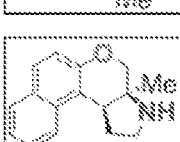 | | 565.9 | | | | 2.59 |
| (-)-MRP5014 | 53531 | 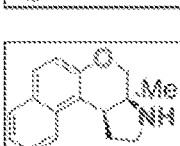 | | 4.5 | | | | 2.59 |
| MRP4269 | 53532 | 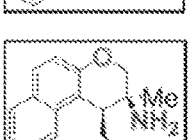 | | 11.3 | | | | 3 |
| (+/-)-MRP3215 | 52294 | 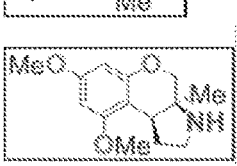 | 960.0 | 227.0 | 1146.0 | 44.0 | >10,000 | 1.34 |
| (-)-MRP5139 | 53533 | 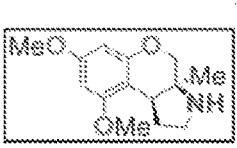 | | 10000.0 | | 10000.0 | | 1.34 |
| (+)-MRP5139 | 53534 | 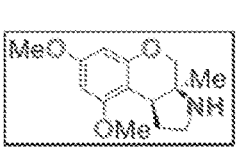 | | 81.6 | | | 10000.0 | 1.34 |
FIG. 13A

| Name | ID | Structure | | | | | | |
|---|---|---|---|---|---|---|---|---|
| (−)-MRP4196 | 53543 | 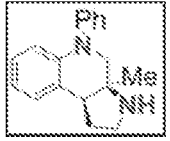 | | 318.0 | | 415.6 | | 3.42 |
| (+)-MRP4196 | 53544 | 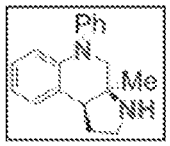 | | 1197.0 | | 344.1 | | 3.42 |
| MRP5022 | 53545 | 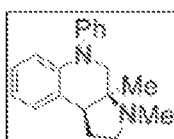 | | 203.9 | | 136.2 | | 3.8 |
| MRP5023 | 53546 | 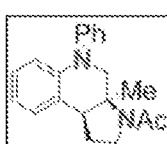 | | 10000.0 | | 10000.0 | | 3.07 |
| MRP3160 | 52290 | 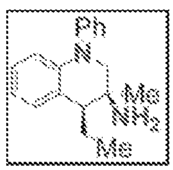 | 74.0 | 850.0 | 1061.0 | 330.0 | 629.0 | 3.83 |
| MRP5056 | 53547 | 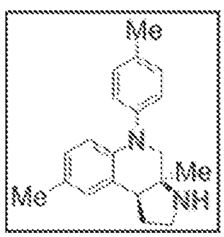 | | 340.8 | | 259.5 | | 4.4 |
| MRP5057 | 53548 | 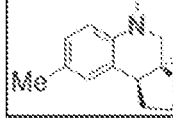 | | 464.9 | | 236.8 | | 5.08 |
| MRP5028 | 53550 | 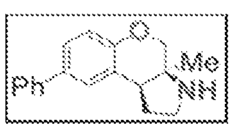 | | 270.0 | | 11.7 | | 3.27 |
| MRP5063 | 53549 | 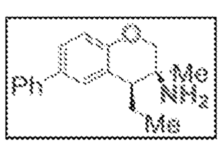 | | 116.7 | | 16.3 | | 3.68 |
FIG. 13C

| ID | # | Structure | | | | | | Ratio |
|---|---|---|---|---|---|---|---|---|
| MRP5069 | 53552 | 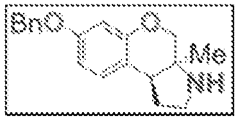 | | 120.1 | | 11.5 | | 3.2 |
| MRP5086 | 53553 | 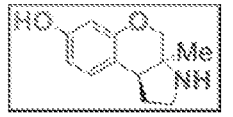 | | 10000.0 | | 10000.0 | | 1.21 |
| MRP5099 | 53554 | 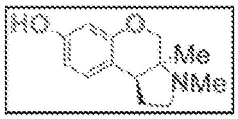 | | 1184.2 | | 65.2 | | 1.58 |
| MRP5098 | 53555 | 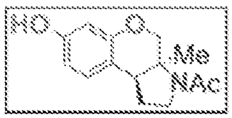 | | 10000.0 | | 10000.0 | 10000.0 | 0.85 |
| MRP5077 | 53551 | 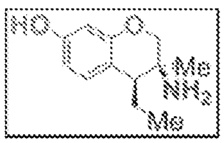 | | 10000.0 | | 10000.0 | | 1.61 |
| MRP3201 | 52291 | 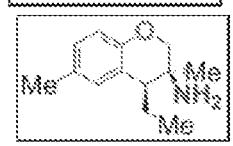 | 3084.0 | 177.0 | 10000.0 | 1053.0 | 10000.0 | 2.49 |
| MRP3200 | 52292 | 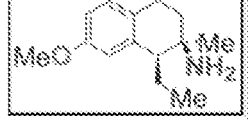 | 646.0 | 145.0 | 10000.0 | 118.0 | 10000.0 | 2.64 |
| MRP5065 | 53557 | 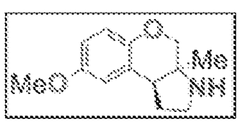 | | 707.9 | | 112.2 | | 1.47 |
| MRP5064 | 53556 | 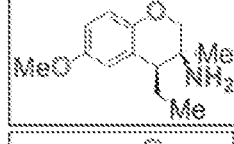 | | 205.3 | | 348.6 | 10000.0 | 1.88 |
| SM1051 | 53558 | 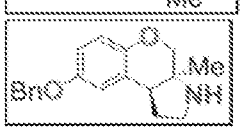 | | 448.6 | | 6.8 | | 3.2 |
| SM1053 | 53559 | 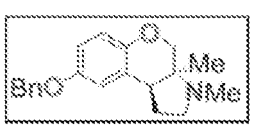 | | 539.8 | | 28.2 | | 3.58 |
FIG. 13D

Table 7

52293 (racemate) Summary and 5HT-7A Assay

| Receptor | Value | Receptor | Value |
|---|---|---|---|
| 5-HT$_{1A}$ | >10,000 | GABA$_A$ | >10,000 |
| 5-HT$_{1B}$ | >10,000 | H$_1$ | >10,000 |
| 5-HT$_{1D}$ | >10,000 | H$_2$ | 1878 |
| 5-HT$_{1E}$ | >10,000 | H$_3$ | >10,000 |
| 5-HT$_{2A}$ | >10,000 | H$_4$ | >10,000 |
| 5-HT$_{2B}$ | 475 | κ-OR | >10,000 |
| 5-HT$_{2C}$ | >10,000 | M$_1$ | >10,000 |
| 5-HT$_3$ | >10,000 | M$_2$ | >10,000 |
| 5-HT$_6$ | >10,000 | M$_3$ | >10,000 |
| 5-HT$_7$ | 6.3 | M$_4$ | >10,000 |
| Alpha$_{1A}$ | >10,000 | M$_5$ | >10,000 |
| Alpha$_{1B}$ | >10,000 | μ-OR | >10,000 |
| Alpha$_{1D}$ | 1,038 | NET | 1624 |
| Alpha$_{2A}$ | >10,000 | PBR | >10,000 |
| Alpha$_{2B}$ | >10,000 | σ$_1$ | 470 |
| Alpha$_{2C}$ | 974 | σ$_2$ | 634 |
| Beta$_1$ | 3267 | | |
| Beta$_2$ | >10,000 | | |
| Beta$_3$ | >10,000 | | |
| BZP | >10,000 | | |
| D$_1$ | >10,000 | | |
| D$_2$ | >10,000 | | |
| D$_3$ | >10,000 | | |
| D$_4$ | >10,000 | | |
| D$_5$ | >10,000 | | |
| DAT | >10,000 | | |
| δ-OR | >10,000 | | |

*FIG. 16*

Table 8

52294 (racemate) Summary and Sigma-1 Assay

| Receptor | Value | | Receptor | Value |
|---|---|---|---|---|
| 5-HT$_{1A}$ | 960 | | H$_1$ | >10,000 |
| 5-HT$_{1B}$ | >10,000 | | H$_2$ | >10,000 |
| 5-HT$_{1D}$ | >10,000 | | H$_3$ | >10,000 |
| 5-HT$_{1E}$ | >10,000 | | H$_4$ | >10,000 |
| 5-HT$_{2A}$ | >10,000 | | κ-OR | >10,000 |
| 5-HT$_{2B}$ | 227 | | M$_1$ | >10,000 |
| 5-HT$_{2C}$ | 1376 | | M$_2$ | >10,000 |
| 5-HT$_3$ | >10,000 | | M$_3$ | >10,000 |
| 5-HT$_6$ | >10,000 | | M$_4$ | >10,000 |
| 5-HT$_7$ | 1146 | | M$_5$ | >10,000 |
| Alpha$_{1A}$ | >10,000 | | μ-OR | >10,000 |
| Alpha$_{1B}$ | >10,000 | | NET | >10,000 |
| Alpha$_{1D}$ | >10,000 | | PBR | >10,000 |
| Alpha$_{2A}$ | 56% | | σ$_1$ | 44 |
| Alpha$_{2B}$ | >10,000 | | σ$_2$ | >10,000 |
| Alpha$_{2C}$ | >10,000 | | | |
| Beta$_1$ | 941 | | | |
| Beta$_2$ | 582 | | | |
| Beta$_3$ | >10,000 | | | |
| BZP | 6724 | | | |
| D$_1$ | >10,000 | | | |
| D$_2$ | >10,000 | | | |
| D$_3$ | >10,000 | | | |
| D$_4$ | >10,000 | | | |
| D$_5$ | >10,000 | | | |
| DAT | >10,000 | | | |
| δ-OR | >10,000 | | | |
| GABA$_A$ | >10,000 | | | |

FIG. 19

Table 9

| Compound ID (Internal ID/PDSP ID) | MRP3160/ 52290 | MRP3201/ 52291 | MRP3200/ 52292 | MRP3172/ 52293 | MRP3215/ 52294 | MRP3175/ 52295 |
|---|---|---|---|---|---|---|
| Receptor | $K_{i\,(nM)}$ | | | | | |
| 5-HT$_{2B}$ | 850 | 197 | 145 | 475 | 227 | 171 |
| 5-HT$_6$ | >10,000 | >10,000 | >10,000 | >10,000 | >10,000 | >10,000 |
| 5-HT$_7$ | 1,061 | >10,000 | >10,000 | Under 10,0C | Under 10,0 | Under 10,000 |
| Alpha 1D | >10,000 | >10,000 | >10,000 | 1,038 | >10,000 | 1,109 |
| Alpha 2C | >10,000 | >10,000 | >10,000 | 974 | >10,000 | >10,000 |
| H4 | >10,000 | >10,000 | >10,000 | >10,000 | >10,000 | >10,000 |
| M1 | >10,000 | >10,000 | >10,000 | >10,000 | >10,000 | >10,000 |
| M2 | >10,000 | >10,000 | >10,000 | >10,000 | >10,000 | >10,000 |
| M3 | >10,000 | >10,000 | >10,000 | >10,000 | >10,000 | 798 |
| M4 | >10,000 | >10,000 | >10,000 | >10,000 | >10,000 | >10,000 |
| M5 | >10,000 | >10,000 | >10,000 | >10,000 | >10,000 | >10,000 |
| NET | Under 10,0C | Under 10,00 | Under 10,00 | Under 10,0C | >10,000 | Under 10,000 |
| $\sigma_1$ | Under 10,0C | Under 10,00 | Under 10,00 | Under 10,0C | Under 10,0 | Under 10,000 |
| $\sigma_2$ | Under 10,0C | >10,000 | >10,000 | Under 10,0C | >10,000 | Under 10,000 |

*FIG. 23*

SUBSTITUTED PHENETHYLAMINE DERIVATIVES

STATEMENT OF GOVERNMENT RIGHTS

This invention was made with government support under GM124718 awarded by the National Institutes of Health. The government has certain rights in the invention.

BACKGROUND

G-protein-coupled receptors (GPCR) are a prominent pharmacological target. More than 30% of FDA approved drugs target at least one GPCR. Worldwide, more than 25% of drug sales come from GPCR modulating compounds. These compounds are used to treat a wide variety of diseases and disorders including allergies, schizophrenia, depression, pain management, and asthma. Common GPCR targeting pharmaceuticals include the antihistamine loratadine, antidepressants fluoxetine and sertraline, antipsychotics aripiprazole, clozapine, and haloperidol, the opioids morphine, hydrocodone, and fentanyl, and bronchodilators salbutamol and tiotropium bromide. A phenethylamine core is a privileged substructure in GPCR ligands. See representative phenethylamine-containing GPCR ligands below. This is partially because several endogenous neurotransmitters or neuromodulators are phenethylamines including dopamine and epinephrine (FIG. 1A). The phenethylamine backbone is also found in a wide variety of GCPR targeting active pharmaceutical ingredients including morphine, salbutamol, and pseudoephedrine (FIG. 1B).

Tetralins, chromanes, and tetrahydroquinolines represent privileged structural motifs present in pharmaceuticals, agrochemicals, and natural products. These molecules display a wide range of activity including treatments or potential treatments for cancer, pain, depression, thrombosis, Parkinson's disease, and malaria. Due to this rich history, numerous synthetic methods can generate these systems including cyclization, annulation, cycloaddition, partial reduction, and others. However, a synthetic method that exploits allylic azide rearrangement to generate such privileged structural motifs has not been realized. In particular, chemists have struggled to exploit this rearrangement synthetically because of difficulty differentiating the azide isomers. Only a few reports accomplished selective elaboration. There have been reports in the literature of a tandem Claisen rearrangement in which selectivity was achieved by orchestrating a second irreversible sigmatropic process. There have also been reports of a tandem Schmidt reaction that attained selectivity through cyclization and achieved diastereocontrol via chair-like intermediates. None, however, have been able to synthesize tetralins, chromanes, and tetrahydroquinolines.

Accordingly, it would be desirable to develop tetralins, chromanes, and tetrahydroquinolines with a phenethylamine core using a synthetic route capable of forming differentially functionalized azides from an equilibrating mixture of allylic azides and that permits selective elaboration of products.

SUMMARY OF INVENTION

In one aspect, the present invention is directed to compounds represented by formulas (I) or (II):

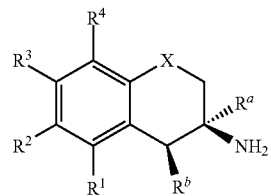

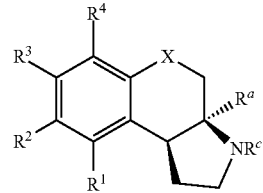

or stereoisomers, tautomers, or pharmaceutically acceptable salts thereof, wherein:

X is selected from the group consisting of —$CH_2$—, —O—, and —N(R')—, wherein R', if present, is selected from hydrogen, substituted or unsubstituted aryl group, and substituted or unsubstituted arylsulfonyl group;

$R^a$ and $R^b$ are each independently selected from hydrogen, substituted or unsubstituted alkyl, substituted or unsubstituted alkenyl, substituted or unsubstituted aralkyl;

$R^c$ is selected from hydrogen, substituted or unsubstituted alkyl, substituted or unsubstituted acyl, and substituted or unsubstituted aryl; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

In another aspect, the present invention is directed to methods of synthesizing the compounds of formulas (I) and (II) via a tandem Winstein rearrangement Friedel-Crafts alkylation.

In another aspect, the present invention is directed to pharmaceutical compositions comprising a therapeutically effective amount of the compounds of formulas (I) and/or (II), or a pharmaceutically acceptable salt thereof, in combination with one or more pharmaceutically acceptable carriers.

In another aspect, the present invention is directed to methods of treating conditions, disorders, or deficits modulated by a receptor selected from the group consisting of a 5-$HT_{1A}$ receptor, 5-$HT_{1B}$ receptor, 5-$HT_{1D}$ receptor, 5-$HT_{1E}$ receptor, 5-$HT_{2A}$ receptor, 5-$HT_{2B}$ receptor, 5-$HT_{2C}$ receptor, 5-$HT_3$ receptor, 5-$HT_6$ receptor, 5-$HT_7$ receptor, Alpha$_{1A}$ receptor, Alpha$_{1B}$ receptor, Alpha$_{1D}$ receptor, Alpha$_{2A}$ receptor, Alpha$_{2B}$ receptor, Alpha$_{2C}$ receptor, Beta$_1$ receptor, Beta$_2$ receptor, Beta$_3$ receptor, BZP receptor, $D_1$ receptor, $D_2$ receptor, $D_3$ receptor, $D_4$ receptor, $D_5$ receptor, DAT receptor, δ-OR receptor, GABA$_A$ receptor, $H_1$ receptor, $H_2$ receptor, $H_3$ receptor, $H_4$ receptor, κ-OR receptor, $M_1$ receptor, $M_2$ receptor, $M_3$ receptor, $M_4$ receptor, $M_5$ receptor, μ-OR receptor, NET receptor, PBR receptor, $\sigma_1$ receptor, $\sigma_2$ receptor, or combinations thereof, the method comprising administering to a subject a therapeutically effective amount of the compounds of formulas (I) and/or (II), or a pharmaceutically acceptable salt thereof.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which:

FIG. 6 presents Table 1 summarizing the GPCR binding affinity of compounds (3a), (3b), and (3c), according to one or more embodiments of the present disclosure.

FIG. 7 presents Table 2 summarizing K$_i$ data for primary amino-chromanes, according to one or more embodiments of the present disclosure.

FIG. 8 presents Table 3 summarizing K$_i$ data for pyrrolidine containing chromanes, according to one or more embodiments of the present disclosure.

FIGS. 11A-11B is a (a) graphical view and (b) tabular view of a competition binding curve for compound 52294 and haloperidol as a reference compound, according to one or more embodiments of the present disclosure.

FIGS. 12A-12B is a (a) graphical view and (b) tabular view of a competition binding curve for compound 52293 and clozapine as a reference compound, according to one or more embodiments of the present disclosure.

FIGS. 13A-13E presents Table 6 which summarizes the binding affinity of various compounds against 5-HT$_{1A}$, 5-HT$_{2B}$, 5-HT$_7$, sigma-1, and sigma-2 GPCR receptors, according to one or more embodiments of the present disclosure.

FIG. 16 presents Table 7 summarizing the binding affinity of compound 52293 against various GPCR, according to one or more embodiments of the present disclosure.

FIG. 19 presents Table 8 summarizing the binding affinity of compound 52294 against various GPCR, according to one or more embodiments of the present disclosure.

FIG. 23 presents Table 9 summarizing the binding affinity of compounds 52290-52295 against various GPCR, according to one or more embodiments of the present disclosure.

DETAILED DESCRIPTION

Figure 1A:
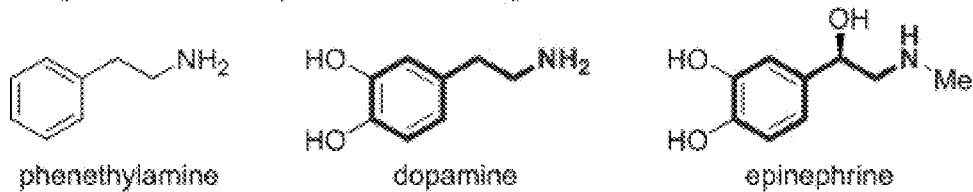
FIGS. 1A-1B show representative phenethylamine-containing GPCR ligands including (a) endogenous phenthyalmine GCPR ligands and (b) common phenethylamine GPCR ligands, according to one or more embodiments of the present disclosure.
Figure 1B:
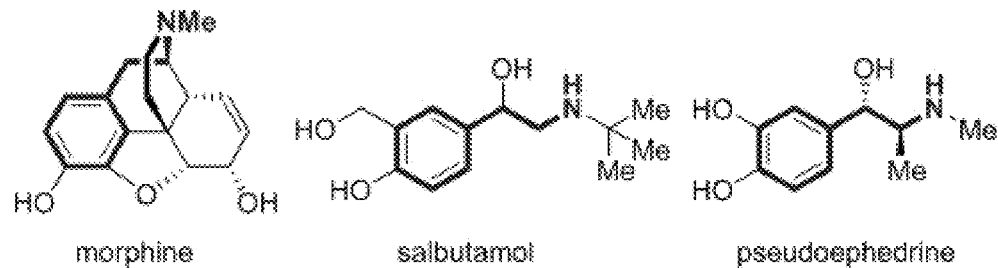

The invention of the present disclosure relates to novel substituted phenethylamine derivatives that exhibit selective and/or potent inhibitory effects against various central nervous system (CNS) receptors. Such compounds include mono- and multi-substituted tetralins, chromanes, and tetrahydroquinolines featuring, among other things, an amine in the C-3 position to afford compounds with a phenethylamine backbone/core. For example, in some embodiments, the compounds described herein include mono- and multi-substituted tetralins, chromanes, and tetrahydroquinolines with either a primary amine in the C-3 position or a pyrrolidine motif fused at the C-3 and C-4 positions. In addition, the tetralin, chromane, and tetrahydroquinoline compounds can incorporate and/or be decorated with a variety of substituents and heteroatoms, providing access to a wide array of structural analogues. These structure features in combination with the compounds' small molecular weight and rigid structures yield a new class of compounds with low nanomolar binding affinity for various central nervous system receptors.

Definitions

The terms recited below have been defined as described below. All other terms and phrases in this disclosure shall be construed according to their ordinary meaning as understood by one of skill in the art.

As used herein, the term "stereoisomer" refers to a compound made of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The prefixes (+), (−), and (±) are used herein as commonly used in organic chemistry to denote ratios of dextrorotatory and levorotatory isomers. The prefix (+) refers to a dextrorotary compound. The prefix (−) refers to a levorotatory compound. The prefix (±) refers to a racemic mixture with a 1:1 ratio of dextrorotatory and levorotatory compounds. The prefix (+/−) refers to a racemic mixture in which the ratio of dextrorotatory and levorotatory compounds is not 1:1.

The designation "━�ન" refers to a bond that protrudes forward out of the plane of the page.

The designation "⋅⋅⋅ıl" refers to a bond that protrudes backward out of the plane of the page.

In the context of chemical formulas, the symbol "-" means a single bond, and the symbol "=" means a double bond.

As used herein, the term "substituted" refers to all permissible substituents of the compounds described herein. In the broadest sense, the permissible substituents include acyclic and cyclic, branched and unbranched, carbocyclic and heterocyclic, aromatic and nonaromatic substituents of organic compounds. Non-limiting examples of substituents include halogens, hydroxyl groups, or any other organic groupings containing any number of carbon atoms and optionally include one or more heteroatoms such as oxygen, nitrogen, or sulfur grouping in linear, branched, or cyclic structural formats.

Representative substituents include halo, hydroxyl, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aryloxy, substituted aryloxy, aralkoxy, substituted aralkoxy, alkenyloxy, substituted alkenyloxy, alkynyloxy, substituted alkynyloxy, heteroaryloxy, substituted heteroaryloxy, acyloxy, substituted acyloxy, carbonyl, substituted carbonyl, carboxyl, substituted carboxyl, amino, substituted amino, amido, substituted amido, sulfonyl, substituted sulfonyl, arylsulfonyl, substituted arylsulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, and amino acid groups.

When any of these terms is used with the "substituted" modifier, one or more hydrogen atoms have been independently replaced by one or more of the following non-limiting examples of substituents: —OH, —Br, —Cl, —I, —$CH_3$, —$CH_2CH_3$, —CH═$CH_2$, —$C_6H_5$ (phenyl, Ph), —$CH_2$-Ph (benzyl, Bn), —$CH_2CH_2$-Ph, —$OCH_3$, —$OCH_2CH_3$, —$OCH_2CH_2CH_3$, —$OCH(CH_3)_2$, —O-Ph, —$OCH_2$-Ph, —$OCH_2CH_2$-Ph, —$OC_3H_5$, —$OC_4H_7$, —$OC_5H_9$, —$OC_6H_{11}$, —$OCH_2C_3H_5$, —$OCH_2C_4H_7$, —$OCH_2C_5H_8$, —$OCH_2C_6H_{11}$, —$CF_3$, and —$C(O)CH_3$.

As used herein, "heteroatom" means an atom of any element other than carbon or hydrogen. Preferred heteroatoms are nitrogen, oxygen, boron, phosphorus, sulfur, and selenium. Other heteroatoms include silicon and arsenic. As discussed herein, heteroatoms, such as nitrogen, may have hydrogen substituents and/or any permissible substituents of organic compounds described herein which satisfy the valences of the heteroatoms.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —Br, —Cl, —I, —$CH_3$, —$CH_2CH_3$, —CH═$CH_2$, —$C_6H_5$ (phenyl, Ph), —$CH_2$-Ph (benzyl, Bn), —$OCH_3$, —$OCH_2CH_3$, —$OCH_2CH_2CH_3$, —$OCH(CH_3)_2$, —O-Ph, —$OCH_2$-Ph, —$OCH_2CH_2$-Ph, —$OC_3H_5$, —$OC_4H_7$, —$OC_5H_9$, —$OC_6H_{11}$, —$OCH_2C_3H_5$, —$OCH_2C_4H_7$, —$OCH_2C_5H_8$, —$OCH_2C_6H_{11}$, —$CF_3$, and —$C(O)CH_3$.

As used herein, the term "alkyl" when used without the "substituted" modifier refers to an alkane with one hydrogen atom removed and includes straight chain alkyl groups, branched chain alkyl groups, cycloalkyl (alicyclic) groups, alkyl-substituted cycloalkyl groups, and cycloalkyl-substituted alkyl groups. A straight chain or branched chain alkyl has 30 or fewer carbon atoms in its backbone (e.g., $C_1$-$C_{30}$ for straight chains, and $C_3$-$C_{30}$ for branched chains). Cycloalkyls have 3-10 carbon atoms in their ring, preferably 5-6 carbons in the ring. The groups —$CH_3$ (Me), —$CH_2CH_3$ (Et), —$CH_2CH_2CH_3$ (n-Pr), —$CH(CH_3)_2$(iso-Pr), —CH$(CH_2)_2$(cyclopropyl), —$CH_2CH_2CH_2CH_3$ (n-Bu), —CH$(CH_3)CH_2CH_3$ (sec-butyl), —$CH_2CH(CH_3)_2$(iso-butyl), —$C(CH_3)_3$(tert-butyl), —$CH_2C(CH_3)_3$(neo-pentyl), cyclopropyl, cyclobutyl, cyclopentyl, cyclohexyl, and cyclohexylmethyl are non-limiting examples of alkyl groups. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$.

As used herein, the term "heteroalkyl" refers to straight or branched chain, or cyclic carbon containing radicals, or combinations thereof, containing at least one heteroatom. Suitable heteroatoms include, but are not limited to, O, N, Si, P, Se, B, and S. Heteroalkyls can be substituted as defined above for alkyl groups.

As used herein, the term "alkenyl" when used without the "substituted" modifier refers to a straight- or branched-chain hydrocarbon moiety having at least one carbon-carbon double bond. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, —CH═CH—C$_6$H$_5$, —CH═CH—, —CH═C(CH$_3$)CH$_2$—, and —CH═CHCH$_2$—. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$. The groups, —CH═CHF, —CH═CHCl and —CH═CHBr, are non-limiting examples of substituted alkenyl groups. An "alkene" refers to the compound H—R, wherein R is alkenyl.

As used herein, the term "alkynyl" when used without the "substituted" modifier refers to a straight- or branched-chain hydrocarbon moiety having at least one carbon-carbon triple bond. As used herein, the term alkynyl does not preclude the presence of one or more non-aromatic carbon-carbon double bonds. The groups —C≡CH, —C≡CCH$_3$, and —CH$_2$C≡CCH$_3$, are non-limiting examples of alkynyl groups. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$. An "alkyne" refers to the compound H—R, wherein R is alkynyl.

As used herein, the term "aryl" when used without the "substituted" modifier refers to a monocyclic or polycyclic aromatic group with carbon atoms forming an aromatic ring structure, wherein the ring atoms are all carbon, and wherein the group consists of no atoms other than carbon and hydrogen. If more than one ring is present, the rings may be fused or not fused. As used herein, the term does not preclude the presence of one or more alkyl groups attached to the first aromatic ring or any additional aromatic ring present. The point of attachment can be an aromatic carbon atom in the ring structure or a carbon atom of an alkyl group attached to the ring structure. Non-limiting examples of aryl groups include phenyl (Ph), methylphenyl, (dimethyl)phenyl, —C$_6$H$_4$—CH$_2$CH$_3$ (ethylphenyl), naphthyl, and the monovalent group derived from biphenyl. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$. An "arene" refers to the compound H—R, wherein R is aryl.

As used herein, the term "heteroaryl" when used without the "substituted" modifier refers to a monocyclic or polycyclic aromatic group with one or more aromatic non-carbon atoms forming at least part of an aromatic ring structure. Non-limiting examples of non-carbon atoms in the aromatic ring structure include nitrogen, oxygen, and sulfur. As used herein, the term does not preclude the presence of one or more alkyl group (carbon number limitation permitting) attached to the aromatic ring or any additional aromatic ring present. The point of attachment can be an aromatic carbon or non-carbon atom in the aromatic ring structure or a carbon atom of an alkyl group attached to the aromatic ring structure. Non-limiting examples of heteroaryl groups include furanyl, imidazolyl, indolyl, indazolyl, methylpyridyl, oxazolyl, pyridyl, pyrrolyl, pyrimidyl, pyrazinyl, quinolyl, quinazolyl, quinoxalinyl, thienyl, and triazinyl. Heteroaryls can be substituted as defined above for aryl groups.

The term "aralkyl" when used without the "substituted" modifier refers to an alkyl as previously defined, wherein one of the hydrogen atoms is replaced by an aryl and/or heteroaryl group as defined above. Non-limiting examples of aralkyls are: phenylmethyl (benzyl, Bn) and 2-phenylethyl. The point of attachment can be an aromatic carbon atom in the ring structure or a carbon atom of an alkyl group attached to the ring structure. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$. Non-limiting examples of substituted aralkyls are: (3-chlorophenyl)-methyl and 2-chloro-2-phenyl-eth-1-yl.

As used herein, the term "alkaryl" when used without the "substituted" modifier refers to an aryl and/or heteroaryl group as described herein, wherein one or more of the hydrogen atoms is replaced by an alkyl and/or heteroalkyl group as defined herein. The point of attachment can be an aromatic carbon atom in the ring structure or a carbon atom of an alkyl group attached to the ring structure. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$.

As used herein, the term "haloaryl" when used without the "substituted" modifier refers to an aryl and/or heteroaryl group as defined herein, wherein one or more of the hydrogen atoms is replaced by a halogen as described herein. The point of attachment can be an aromatic carbon atom in the ring structure or a carbon atom of an alkyl group attached to the ring structure. When these terms are used with the "substituted" modifier one or more hydrogen atom has been independently replaced by —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$.

As used herein, the term "alkoxy" when used without the "substituted" modifier refers to the group —OR, wherein R is an alkyl and/or heteroalkyl as defined herein. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —OC$_3$H$_6$, —OC$_4$H$_8$, —OC$_5$H$_{10}$, —OC$_6$H$_{12}$, —OCH$_2$C$_3$H$_6$, —OCH$_2$C$_4$H$_8$, —OCH$_2$C$_5$H$_{10}$, —OCH$_2$C$_6$H$_{12}$, and the like. When any of these terms is used with the "substituted" modifier, one or more hydrogen atoms have been independently replaced by one or more of the following non-limiting examples of substituents: —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —CH$_2$CH$_2$-Ph, —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$.

As used herein, the terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Examples include without limitation aryloxy groups such as —O-Ph and aralkoxy groups such as —OCH$_2$-Ph (—OBn) and —OCH$_2$CH$_2$-Ph. When any of these terms is used with the "substituted" modifier, one or more hydrogen atoms have been independently replaced by one or more of the following non-limiting examples of substituents: —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —CH$_2$CH$_2$-Ph, —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$.

As used herein, the term "acyl" when used without the "substituted" modifier refers to the group —C(O)R, in which R is a hydrogen, alkyl, aryl, aralkyl or heteroaryl, as those terms are defined above. Non-limiting examples of acyl groups include: —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$—CH$_3$, —C(O)CH$_2$C$_6$H$_5$, amd —C(O)(imidazolyl). When any of these terms is used with the "substituted" modifier, one or more hydrogen atoms have been independently replaced by one or more of the following non-limiting examples of substituents: —OH, —Br, —Cl, —I, —CH$_3$, —CH$_2$CH$_3$, —CH═CH$_2$, —C$_6$H$_5$ (phenyl, Ph), —CH$_2$-Ph (benzyl, Bn), —CH$_2$CH$_2$-Ph, —OCH$_3$, —OCH$_2$CH$_3$, —OCH$_2$CH$_2$CH$_3$, —OCH(CH$_3$)$_2$, —O-Ph, —OCH$_2$-Ph, —OCH$_2$CH$_2$-Ph, —OC$_3$H$_5$, —OC$_4$H$_7$, —OC$_5$H$_9$, —OC$_6$H$_{11}$, —OCH$_2$C$_3$H$_5$, —OCH$_2$C$_4$H$_7$, —OCH$_2$C$_5$H$_8$, —OCH$_2$C$_6$H$_{11}$, —CF$_3$, and —C(O)CH$_3$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

As used herein, the term "halide" or "halo" or "halogen" refers to —F, —Cl, —Br, or —I.

As used herein, the term "hydroxy" or "hydroxyl" refers to —OH.

Compounds Generally

The compounds of the present disclosure can be represented by general formulas (I) or (II):

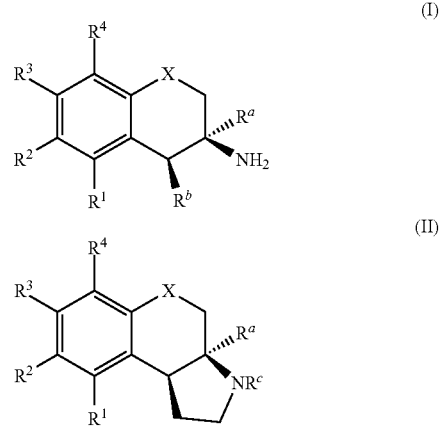

or stereoisomers, tautomers, or pharmaceutically acceptable salts thereof, wherein:

X is selected from the group consisting of —CH$_2$—, —O—, and —N(R')—, wherein R', if present, is selected from hydrogen, substituted or unsubstituted aryl group, and substituted or unsubstituted arylsulfonyl group;

$R^a$ and $R^b$ are each independently selected from hydrogen, substituted or unsubstituted alkyl, substituted or unsubstituted alkenyl, substituted or unsubstituted aralkyl;

$R^c$ is selected from hydrogen, substituted or unsubstituted alkyl, substituted or unsubstituted acyl, and substituted or unsubstituted aryl; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

In some embodiments, R' is selected from:

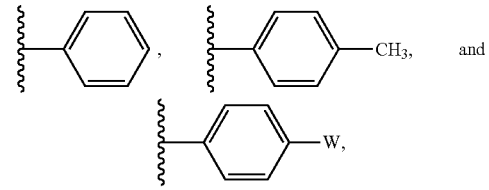

wherein W is —Br, —Cl, or —I. In some embodiments R' is selected from:

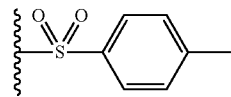

In some embodiments, $R^1$, $R^2$, $R^3$, and $R^4$ are each, if present, independently selected from: $—OCH_2CH_3$, $—O(CH_2)_2CH_3$, $—OCH(CH_3)_2$, $—OC_3H_5$, $—OC_4H_7$, $—OC_5H_9$, $—OC_6H_{11}$, $—OCH_2C_3H_5$, $—OCH_2C_4H_7$, $—OCH_2C_5H_8$, $—OCH_2C_6H_{11}$, $—OPh$, $—OCH_2Ph$, $—O(CH_2)_2Ph$. In some embodiments, the aromatic or non-aromatic ring is optionally substituted with one or more of $—OCH_3$, $—Cl$, $—Br$, $—I$, and $CF_3$. For example, in some embodiments, $R^1$, $R^2$, $R^3$, and $R^4$ are each, if present, independently selected from

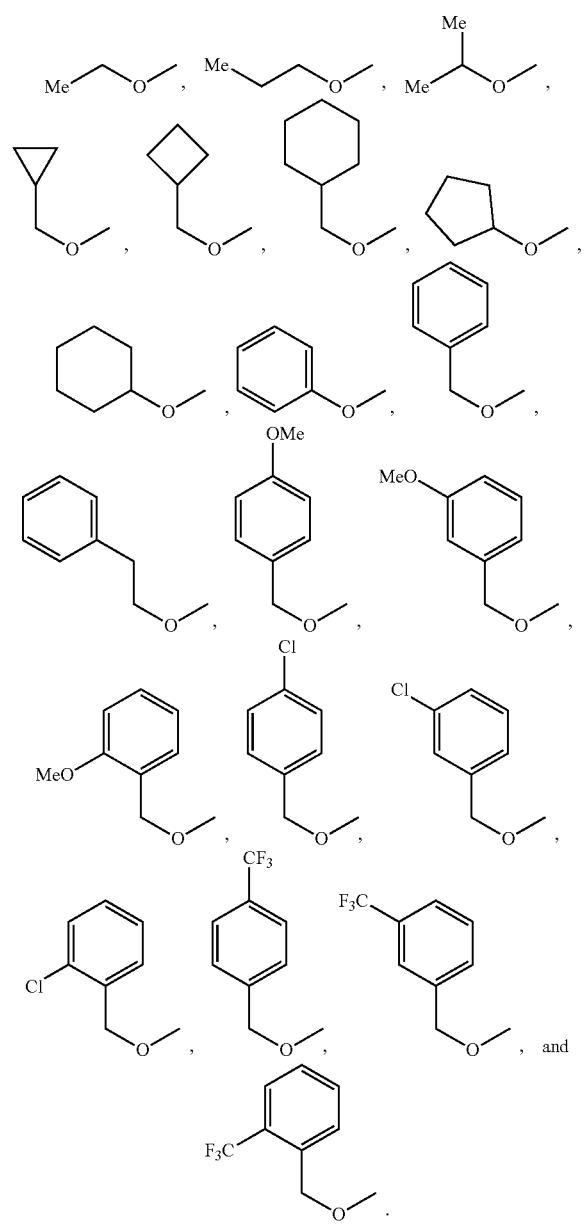

Compounds Featuring Primary Amines

Tetralins

In some embodiments, the compounds of formula (I) include compounds represented by formula (I-1):

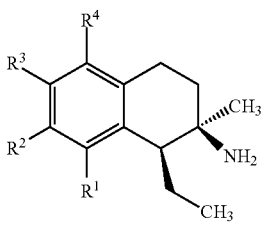

(I-1)

or stereoisomers, tautomers, or pharmaceutically acceptable salts thereof, wherein:

$R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form a fused aromatic or non-aromatic 6-membered carbocyclic ring.

A specific example of a compound of formula (I-1) which is contemplated as part of the present invention includes, but is not limited to, compounds represented by formula (I-1a):

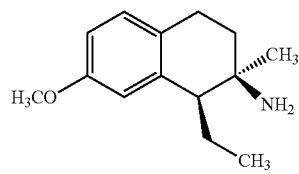

(I-1a)

Chromanes

In some embodiments, the compounds of formula (I) include compounds represented by formula (I-2):

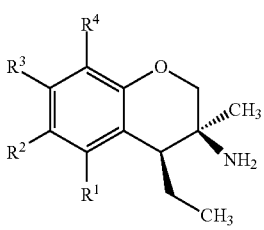

(I-2)

or stereoisomers, tautomers, or pharmaceutically acceptable salts thereof, wherein:

$R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

Specific examples of compounds of formula (I-2) which are contemplated as part of the present invention include, but are not limited to, the compounds represented by formulas (I-2a) to (I-2g):

(I-2a)
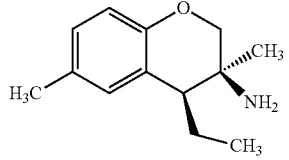

(I-2b)
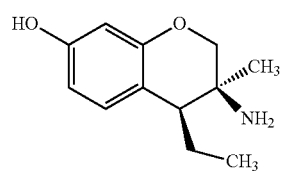

(I-2c)
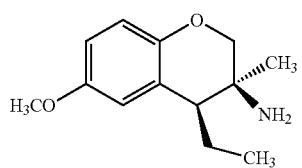

(I-2d)
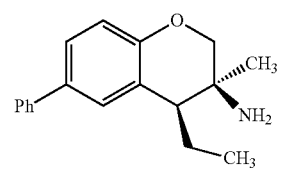

(I-2e)
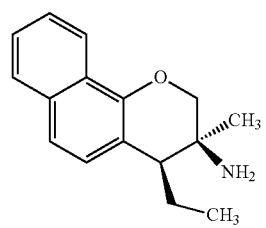

(I-2f)
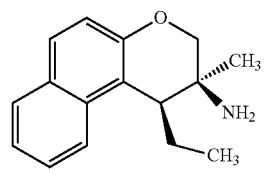

(I-2g)
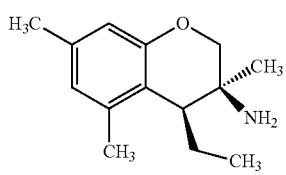

Tetrahydroquinolines

In some embodiments, the compounds of formula (I) include compounds represented by formula (I-3):

(I-3)
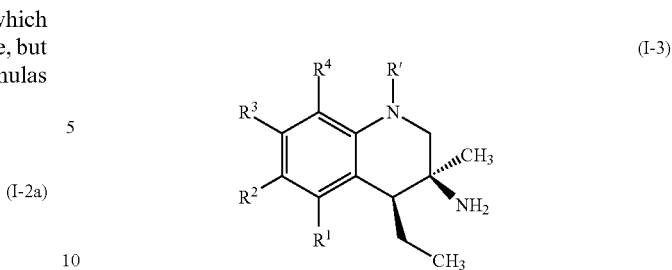

or stereoisomers, tautomers, or pharmaceutically acceptable salts thereof, wherein:

R' is selected from hydrogen, substituted or unsubstituted aryl group, and substituted or unsubstituted arylsulfonyl group; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

In some embodiments, R' is selected from:

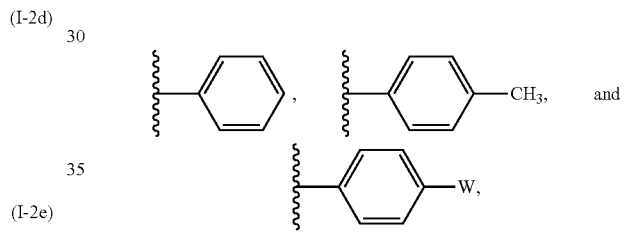

wherein W is —Br, —Cl, or —I. In some embodiments R' is selected from:

A specific example of a compound of formula (I-3) which is contemplated as part of the present invention includes, but is not limited to, the compound represented by formula (I-3a):

(I-3a)
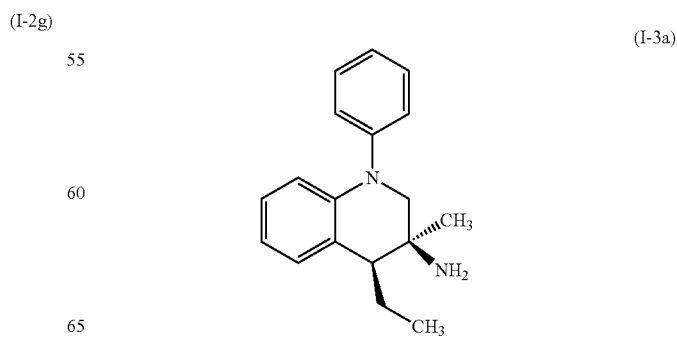

Compounds Featuring Pyrrolidine Motifs

Tetralins

In some embodiments, the compounds of formula (II) include compounds represented by the formula (II-1):

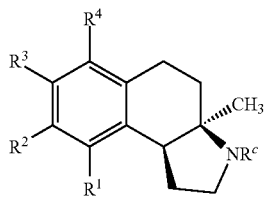
(II-1)

or stereoisomers, tautomers, or pharmaceutically acceptable salts thereof, wherein:

$R^c$ is selected from hydrogen, substituted or unsubstituted alkyl, substituted or unsubstituted acyl, and substituted or unsubstituted aryl groups; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

A specific example of a compound of formula (I-1) which is contemplated as part of the present invention includes, but is not limited to, compounds represented by formula (II-1a):

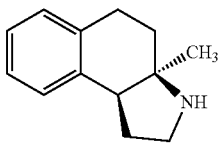
(II-1a)

Chromanes

In some embodiments, the compounds of formula (II) include compounds represented by formula (II-2):

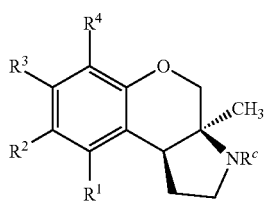
(II-2)

or stereoisomers, tautomers, or pharmaceutically acceptable salts thereof, wherein:

$R^c$ is selected from hydrogen, substituted or unsubstituted alkyl, substituted or unsubstituted acyl, and substituted or unsubstituted aryl groups; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

Specific examples of compounds of formula (II-2) which are contemplated as part of the present invention include, but are not limited to, the compounds represented by formulas (II-2a) to (II-2hhh):

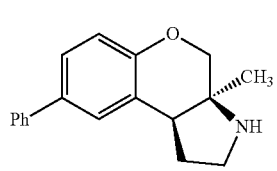
(II-2a)

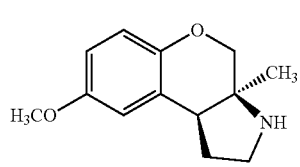
(II-2b)

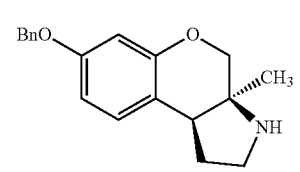
(II-2c)

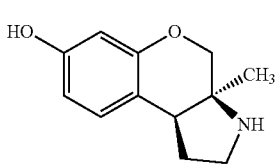
(II-2d)

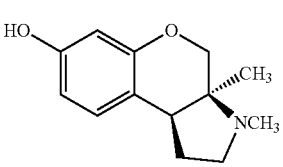
(II-2e)

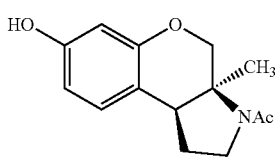
(II-2f)

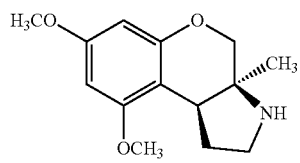
(II-2g)

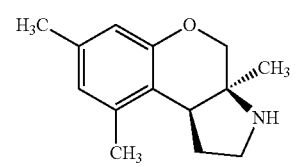
(II-2h)
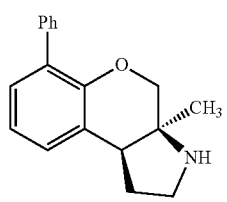
(II-2i)
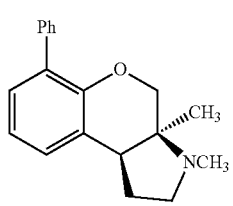
(II-2j)
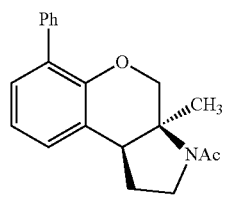
(II-2k)
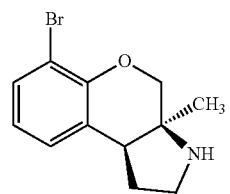
(II-2l)
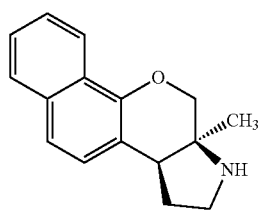
(II-2m)
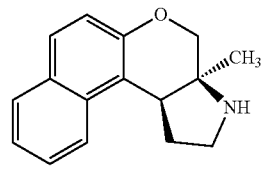
(II-2n)
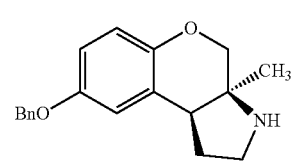
(II-2o)
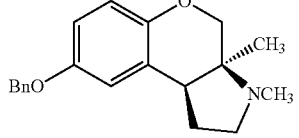
(II-2p)
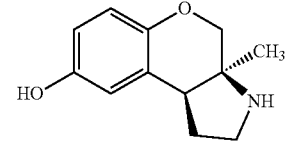
(II-2q)
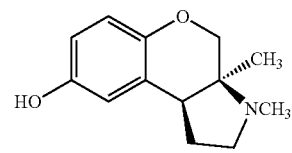
(II-2r)
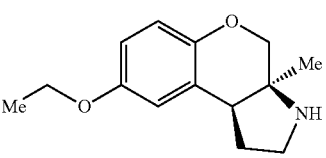
(II-2s)
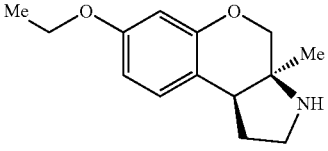
(II-2t)
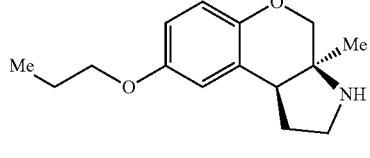
(II-2u)
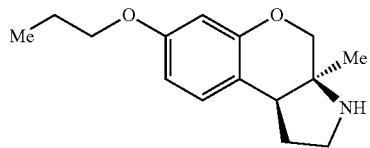
(II-2v)
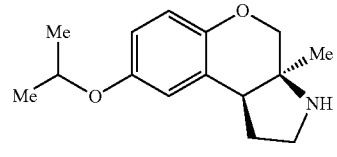
(II-2w)
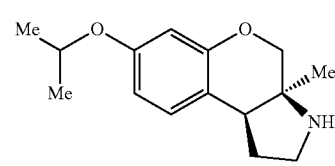
(II-2x)
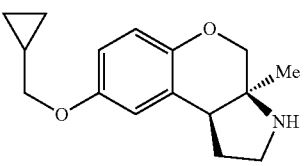
(II-2y)

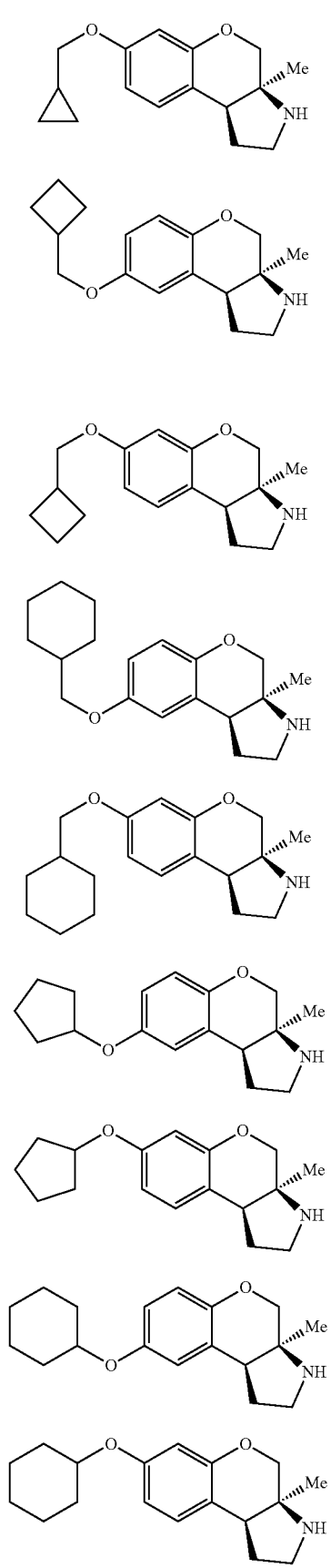
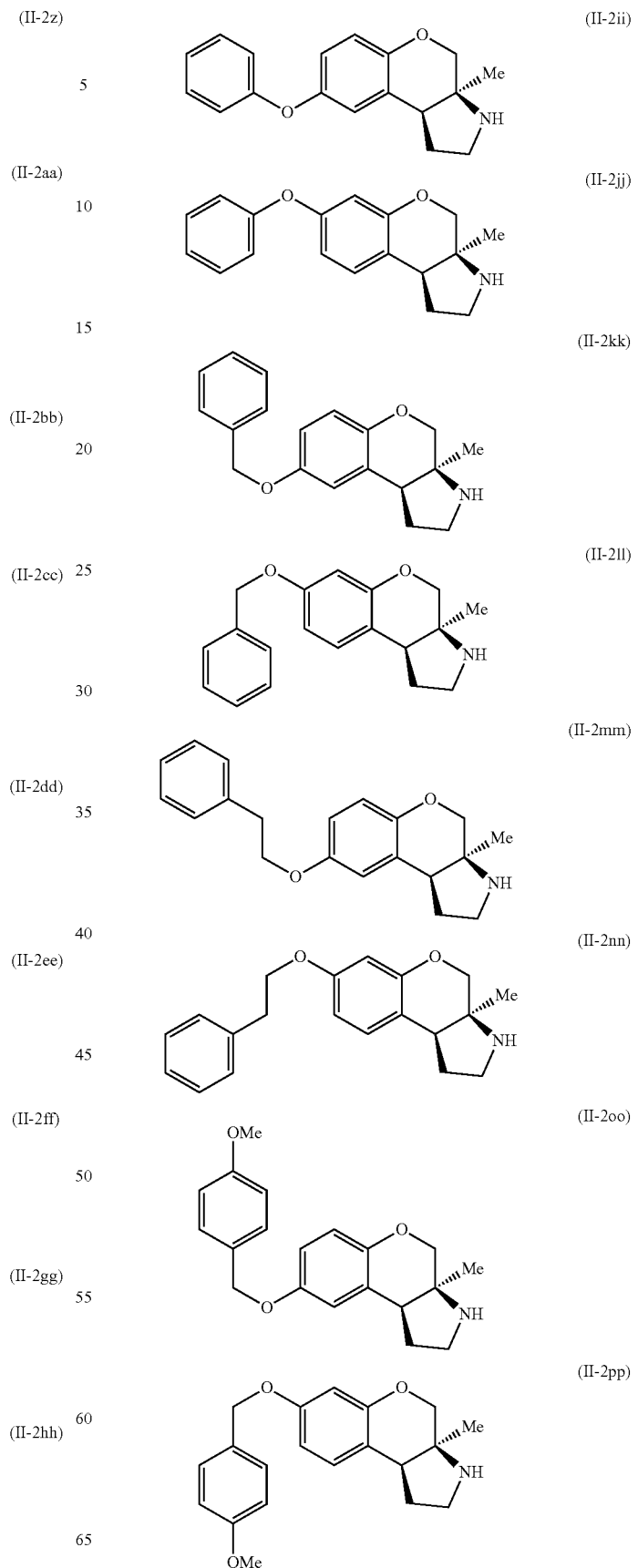

(II-2qq)
(II-2rr)
(II-2ss)
(II-2tt)
(II-2uu)
(II-2vv)
(II-2ww)
(II-2xx)
(II-2yy)
(II-2zz)
(II-2aaa)
(II-2bbb)
(II-2ccc)
(II-2ddd)

-continued

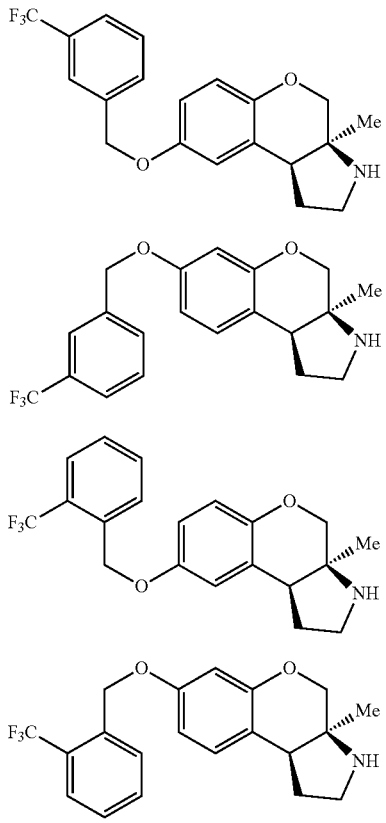

(II-2eee)

(II-2fff)

(II-2ggg)

(II-2hhh)

Tetrahydroquinolines

In some embodiments, the compounds of formula (II) include compounds represented by formula (II-3):

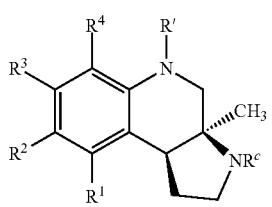

(II-3)

or stereoisomers, tautomers, or pharmaceutically acceptable salts thereof, wherein:

$R^c$ is selected from hydrogen, substituted or unsubstituted alkyl, substituted or unsubstituted acyl, and substituted or unsubstituted aryl; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one or more of $R^1$ and $R^2$, $R^2$ and $R^3$, and $R^3$ and $R^4$ bind with each other to form an aromatic or non-aromatic 6-membered carbocyclic ring.

In some embodiments, R' is selected from:

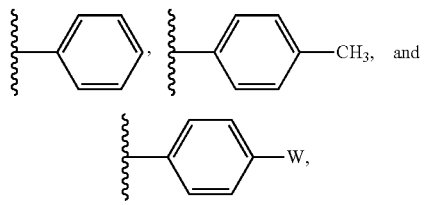

wherein W is —Br, —Cl, or —I. In some embodiments R' is selected from:

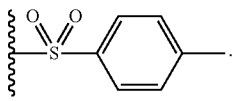

Specific examples of compounds of formula (II-3) which are contemplated as part of the present invention include, but are not limited to, the compounds represented by formulas (II-3a) to (II-3e):

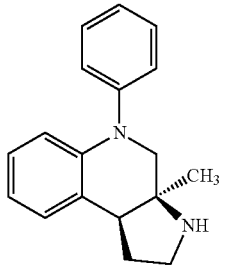

(II-3a)

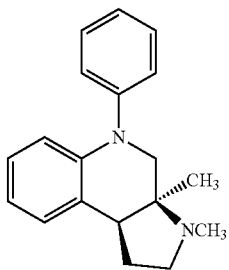

(II-3b)

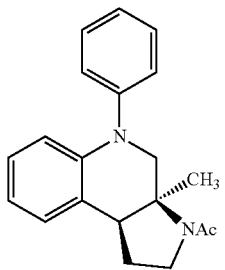

(II-3c)

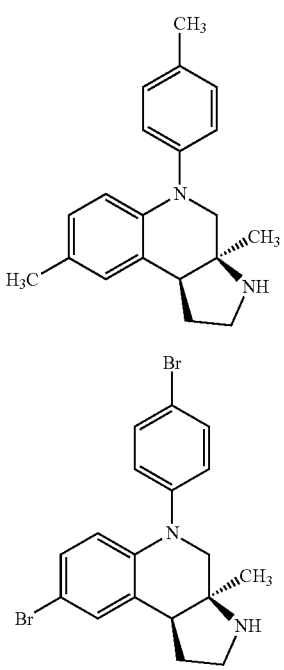

(II-3d)

(II-3e)

Compounds of formulas (I) and (II), and any variations thereof, can exist as stereoisomers. The present invention thus contemplates various stereoisomers and mixtures thereof, both of which are specifically included within the scope of the present invention. Stereoisomers include enantiomers, diastereomers, and mixtures of enantiomers and/or diastereomers. Accordingly, compounds of formulas (I) and (II) can exist as pure enantiomers or as racemic mixtures.

Methods of Synthesizing

Substituted Phenethylamine Derivatives

In another aspect, the present invention is directed to novel methods of synthesizing substituted phenethylamine derivatives (e.g., compounds of formulas (I) and (II)) comprising a tetralin, chromane, or tetrahydroquinoline core and either a primary amine at the C-3 position or pyrrolidine motif at the C-3 and C-4 position. In particular, the methods described herein can achieve stereoselective dynamic cyclization of allylic azides to achieve the stereoselective synthesis of 3-azido-tetralins, -chromanes, and -tetrahydroquinolines via a tandem allylic azide rearrangement/Friedel-Crafts alkylation. These intermediates can be readily elaborated to obtain the substituted phenethylamine derivatives of the present disclosure.

Figure 2A:
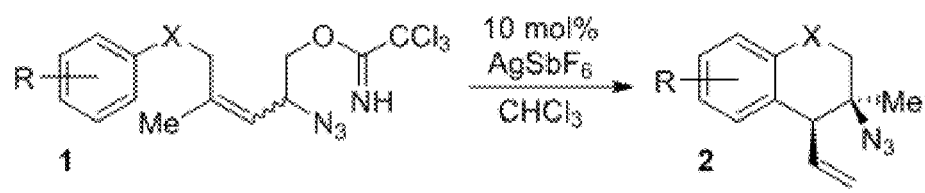
FIGS. 2A-2B show reaction schemes (a) and (b) of the novel methods of synthesis described herein, according to one or more embodiments of the present disclosure.
Figure 2B:
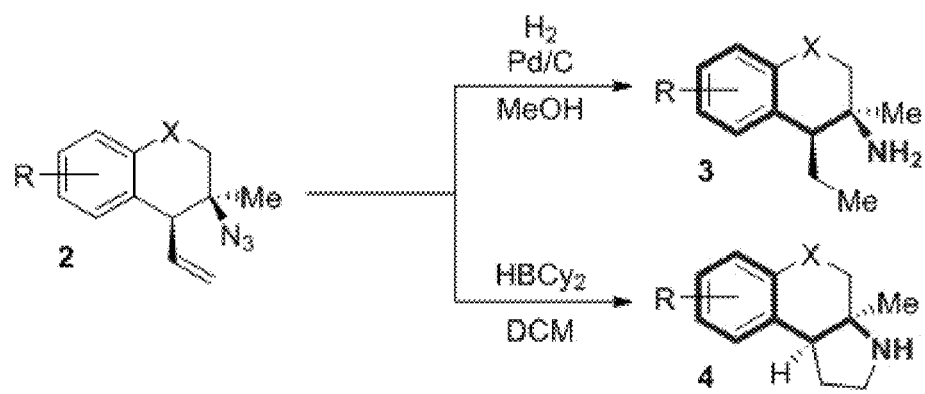

More specifically, the compounds of the present disclosure can be synthesized by a tandem Winstein rearrangement Friedel-Crafts alkylation that enables the synthesis of differentially functionalized heterocyclic tertiary azides from an equilibrating mixture of allylic azides (FIG. 2A). This cascade can be synthetically attractive because it can successfully differentiate the equilibrating azide isomers, providing products in excellent yield and selectivity (>25 examples, up to 94% yield and >25:1 dr). It can also construct tetralins, chromanes, and tetrahydroquinolines featuring a tetra-substituted stereocenter while maintaining a diversifiable vinyl group. The heterocyclic products can be readily converted into substituted phenethylamine derivatives containing either a primary amine or pyrrolidine motif (FIG. 2B).

Figure 3:
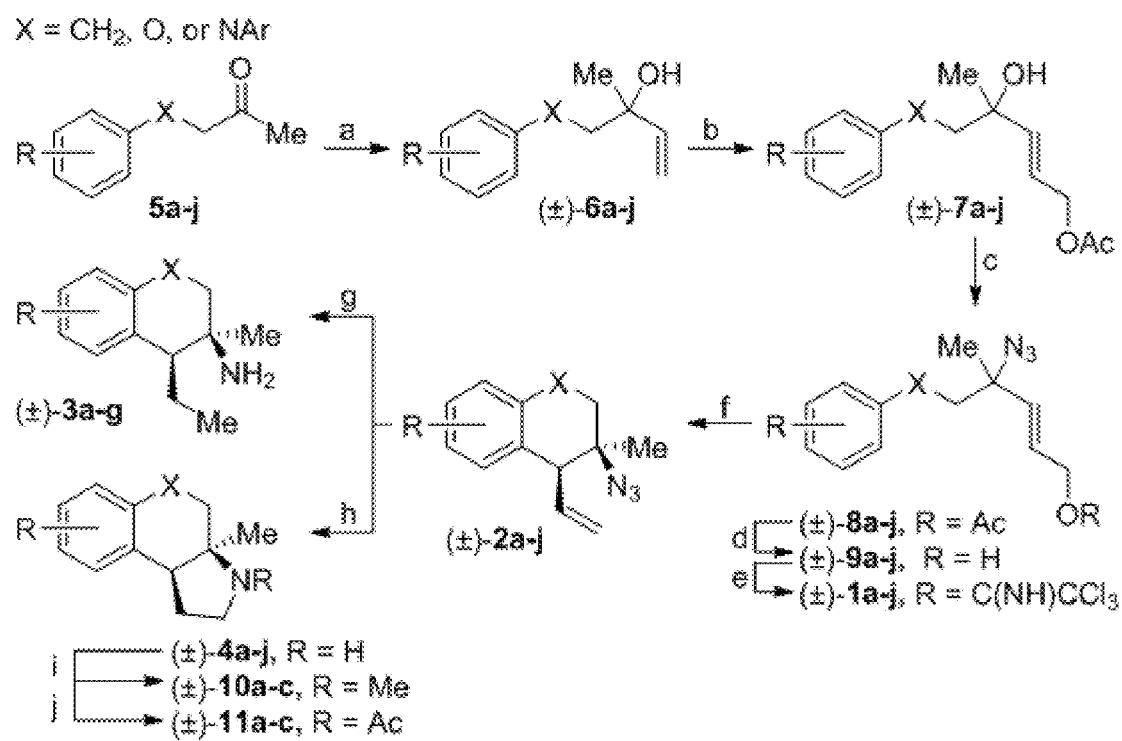
FIG. 3 is a reaction scheme showing the synthesis of (±)-GCPR ligands of the present disclosure (Reagents and conditions: (a) vinyl MgCl, THF, 0° C., 30 min 83%-91%; (b) cis-1,4-diacetoxy-2-butene, 1-2 mol % Hoveyda-Grubbs 2nd generation catalyst, 40° C., 18 h, 68%-86%; (c) TMSN$_3$, 10 mol % Zn(OTf)$_2$, rt, 90 min, 29%-87%; (d) K$_2$CO$_3$, MeOH, rt, 30 min, 97%-quant.; (e) NCCCl$_3$, 20 mol % DBU, rt, 90 min, 73%-97%; (f) 10 mol % AgSbF$_6$, CHCl$_3$, 40-60° C., 24 h, 39%-94%; (g) H$_2$, 10% w/w Pd/C, MeOH, 18 h, 92%-quant; (h) HBCy$_2$, DCM, 0° C. to rt, 18 h, 35%-76%; (i) aq. CH$_2$O, NaBH$_3$CN, HOAc, NCCH$_3$, 0° C. to rt, 30 min, 70%-89%; (j) Ac$_2$O, TEA, DMAP, 0° C. to rt, 18 h 73%-96%), according to one or more embodiments of the present disclosure.

In some embodiments, the synthesis of the compounds of formulas (I) and/or (II), which include GPCR ligands, can proceed with the addition of vinyl Grignard to ketone 5, forming tertiary allylic alcohol 6 (FIG. 3). The structures for each of the compounds referred to in this paragraph can be determined with reference to FIG. 3. Subsequent cross metathesis with cis-1,4-but-2-enediol diacetate and Hoveyda-Grubbs $2^{nd}$ generation catalyst can afford allylic acetate 7. Azidation can proceed upon exposure to TMSN$_3$ and catalytic Zn(OTf)$_2$ to generate allylic azide 8 as a mixture of equilibrating isomers. Methanolysis can cleave the acetate and the resulting alcohol 9 can be activated as the trichloroacetimidate 1. The dynamic cyclization can be performed with catalytic AgSbF$_6$ yielding tertiary azide 2, typically in >25:1 dr. Global reduction with H$_2$ and palladium on carbon can yield primary amine 3. Alternatively, exposure to HBCy$_2$ resulted in pyrrolidine 4. The pyrrolidine can be subjected to N-methylation (10) or acetylation (11).

Figure 4:
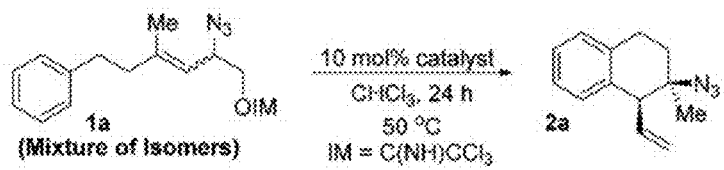
FIG. 4 presents Table A summarizing the optimization of the tandem rearrangement Friedel-Crafts alkylation reaction (0.10 mmol substrate at 0.1 M in CHCl$_3$ for 24 h. [b]Determined by GC-FID analysis using naphthalene as an internal standard. Values are the average of duplicate trials. [c]Determined by GC-FID analysis. [d]20 mol % 2,6-di-tert-butyl-4-methylpyridine was added. nd=not determined. [e]The reaction was conducted in CHCl$_3$ stabilized with EtOH. [f]5 equiv of water were deliberately added. [g]The reaction was conducted under ambient conditions), according to one or more embodiments of the present disclosure.
Figure 5:
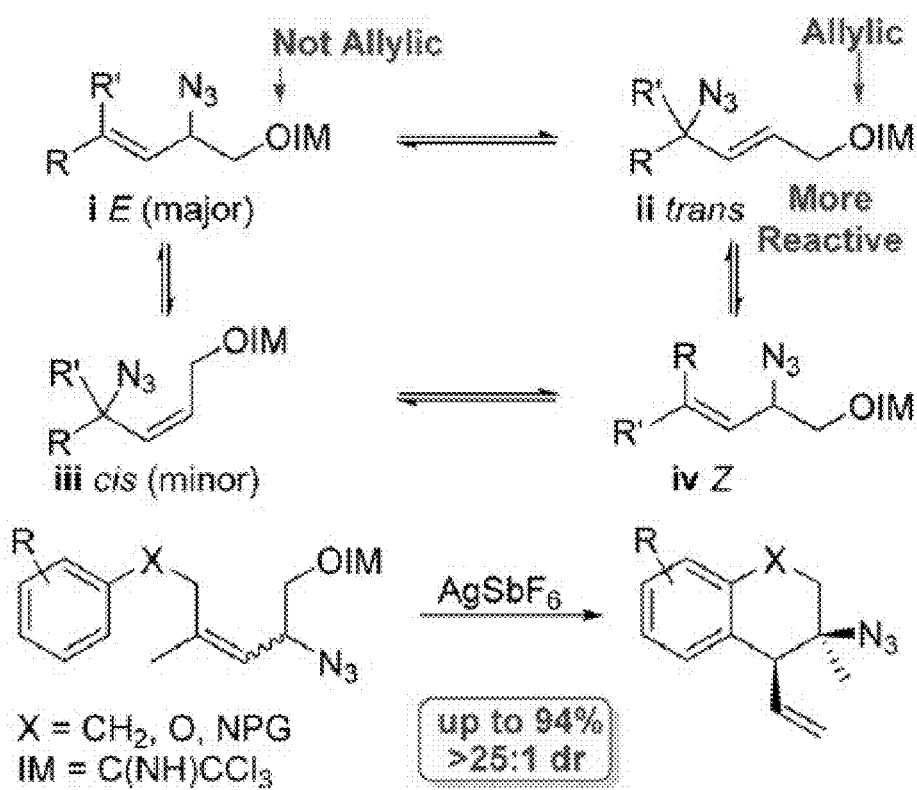
FIG. 5 illustrates the tandem rearrangement Friedel-Crafts alkylation reaction used to achieve selectivity for allylic azide functionalization, according to one or more embodiments of the present disclosure.

In some embodiments, the synthesis can proceed with allylic azide 1a (See FIG. 4 which shows Table A—Optimization of Tandem Rearrangement Friedel-Crafts Alkylation). The structures for each of the compounds referred to in this paragraph can be determined with reference to FIGS. 4-5. This allylic azide can exist as an equilibrium mixture (1.3:1.0:0.7:trace E:trans:Z:cis, representations shown in FIG. 5). In some embodiments, the reactive trans isomer is only 30% of the mixture. The azide 1a can be exposed to a number of activators, including Lewis acids (entries 1-3), Brønsted acids (entries 4-7), and transition metal complexes (entries 8-10). Silver salts with noncoordinating counterions can be efficacious (entries 12-14) and those with more lipophilic counterions can provide superior results. Conditions with catalytic AgSbF$_6$ can be mild, high yielding, and highly stereoselective (entry 14). In some embodiments, compounds such as 2,6-di-tert-buty-4-methyl-pyridine can inhibit the reaction (entry 15). The reaction can be slow in ethanol stabilized chloroform (entry 16) or in the presence of deliberately added water (entry 17). Accordingly, in some embodiments, general acid catalysts can be employed. The reaction can be tolerant to ambient conditions (entry 18).

The reaction can proceed with a series of allylic azides (Scheme 1). Common substituents on the aryl ring can be tolerated (H, OMe, Cl, or Br, 2a-2d). The structures for each of the compounds referred to in this paragraph can be determined with reference to Scheme 1. Conveniently, derivative 2d can provide diffraction quality crystals. Analysis can unambiguously demonstrate the relative configuration of 2d. Other compounds can be assigned by analogy to compound 2d. Different tethers can be tolerated. In some embodiments, the 3-methyl group is not required for diastereoselectivity (2e). Azide 2e can be mapped onto biologically active 3-amino-tetralins. The imidate 1f can exist almost exclusively as the unreactive isomers (e.g., as confirmed by $^1$H NMR analysis (>99% E and Z)). The reactive trans isomer can be destabilized by syn-pentane interactions with the geminal methyl groups. In some embodiments, this will not inhibit reactivity and compound 2f can be isolated in acceptable yield. This can support Curtin-Hammett kinetics with rate limiting aromatic substitution. Moving the methyl group to the center of the allylic system can erode the dr (1.7:1 for compound 2g). A putative stereochemical model based on chair like transition states (Scheme A) was proposed.

Scheme A: Stereochemical Model

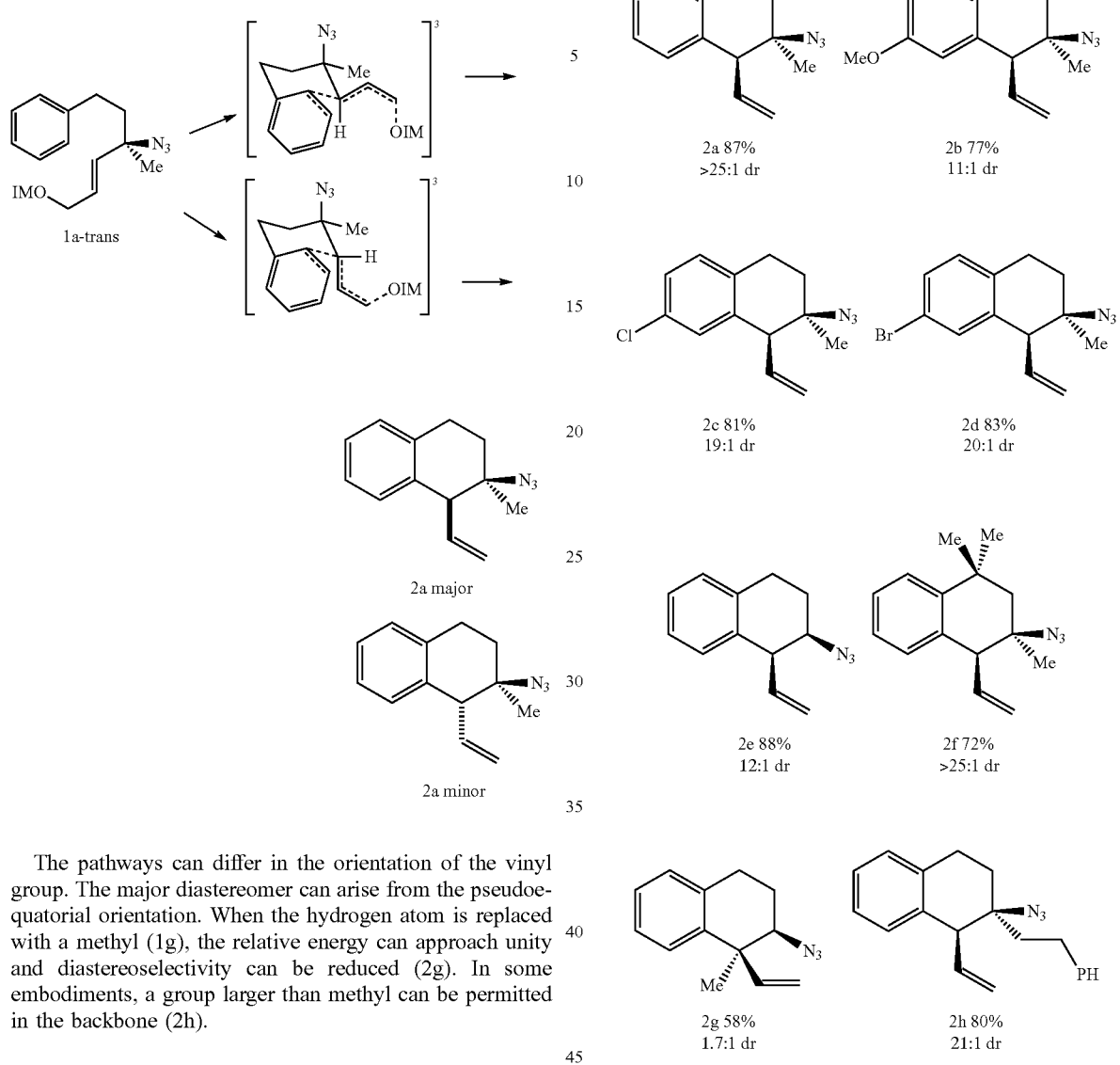

The pathways can differ in the orientation of the vinyl group. The major diastereomer can arise from the pseudoequatorial orientation. When the hydrogen atom is replaced with a methyl (1g), the relative energy can approach unity and diastereoselectivity can be reduced (2g). In some embodiments, a group larger than methyl can be permitted in the backbone (2h).

Scheme 1: Formation of Tetralins 2a-h by Tandem Process[a]

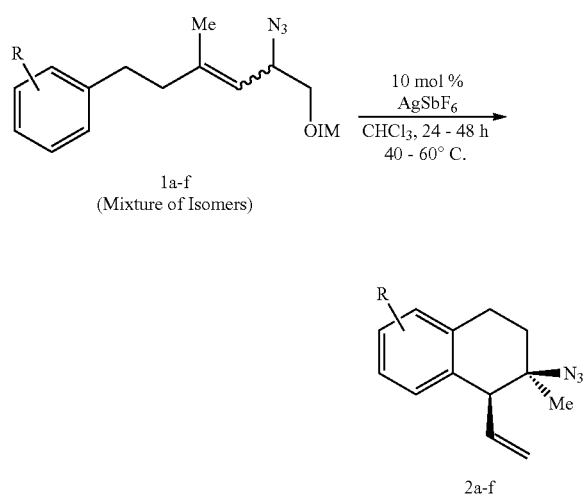

IM = C(NH)CCl$_3$
[a]Yields reported for isolated material as the average of duplicate trials. The dr was determined by $^1$H NMR.

In some embodiments, a heteroatom can be incorporated into the system to generate valuable heterocycles. A number of ethereal allylic azides can be converted into chromanes in high yield and selectivity (Scheme 2, 4a). The structures for each of the compounds referred to in this paragraph can be determined with reference to Scheme 2. Activating groups such as methyl (4b) or methoxy (4c) can be competent and so can compounds with a halogen substituent (entries 4d-4f). Poly substituted aromatics can be tolerated (entries 4g-4i). In some embodiments, the heteroatom is a basic site that can slow catalysis, where the proximal oxygen can inductively reduce the stability of a cationic intermediate and disrupt the azide equilibrium. For example, the formation of 4j can be slow and imidate decomposition can occur. In some embodiments, chromane 4k can be isolated as a mixture of regioisomers (1.4:1).

Scheme 2: Formation of Chromanes 4a-1 by Tandem Process[a]

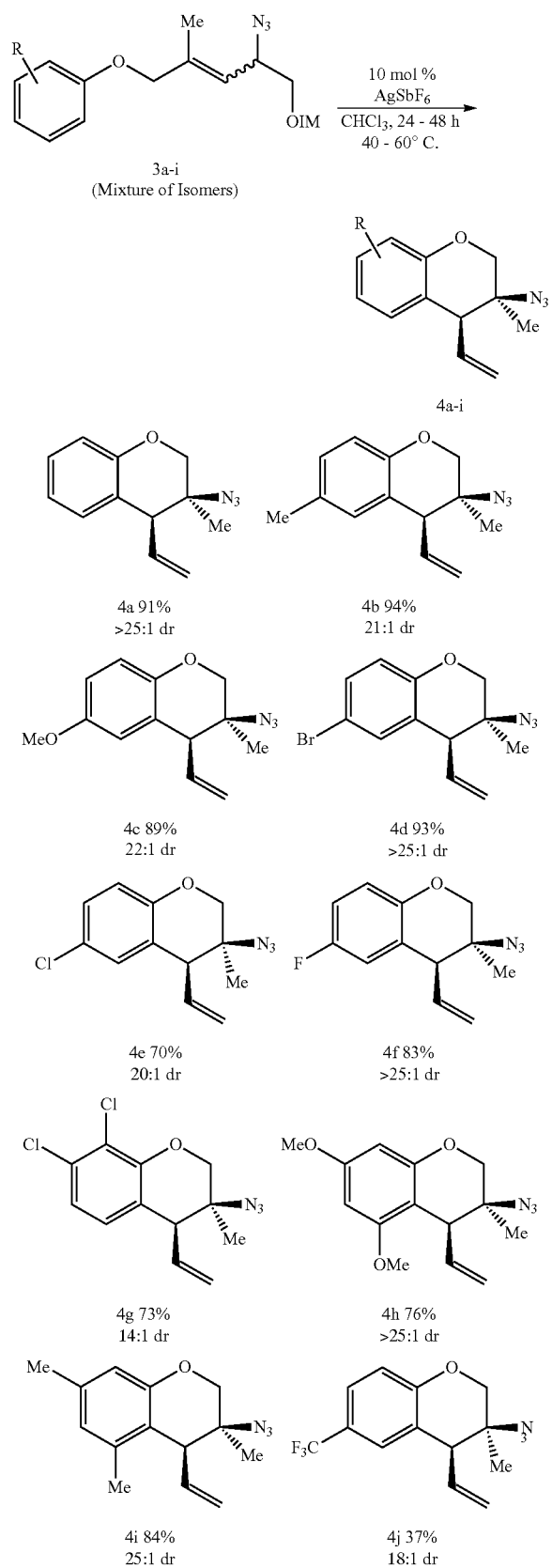

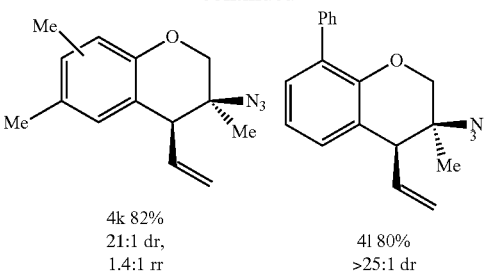

4k 82%
21:1 dr,
1.4:1 rr 4l 80%
>25:1 dr

IM = C(NH)CCl$_3$
[a]Yields reported for isolated material as the average of duplicate trials. The dr was determined by $^1$H NMR.

In some embodiments, aniline derived allylic azides can lead to azido-tetrahydroquinolines (Scheme 3). Several azides can be prepared with varying arene substitution and N-protecting group. In some embodiments, all imidate precursors in this class can contain less than 10% of the reactive trans isomer at equilibrium. These azides can readily afford tetrahydroquinolines in good yield with high dr. A number of aryl-substituents can be tolerated (entries 6a-6f). The structures for each of the compounds referred to in this paragraph can be determined with reference to Scheme 3.

Scheme 3: Formation of Tetrahydroquinolines 6a-f[a]

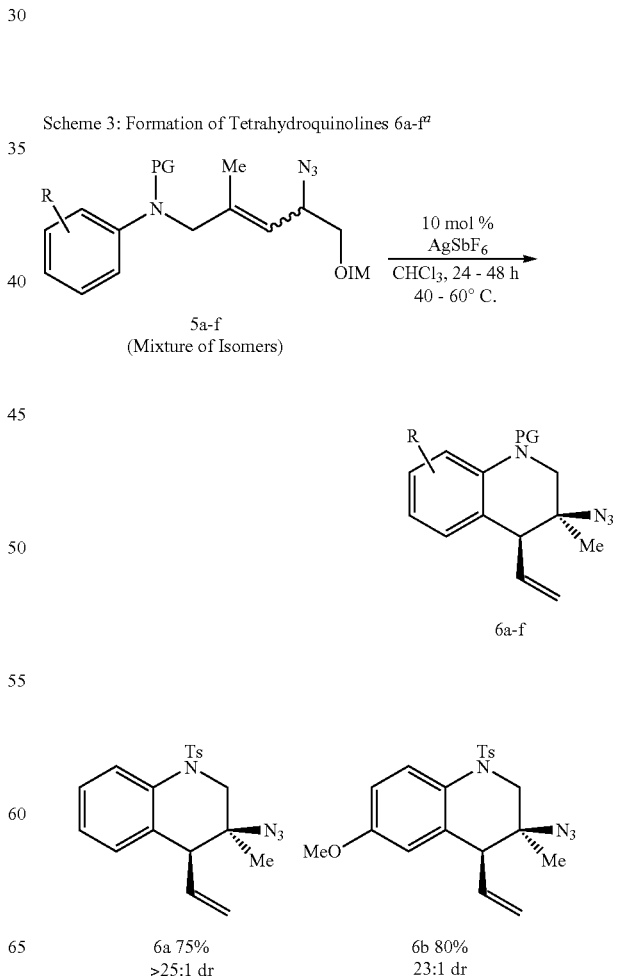

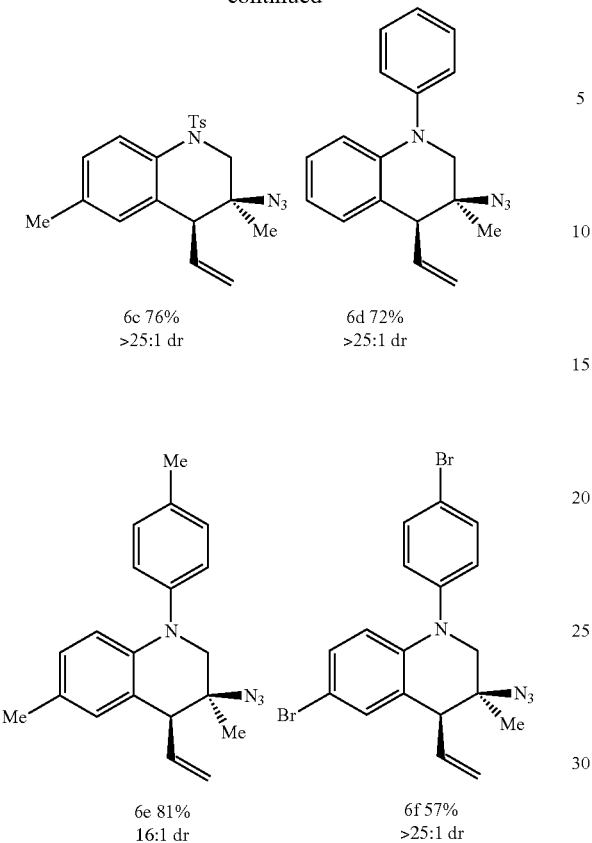

6c 76%
>25:1 dr 6d 72%
>25:1 dr 6e 81%
16:1 dr 6f 57%
>25:1 dr

IM = C(NH)CCl₃
[a]Yields reported for isolated material as the average of duplicate trials. The dr was determined by ¹H NMR.

In some embodiments, the reaction is conducted on a gram scale (Scheme 4). Using >1 g of imidate 1a can provide tetralin 2a in 82% yield. The structures for each of the compounds referred to in this paragraph can be determined with reference to Scheme 4. The product can be oxidized under the Upjohn protocol to afford diol 7. Reduction using palladium on carbon can provide amine 8. Selective reduction of the azide with LiAlH₄ can afford amine 9. The protocol of Evans can be used to form pyrrolidine 10. Cycloaddition can provide triazole 11.

Scheme 4: Gram Scale Reaction and Diversification of Product

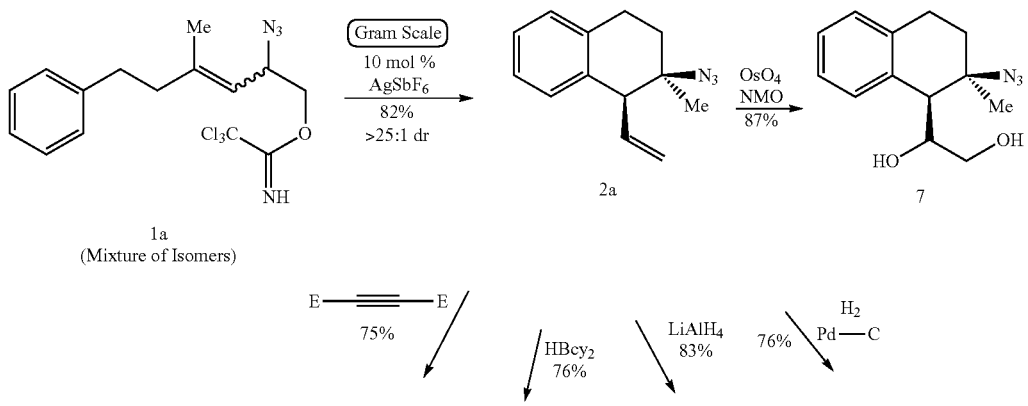

-continued

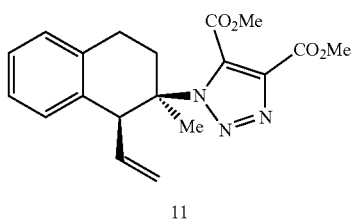
11

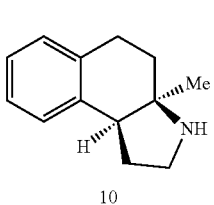
10

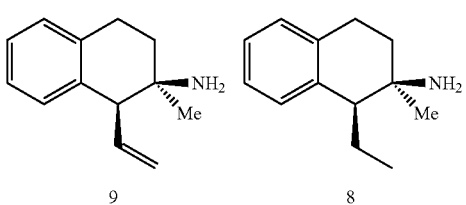
9    8

Biological Data

The phenethylamine backbone is a privileged substructure found in a wide variety of G-protein-coupled receptor (GPCR) ligands. This includes both endogenous neurotransmitters and active pharmaceutical agents. The G-Protein-coupled receptor (GPCR) binding affinity of the compounds of the present disclosure was assessed through the Psychoactive Drug Screening Program. More than twenty structurally unique heterocyclic phenethylamine derivatives were evaluated. Several compounds demonstrated significant and selective binding against GPCRs. For example, selective ligands for the 5-$HT_{2B}$, 5-$HT_7$, and $\sigma_1$ receptors were identified, each with low nanomolar binding affinities. The activity against the $\sigma_1$ receptor was confirmed in a cellular assay. An example of a compound which demonstrated neuroprotective properties when assayed in 661W cells is compound 4e. See FIG. 8 for the structure of compound 4e. This and the ensuing discussion shall not be limiting as any of the compounds of the present disclosure may exhibit selective and/or potent inhibitory effects against GPCR and other central nervous system receptors.

An initial screen of three primary amines was submitted. Compounds (3a), (3b), and (3c) are provided in FIG. 6 which presents Table 1, including the results of the initial GPCR screen, and were submitted as each of those compound represents one of the three synthetically accessible cores: tetralin (3a), chromane (3b), and tetrahydroquinoline (3c). The structures for each of the compounds referred to in this paragraph can be determined with reference to FIG. 6. The molecules were screened across a wide range of human GPCR including serotonin (5-HT), α- and β-adrenergic (Alpha and Beta), dopamine (D), histamine (H), muscarinic (M), opioid (OR), sigma (σ), and others (Table 1). Of the three compounds assayed, all exhibited at least moderate binding ($K_i \leq 200$ nM) against one or more receptors. Tetralin (3a) was the only compound to exhibit any activity against the δ-, μ-, or κ-opioid receptor. This is consistent with the structures of other opioid ligands that contain a hydrocarbon backbone (e.g. morphine). Compound (3a) exhibited moderate inhibitory activity towards the 5-$HT_{2B}$ and $\sigma_1$ receptors. Chromane (3b) exhibited moderate activity against the 5-$HT_{2B}$ receptor, but lacked any κ-opioid binding. Tetrahydroquinoline (3c) exhibited the most potent initial hit, with a $K_i$ of 73 nM against the 5-$HT_{1A}$ receptor. Based on these initial results and lack of opioid activity, a subsequent structure activity relationship study was conducted on the chromane and tetrahydroquinoline scaffolds against the 5-$HT_{1A}$, 5-$HT_{2B}$, 5-$HT_7$, $\sigma_1$ and $\theta_2$ receptors.

Assay results for five additional primary amine analogues are displayed in FIG. 7 which presents Table 2. Amines 3d and 3e did not demonstrate a $K_i$ below 100 nM for any of the GCPR assayed. The structures for each of the compounds referred to in this paragraph can be determined with reference to FIG. 7. Amine 3f bound the $\sigma_1$ receptor with a $K_i$ of 16 nM and demonstrated reasonable selectivity relative to the 5-$HT_{2B}$ receptor (~10 fold), which was the second most sensitive receptor assayed. Amines 3g and 3h where more potent against the 5-$HT_{2B}$ receptor ($K_i$=3.5 nM and 20 nM, respectively). Compound 3g demonstrated ~150 fold selectivity relative to the $\sigma_2$ receptor, which was the second most sensitive GPCR assayed. The 5-$HT_2B$ receptor is a member of the 5-$HT_2$ sub-family of 5-HT receptors that is known to be an essential receptor during development. Long term consumption of 5-$HT_{2B}$ agonists can induce potentially fatal myofibroblast proliferation and valvular heart disease. Thus, the 5-$HT_{2B}$ receptor is considered an antitarget. Therefore, the $\sigma_1$ activity demonstrated by amine 3f on more rigid pyrrolidine analogues was evaluated next.

The σ receptors were initially thought to be members of the opioid receptor family. Since, it has been shown that $\sigma_1$ acts as a chaperone protein localized in the endoplasmic reticulum, and affects a wide variety of cellular functions including regulation of opioid receptors, kinases, TRPV1, dopamine receptors, apotosis, as well as cellular calcium and potassium levels. Modulating intracellular calcium levels implicated $\sigma_1$ as a target for treating colon and breast cancer. Modulating the $\sigma_1$ receptor also effects alcohol abuse, pain management, opioid analgesia, and neuroprotection in models of retinal neural degradation.

Pyrrolidine containing chromanes were assessed for $\sigma_1$ binding (FIG. 8 presenting Table 3). A direct analogue of amine 3f was essentially equipotent against $\sigma_1$ (4a), while replacing the phenyl group with a methoxy group was disadvantageous (4b). The structures for each of the compounds referred to in this paragraph can be determined with reference to FIG. 8. Exploring substitution around the arene provided mixed results. Benzyloxy compound 4c was a potent $\sigma_1$ ligand. Removing the benzyl group was detrimental to activity (4d), although some potency could be restored through N-methylation (10a). Unsurprisingly, masking the basic amine as an acetate removed activity in both cases examined (11a and 11b). Compound 4e could be a lead compound. While compound 4e is less potent than amine 3f as a $\sigma_1$ ligand, it shows >200 fold selectivity vs the $\sigma_2$ receptor. Changing the methoxy groups for methyl groups enhanced 5-$HT_2B$ binding (4f) and the other compounds assayed provided both reduced or potency and selectivity (4g, 4h, 10b, and 11b).

Figure 9:
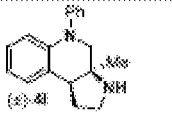
FIG. 9 presents Table 4 summarizing K$_i$ data for tetrahydroquinolines, according to one or more embodiments of the present disclosure.

With an attempt to evaluate the 5-$HT_{1A}$ activity demonstrated by amine 3c, other tetrahydroquinolines were investigated (FIG. 9 presenting Table 4). As a direct comparison to amine 3c (FIG. 6 presenting Table 1), pyrrolidine 4i (FIG. 9 presenting Table 4) was assayed. The structures for each of the compounds referred to in this paragraph can be determined with reference to FIGS. 6 and 9. While primary amine 3c was ~15 fold selective for 5-$HT_{1A}$ over 5-$HT_7$, pyrrolidine 4i was not a suitable ligand for 5-$HT_{1A}$ ($K_i$>10,000 nM) and was instead a potent 5-$HT_7$ ligand ($K_i$=6.3 nM). Therefore, the relatively small structural change resulted in more than a 20,000 fold relative difference in the 5-HT$_{1A}$ vs 5-HT$_7$ selectivity. The 5-HT$_7$ receptor has been implicated in the regulation of multiple biological functions including sleep, circadian rhythm, and mood. Various 5-HT$_7$ antagonists have been investigated for depression treatment along with other disorders. The 5-HT$_7$ potency could be further enhanced though N-methylation (10c) and acylation removed activity (11c). Other substituted arenes displayed reduced 5-HT$_7$ activity (4j and 4k). Even though compound 4i was less potent than compound 10c, compound 4i was selected for further assay because it exhibited enhanced selectivity, being ~75-fold less potent against the next most sensitive receptor, σ$_1$.

Figure 10:
FIG. 10 presents Table 5 summarizing K$_i$ data of a broad GPCR screen, according to one or more embodiments of the present disclosure.
Figure 12A:
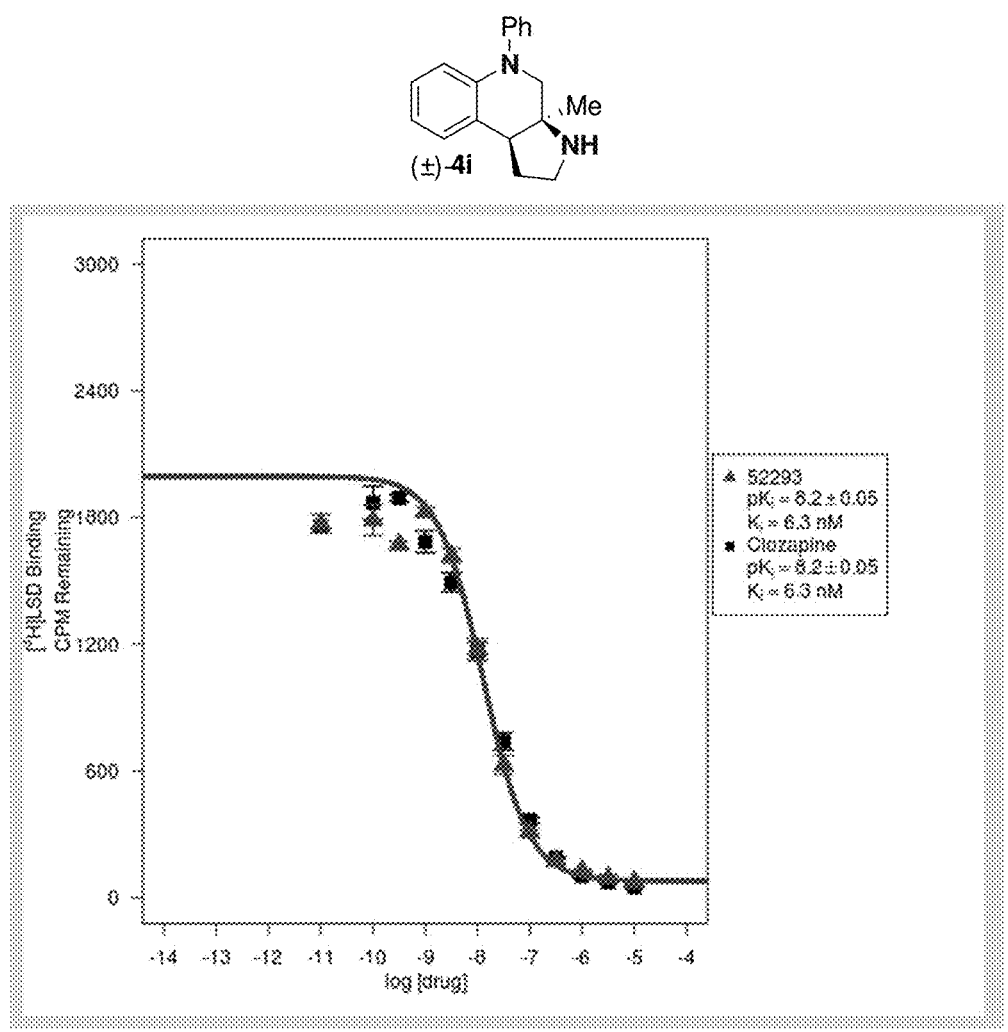
Figure 13B:
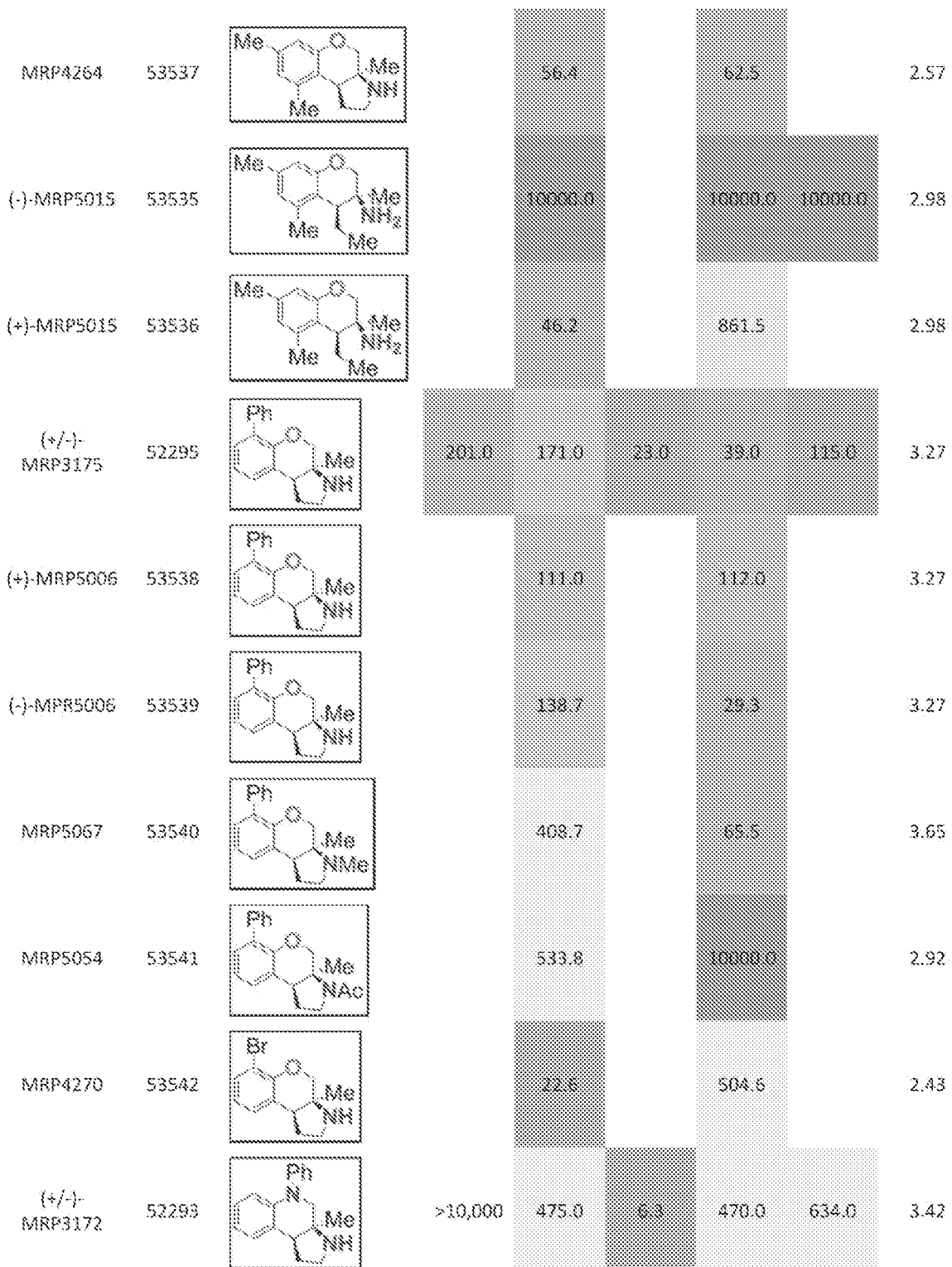
Figure 13E:
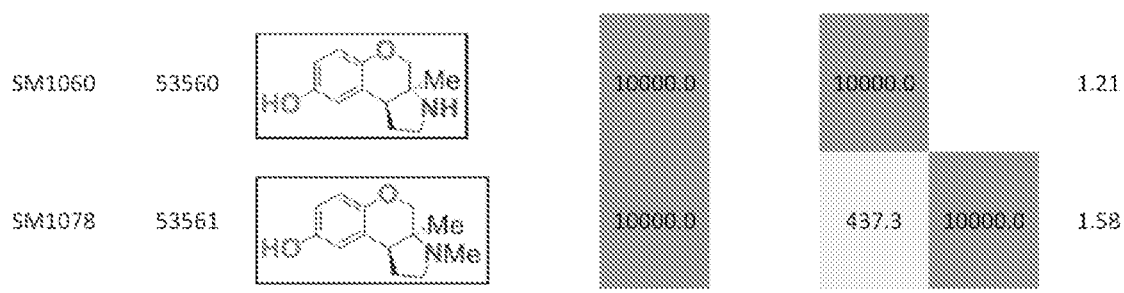

Based on the results outlined in Tables 1-4, compounds 4e and 4i were screened more broadly against a wider array of GCPR (FIG. 10 presenting Table 5). The structures for each of the compounds referred to in this paragraph can be determined with reference to FIGS. 10-12. Gratifyingly, only minimal activity was observed across the additional GCPR that were investigated. This indicates that compound 4i could be considered a new lead targeting 5-HT$_7$ due to the low nM binding affinity (K$_i$=6.3 nM) and selectivity (~75 fold vs next most potent receptor). Compound 4e could be considered a new lead targeting or due to its respectable potency (K$_i$=44 nM), good σ$_1$ vs σ$_2$ selectivity (>200 fold), and good selectivity vs other GCPR (>5 fold vs 5-HT$_2$B). See FIGS. 11-12. To further investigate or receptor activity, the neuroprotective effects of compound 4e was assayed against 661W retinal under oxidative stress. The or receptor is a target for protecting retinal cells from neural degradation.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

EXAMPLES

Example 1

General Procedure 1: Palladium Catalyzed Hydrogenation

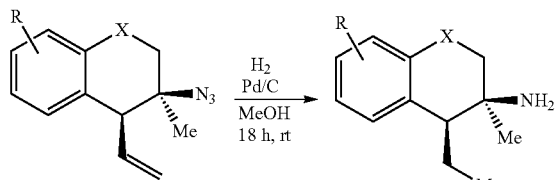

(Example given for R = o-Ph, X = O)

An oven dried 4 mL vial was charged with palladium on carbon (3 mg, 10 w % Pd) and sealed with a septa cap. The vial was then flushed with nitrogen gas (approx. 0.5 L) and charged with a solution of azide MRP4172 (31.3 mg, 0.11 mmol) in MeOH (1 mL). The head space of the vial was then flushed with hydrogen gas (approx. 1 L). The vial was fitted with 2 balloons of hydrogen gas and stirred vigorously. After 18h, the reaction was diluted with MeOH and filtered through a short plug of silica gel. The filtrate was concentrated under reduced pressure to afford MRP4233 (26.5 mg, 0.10 mmol, 92%) as a clear oil.

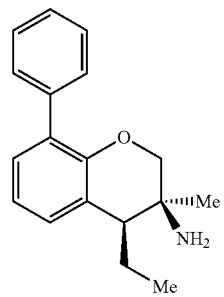

MRP4233

MRP4233: $^1$H NMR (500 MHz, CDCl$_3$) δ 7.55 (dd, J=8.5, 1.4 Hz, 2H), 7.42 (t, J=7.6 Hz, 2H), 7.33 (tt, J=7.3, 1.6 Hz, 1H), 7.19 (dd, J=7.5, 1.8 Hz, 1H), 7.11 (dd, J=7.6, 1.8 Hz, 1H), 6.95 (t, J=7.6 Hz, 1H), 3.96 (d, J=10.5 Hz, 1H), 3.76 (dd, J=10.5, 1.7 Hz, 1H), 2.50 (ddd, J=8.7, 3.9, 1.4 Hz, 1H), 2.02 (br s, 2H), 1.99 (dqd, J=15.0, 7.5, 4.0 Hz, 1H), 1.55-1.45 (m, 1H), 1.22 (s, 3H), 1.12 (t, J=7.5 Hz, 3H); $^{13}$C NMR (126 MHz, CDCl$_3$) δ 149.5, 138.9, 130.0, 129.74, 129.70, 129.3, 128.1, 127.0, 125.8, 120.0, 73.0, 48.9, 48.5, 26.6, 25.2, 13.9; IR (NaCl, thin film, cm$^{-1}$) 3365, 3056, 3028, 2961, 2930, 2873, 1587, 1467, 1456, 1430, 1210, 1024, 758, 699; HRMS (ESI-TOF) m/z calcd for C$_{18}$H$_{22}$NO$^+$ (M+H)$^+$268.1696, found 268.1693; calcd for C$_{18}$H$_{19}$O$^+$ (M-NH$_2$)$^+$ 251.1430, found 251.1429.

Example 2

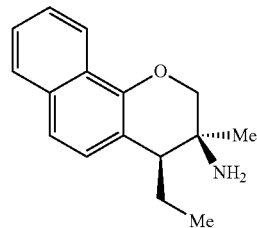

MRP4234

MRP4234: General procedure 1 was used and the product was isolated in quantitative yield as a clear oil: $^1$H NMR (500 MHz, CDCl$_3$) δ 8.22-8.16 (m, 1H), 7.79-7.73 (m, 1H), 7.49-7.43 (m, 2H), 7.37 (d, J=8.4 Hz, 1H), 7.21 (d, J=8.5 Hz, 1H), 4.10 (d, J=10.4 Hz, 1H), 3.93 (dd, J=10.4, 1.7 Hz, 1H), 2.57 (ddd, J=8.1, 4.4, 1.6 Hz, 1H), 2.01 (dqd, J=15.1, 7.5, 4.4 Hz, 1H), 1.74 (br s, 2H), 1.60-1.49 (m, 1H), 1.23 (s, 3H), 1.12 (t, J=7.5 Hz, 3H); $^{13}$C NMR (126 MHz, CDCl$_3$) δ 147.5, 133.5, 128.6, 127.4, 126.0, 125.3, 125.0, 122.0, 119.5, 119.0, 73.2, 49.1, 48.0, 26.7, 25.7, 14.0; IR (NaCl, thin film, cm$^{-1}$) 3369, 3053, 2961, 2930, 2874, 1575, 1401, 1378, 1107, 1092, 1011, 805, 746; HRMS (ESI-TOF) m/z calcd for C$_{16}$H$_{20}$NO$^+$ (M+H)$^+$ 242.1539, found 242.1543; calcd for C$_{16}$H$_{17}$O$^+$ (M-NH$_2$)+ 225.1274, found 225.1281.

Example 3

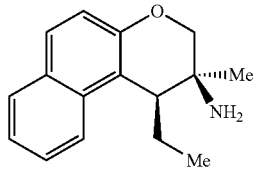
MRP4235

MRP4235: General procedure 1 was used and the product was isolated in 91% as a clear oil: $^1$H NMR (500 MHz, CDCl$_3$) δ 7.85 (d, J=8.5 Hz, 1H), 7.78 (dd, J=8.1, 1.3 Hz, 1H), 7.63 (d, J=8.9 Hz, 1H), 7.50 (ddd, J=8.4, 6.8, 1.4 Hz, 1H), 7.35 (ddd, J=8.0, 6.8, 1.1 Hz, 1H), 7.04 (d, J=8.9 Hz, 1H), 4.07 (d, J=10.4 Hz, 1H), 3.77 (dd, J=10.4, 1.9 Hz, 1H), 3.03 (ddd, J=6.5, 4.1, 1.9 Hz, 1H), 1.84 (dp, J=14.5, 7.3 Hz, 1H), 1.69 (dqd, J=15.1, 7.7, 4.0 Hz, 1H), 1.40 (br s, 2H), 1.19 (s, 3H), 1.17 (t, J=7.5 Hz, 3H); $^{13}$C NMR (126 MHz, CDCl$_3$) δ 149.5, 133.3, 129.6, 128.9, 128.3, 126.4, 123.2, 122.5, 118.7, 118.5, 71.7, 49.3, 44.2, 27.9, 27.5, 15.6; IR (NaCl, thin film, cm$^{-1}$) 3370, 3055, 2959, 2928, 2874, 1622, 1599, 1514, 1472, 1401, 1229, 1082, 1026, 812, 748; HRMS (ESI-TOF) m/z calcd for C$_{16}$H$_{20}$NO$^+$ (M+H)$^+$ 242.1539, found 242.1544; calcd for C$_{16}$H$_{17}$O$^+$ (M-NH$_2$)$^+$ 225.1274, found 225.1273.

Example 4

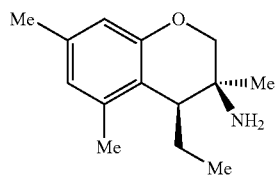
MRP4261

MRP4261: General procedure 1 was used and the product was isolated in quantitative yield as a clear oil: $^1$H NMR (500 MHz, CDCl$_3$) δ 6.59 (s, 1H), 6.49 (s, 1H), 3.93 (d, J=10.4 Hz, 1H), 3.66 (dd, J=10.4, 2.0 Hz, 1H), 2.47 (ddd, J=6.5, 4.3, 1.9 Hz, 1H), 2.25 (s, 3H), 2.24 (s, 3H), 1.70 (dp, J=14.4, 7.2 Hz, 1H), 1.49-1.38 (m, 3H), 1.12 (s, 3H), 1.11 (t, J=7.6 Hz, 3H); $^{13}$C NMR (126 MHz, CDCl$_3$) δ 151.9, 137.3, 136.7, 123.6, 122.9, 114.5, 71.5, 49.7, 45.4, 27.7, 27.2, 21.0, 19.4, 15.2; IR (NaCl, thin film, cm$^{-1}$) 3365, 2959, 2926, 2875, 1618, 1577, 1455, 1310, 1290, 1225, 1139, 1074, 839; HRMS (ESI-TOF) m/z calcd for C$_{14}$H$_{22}$NO$^+$ (M+H)$^+$ 220.1696, found 220.1695; calcd for C$_{14}$H$_{19}$O$^+$ (M-NH$_2$)$^+$ 203.1430, found 203.1427.

Example 5

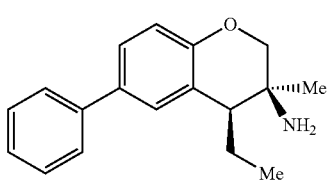
MRP5063

MRP5063: General procedure 7 was used and the product was isolated in quantitative yield as a clear oil: $^1$H NMR (400 MHz, CDCl$_3$) δ 7.58-7.53 (m, 2H), 7.46-7.40 (m, 2H), 7.38 (dd, J=8.4, 2.3 Hz, 1H), 7.35-7.28 (m, 2H), 6.90 (d, J=8.4 Hz, 1H), 4.01 (d, J=10.5 Hz, 1H), 3.79 (dd, J=10.5, 1.5 Hz, 1H), 2.50 (dd, J=8.8, 3.9 Hz, 1H), 2.18 (br s, 2H), 2.01 (dqd, J=18.9, 7.5, 3.5 Hz, 1H), 1.54-1.45 (m, 1H), 1.24 (s, 3H), 1.14 (t, J=7.4 Hz, 3H); $^{13}$C NMR (126 MHz, CDCl$_3$) δ 152.3, 141.2, 133.3, 129.2, 128.9, 126.9, 126.7, 126.6, 125.4, 116.9, 72.8, 49.3, 48.1, 26.4, 24.9, 13.8; IR (NaCl, thin film, cm$^{-1}$) 3367, 3030, 2962, 2930, 2874, 1613, 1483, 1232, 1130, 1019, 825, 763, 698; HRMS (ESI-TOF) m/z calcd for C$_{18}$H$_{22}$NO$^+$ (M+H)$^+$ 268.1696, found 268.1686; calcd for C$_{18}$H$_{19}$O$^+$ (M-NH$_2$)$^+$ 251.1430, found 251.1431.

Example 6

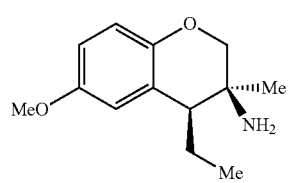
MRP5064

MRP5064: General procedure 7 was used and the product was isolated in quantitative yield as a clear oil: $^1$H NMR (400 MHz, CDCl$_3$) δ 6.79-6.59 (m, 3H), 3.88 (d, J=10.5 Hz, 1H), 3.76 (s, 3H), 3.68 (d, J=10.4 Hz, 1H), 2.38 (dd, J=8.5, 3.9 Hz, 1H), 1.93 (dqd, J=14.9, 7.6, 4.1 Hz, 1H), 1.53-1.39 (m, 3H), 1.17 (s, 3H), 1.09 (t, J=7.5 Hz, 3H); $^{13}$C NMR (101 MHz, CDCl$_3$) δ 153.2, 146.7, 126.2, 116.8, 115.4, 113.3, 73.3, 55.9, 49.0, 48.2, 26.5, 24.8, 14.1; IR (NaCl, thin film, cm$^{-1}$) 3369, 2960, 2874, 2832, 1496, 1209, 1050, 814; HRMS (ESI-TOF) m/z calcd for C$_{13}$H$_{20}$NO$_2^+$ (M+H)$^+$ 222.1489, found 222.1487; calcd for C$_{13}$H$_{17}$O$_2^+$ (M-NH$_2$)$^+$ 205.1223, found 205.1227.

Example 7

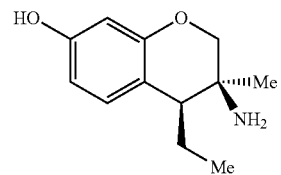
MRP5077

MRP5077: General procedure 7 was used and the product was isolated in quantitative yield as a clear oil: $^1$H NMR (500 MHz, CD$_3$OD) δ 6.88 (d, J=8.4 Hz, 1H), 6.33 (dd, J=8.3, 2.5 Hz, 1H), 6.22 (d, J=2.5 Hz, 1H), 3.92 (d, J=10.5 Hz, 1H), 3.66 (dd, J=10.5, 1.7 Hz, 1H), 2.30 (ddd, J=9.3, 3.6, 1.4 Hz, 1H), 1.90 (dqd, J=15.0, 7.5, 3.9 Hz, 1H), 1.35-1.24 (m, 1H), 1.12 (s, 3H), 1.02 (t, J=7.5 Hz, 3H); $^{13}$C NMR (126 MHz, CD$_3$OD) δ 156.7, 153.1, 130.8, 116.0, 107.2, 102.2, 71.4, 48.5, 47.1, 24.7, 24.6, 12.1; IR (NaCl, thin film cm$^{-1}$) 3421, 2963, 2932, 1620, 1504, 1467, 1159, 1120, 633; HRMS (ESI-TOF) m/z calcd for C$_{12}$H$_{18}$NO$_2^+$ (M+H)$^+$ 208.1332, found 208.1331; calcd for C$_{12}$H$_{15}$O$_2^+$ (M-NH$_2$)$^+$ 191.1067, found 191.1064.

Example 8

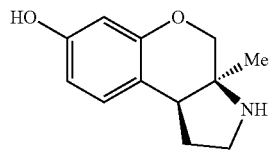

MRP5086

MRP5086: MRP5069 was used as the starting material. General procedure 7 was used and the product was isolated in quantitative yield as a clear oil: $^1$H NMR (500 MHz, CD$_3$OD) δ 7.01 (d, J=8.3 Hz, 1H), 6.46 (dd, J=8.4, 2.4 Hz, 1H), 6.31 (d, J=2.4 Hz, 1H), 3.92 (d, J=11.4 Hz, 1H), 3.78 (d, J=11.3 Hz, 1H), 3.19 (dt, J=11.2, 7.2 Hz, 1H), 3.04 (t, J=6.8 Hz, 1H), 3.02-2.97 (m, 1H), 2.56 (dq, J=14.1, 7.3 Hz, 1H), 1.94-1.86 (m, 1H), 1.34 (s, 3H); $^{13}$C NMR (126 MHz, CD$_3$OD) δ 156.7, 154.3, 130.0, 115.4, 109.6, 102.8, 69.3, 60.6, 44.2, 43.6, 34.3, 21.3; IR (NaCl, thin film, cm$^{-1}$) 3300, 2964, 1621, 1593, 1505, 1471, 1384, 1252, 1158, 1107, 1037, 843, 735; HRMS (ESI-TOF) m/z calcd for C$_{12}$H$_{16}$NO$_2$$^+$ (M+H)$^+$ 206.1176, found 206.1171.

Example 9

General Procedure 2: Pyrrolidine Synthesis

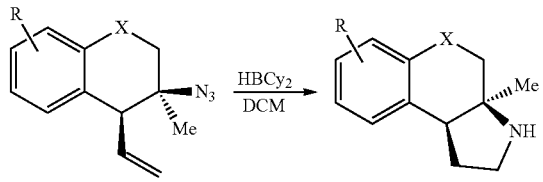

(Example given for R = 1-Naphthyl, X = O)

In a glovebox, a 4 mL vial was charged with HBCy$_2$ (36 mg, 0.2 mmol). The vial was sealed with a septa cap and removed from the glovebox. The vial was then placed in an ice bath and charged with DCM (0.5 mL). A solution of azide MRP4226 in DCM (29 mg, 0.1 mmol, 0.2 M) was added at 0° C. and a rinsed with additional DCM (0.2 mL). After 5 min, the ice bath was removed, and the solution was allowed to gradually warm to room temperature. After 18 h, the reaction was quenched by the addition of solid sodium fluoride (80 mg, 4.0 mmol) and DI water (36 μL, 2.0 mmol). After 1 h, the solution was filtered through a short plug of silica gel rinsed with 2% NEt$_3$ in DCM and concentrated under reduced pressure. Final purification by column chromatography (0 to 70% gradient, i-PrOH in 99:1 hexanes: NEt$_3$) afford pyrrolidine MRP4252 (15 mg, 0.12 mmol, 52%) as a clear oil.

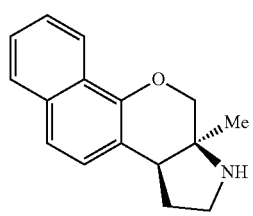

MRP4252

MRP4252: $^1$H NMR (500 MHz, CDCl$_3$) δ 8.23-8.19 (m, 1H), 7.79-7.75 (m, 1H), 7.50-7.44 (m, 2H), 7.43 (d, J=8.4 Hz, 1H), 7.23 (d, J=8.4 Hz, 1H), 3.95 (d, J=10.8 Hz, 1H), 3.93 (d, J=11.0 Hz, 1H), 3.15 (dt, J=10.5, 7.6 Hz, 1H), 3.05-2.99 (m, 1H), 3.01 (t, J=7.5 Hz, 1H), 2.57 (dtd, J=12.6, 7.8, 4.7 Hz, 1H), 1.97 (br s, 1H), 1.93 (dq, J=12.8, 7.6 Hz, 1H), 1.31 (s, 3H); $^{13}$C NMR (126 MHz, CDCl$_3$) δ 148.8, 133.2, 127.8, 127.5, 126.1, 125.6, 125.3, 122.0, 120.9, 119.9, 71.9, 58.2, 46.0, 44.8, 35.8, 24.5; IR (NaCl, thin film, cm$^{-1}$) 3327, 3052, 2962, 2926, 2873, 1576, 1467, 1397, 1375, 1097, 807; HRMS (ESI-TOF) m/z calcd for C$_{16}$H$_{18}$NO$^+$ (M+H)$^+$ 240.1383, found 240.1386.

Example 10

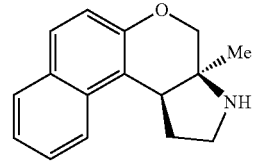

MRP4253

MRP4253: General procedure 8 was used and the product was isolated in 36% yield as a clear oil: $^1$H NMR (500 MHz, CDCl$_3$) δ 7.88 (dd, J=8.5, 1.0 Hz, 1H), 7.80 (dd, J=8.1, 1.3 Hz, 1H), 7.65 (d, J=8.8 Hz, 1H), 7.51 (ddd, J=8.4, 6.8, 1.4 Hz, 1H), 7.37 (ddd, J=8.0, 6.8, 1.1 Hz, 1H), 7.11 (d, J=8.9 Hz, 1H), 3.95 (d, J=10.7 Hz, 1H), 3.80 (dd, J=10.7, 1.2 Hz, 1H), 3.31 (br t, J=8.3 Hz, 1H), 3.24 (dt, J=10.9, 7.9 Hz, 1H), 3.08 (ddd, J=10.9, 8.6, 4.4 Hz, 1H), 2.85 (dtd, J=12.8, 8.3, 4.4 Hz, 1H), 2.20 (br s, 1H), 1.88 (dq, J=13.1, 8.2 Hz, 1H), 1.33 (s, 3H); $^{13}$C NMR (126 MHz, CDCl$_3$) δ 151.0, 133.5, 129.9, 128.8, 128.2, 126.5, 123.6, 123.0, 119.0, 118.1, 70.9, 58.3, 44.7, 43.5, 35.5, 24.0; IR (NaCl, thin film, cm$^{-1}$) 3301, 3060, 2963, 2925, 2875, 1621, 1598, 1513, 1470, 1397, 1229, 1090, 1040, 1020, 814, 748; HRMS (ESI-TOF) m/z calcd for C$_{16}$H$_{18}$NO$^+$ (M+H)$^+$ 240.1383, found 240.1384.

Example 11

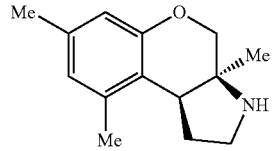

MRP4264

MRP4264: General procedure 8 was used and the product was isolated in 35% yield as a clear oil: $^1$H NMR (500 MHz, CDCl$_3$) δ 6.64 (s, 1H), 6.58 (s, 1H), 3.76 (d, J=10.7 Hz, 1H), 3.65 (dd, J=10.7, 1.2 Hz, 1H), 3.12 (dt, J=10.8, 8.0 Hz, 1H), 3.04 (ddd, J=10.7, 8.5, 3.9 Hz, 1H), 2.79 (br t, J=8.6 Hz, 1H), 2.59 (dtd, J=12.3, 8.1, 3.9 Hz, 1H), 2.27 (s, 3H), 2.26 (s, 3H), 2.11 (br s, 1H), 1.68 (dq, J=12.8, 8.5 Hz, 1H), 1.24 (s, 3H); $^{13}$C NMR (126 MHz, CDCl$_3$) δ 153.5, 138.1, 136.9, 124.2, 121.9, 115.2, 70.8, 58.2, 44.5, 44.4, 34.8, 24.0, 21.1, 19.5; IR (NaCl, thin film, cm$^{-1}$) 3305, 2963, 2921, 2873, 1618, 1575, 1456, 1297, 1138, 1077, 1030, 841; HRMS (ESI-TOF) m/z calcd for C$_{14}$H$_{20}$NO$^+$ (M+H)$^+$ 218.1539, found 218.1534.

Example 12

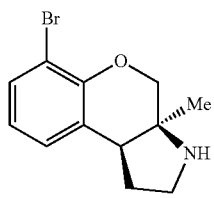

MRP4270

MRP4270: General procedure 8 was used and the product was isolated in 55% yield as a clear oil: $^1$H NMR (500 MHz, CDCl$_3$) δ 7.37 (dd, J=7.9, 1.6 Hz, 1H), 7.09 (dd, J=7.7, 2.2 Hz, 1H), 6.80 (t, J=7.8 Hz, 1H), 3.87 (d, J=11.2 Hz, 1H), 3.84 (d, J=10.9 Hz, 1H), 3.13 (dt, J=10.6, 7.8 Hz, 1H), 3.02 (ddd, J=10.6, 8.0, 4.4 Hz, 1H), 2.92 (t, J=8.1 Hz, 1H), 2.51 (dtd, J=12.4, 7.8, 4.3 Hz, 1H), 2.37 (br s, 1H), 1.86 (dq, J=12.8, 8.0 Hz, 1H), 1.28 (s, 3H); $^{13}$C NMR (126 MHz, CDCl$_3$) δ 150.5, 131.1, 129.5, 127.8, 122.3, 111.2, 72.0, 58.2, 46.0, 44.6, 36.1, 24.2; IR (NaCl, thin film, cm$^{-1}$) 3334, 2963, 2926, 2875, 1563, 1465, 1441, 1229, 1071, 1019, 771, 732; HRMS (ESI-TOF) m/z calcd for C$_{12}$H$_{15}$BrNO$^+$ (M+H)$^+$ 268.0332, found 268.0338.

Example 13

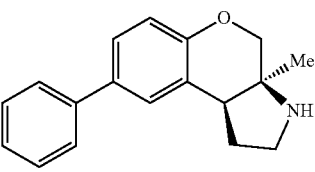

MRP5028

MRP5028: General procedure 8 was used and the product was isolated in 76% yield as a clear oil: $^1$H NMR (500 MHz, CDCl$_3$) δ 7.59-7.53 (m, 2H), 7.46-7.41 (m, 2H), 7.40-7.36 (m, 2H), 7.33 (tt, J=7.2, 1.4, 1.2 Hz, 1H), 6.98 (d, J=8.2 Hz, 1H), 3.85 (d, J=10.9 Hz, 1H), 3.80 (dd, J=10.7, 1.0 Hz, 1H), 3.15 (dt, J=10.7, 7.7 Hz, 1H), 3.05 (ddd, J=10.6, 8.0, 4.5 Hz, 1H), 2.98 (br t, J=7.9 Hz, 1H), 2.76 (br s, 1H), 2.55 (dtd, J=12.5, 7.8, 4.5 Hz, 1H), 1.95 (dq, J=13.0, 7.9 Hz, 1H), 1.31 (s, 3H); $^{13}$C NMR (126 MHz, CDCl$_3$) δ 153.4, 141.0, 134.6, 128.84, 128.81, 126.84, 126.83, 126.3, 126.2, 117.4, 71.5, 58.2, 45.7, 44.6, 36.0, 24.2; IR (NaCl, thin film, cm$^{-1}$) 3322, 3057, 3029, 2963, 2873, 1482, 1265, 1229, 1129, 1049, 1019, 826, 764, 732, 698; HRMS (ESI-TOF) m/z calcd for C$_{18}$H$_{20}$NO$^+$ (M+H)$^+$ 266.1539, found 266.1533.

Example 14

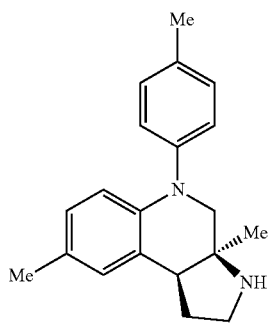

MRP5056

MRP5056: General procedure 8 was used and the product was isolated in 74% yield as a clear oil: $^1$H NMR (500 MHz, CDCl$_3$) δ 7.15 (d, J=8.3 Hz, 2H), 7.09 (d, J=8.3 Hz, 2H), 6.97 (d, J=2.1 Hz, 1H), 6.78 (dd, J=8.4, 2.1 Hz, 1H), 6.68 (d, J=8.4 Hz, 1H), 3.96 (br s, 1H), 3.45 (d, J=11.8 Hz, 1H), 3.30 (d, J=11.7 Hz, 1H), 3.13-3.09 (m, 2H), 2.98 (br t, J=8.1 Hz, 1H), 2.54 (dddd, J=13.0, 8.2, 6.4, 5.2 Hz, 1H), 2.35 (s, 3H), 2.26 (s, 3H), 1.90 (dq, J=12.8, 8.2 Hz, 1H), 1.31 (s, 3H); $^{13}$C NMR (126 MHz, CDCl$_3$) δ 145.0, 141.5, 133.3, 130.7, 130.2, 128.6, 127.4, 127.3, 123.0, 115.5, 60.9, 57.1, 47.7, 44.1, 37.0, 25.1, 21.0, 20.6; IR (NaCl, thin film, cm$^{-1}$) 3351, 2921, 1609, 1502, 1259, 810; HRMS (ESI-TOF) m/z calcd for C$_{20}$H$_{25}$N$_2$$^+$ (M+H)$^+$ 293.2012, found 293.2011.

Example 15

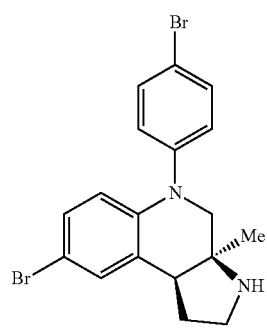

MRP5057

MRP5057: General procedure 8 was used and the product was isolated in 37% yield as a clear oil: $^1$H NMR (500 MHz, CDCl$_3$) δ 7.48-7.39 (m, 2H), 7.27 (d, J=2.0 Hz, 1H), 7.09-7.03 (m, 3H), 6.70 (d, J=8.8 Hz, 1H), 3.42 (d, J=11.9 Hz, 1H), 3.27 (d, J=11.9 Hz, 1H), 3.16-3.03 (m, 2H), 2.93 (br t, J=8.4 Hz, 1H), 2.61 (br s, 1H), 2.57-2.45 (m, 1H), 1.86 (dq, J=13.0, 8.4 Hz, 1H), 1.27 (s, 3H); $^{13}$C NMR (126 MHz, CDCl$_3$) δ 146.2, 141.9, 133.0, 132.8, 130.6, 129.6, 125.2, 117.6, 116.5, 112.0, 60.3, 57.2, 47.7, 44.3, 37.1, 25.4; IR (NaCl, thin film, cm$^{-1}$) 3320, 2961, 2922, 1583, 1438, 1258, 1167, 1068, 812; HRMS (ESI-TOF) m/z calcd for C$_{18}$H$_{19}$Br$_2$N$_2$$^+$ (M+H)$^+$ 420.9910, found 420.9899.

Example 16

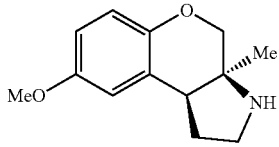
MRP5065

MRP5065: General procedure 8 was used and the product was isolated in 81% yield as a yellow oil: $^1$H NMR (400 MHz, CDCl$_3$) δ 6.78 (d, J=8.5 Hz, 1H), 6.70-6.63 (m, 2H), 3.74 (d, J=11.2 Hz, 1H), 3.74 (s, 3H), 3.66 (d, J=10.9 Hz, 1H), 3.12-3.03 (m, 1H), 3.01-2.95 (m, 1H), 2.94 (br s, 1H), 2.87 (t, J=7.7 Hz, 1H), 2.52-2.40 (m, 1H), 1.85 (dq, J=11.9, 7.6 Hz, 1H), 1.22 (s, 3H); $^{13}$C NMR (101 MHz, CDCl$_3$) δ 154.2, 147.8, 126.9, 117.6, 114.5, 113.2, 71.6, 58.4, 55.7, 45.8, 44.6, 35.9, 24.2; IR (NaCl, thin film, cm$^{-1}$) 3342, 2960, 2872, 2833, 1497, 1211, 1046, 817, 722; HRMS (ESI-TOF) m/z calcd for C$_{13}$H$_{18}$NO$_2^+$ (M+H)$^+$ 220.1332, found 220.1332.

Example 17

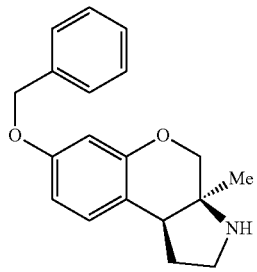
MRP5069

MRP5069: General procedure 8 was used and the product was isolated in 74% yield as a clear oil: $^1$H NMR (500 MHz, CDCl$_3$) δ 7.46-7.42 (m, 2H), 7.39 (t, J=7.5 Hz, 2H), 7.36-7.31 (m, 1H), 7.05 (d, J=8.5 Hz, 1H), 6.63 (dd, J=8.5, 2.6 Hz, 1H), 6.53 (d, J=2.6 Hz, 1H), 5.02 (s, 2H), 3.78 (d, J=10.9 Hz, 1H), 3.73 (d, J=10.9 Hz, 1H), 3.10 (dt, J=10.6, 7.6 Hz, 1H), 2.99 (ddd, J=10.6, 7.9, 4.6 Hz, 1H), 2.85 (t, J=7.7 Hz, 1H), 2.45 (ddd, J=15.8, 8.0, 3.8 Hz, 1H), 2.40 (br s, 1H), 1.84 (dq, J=12.8, 7.7 Hz, 1H), 1.25 (s, 3H); $^{13}$C NMR (126 MHz, CDCl$_3$) δ 158.2, 154.5, 137.1, 130.7, 128.7, 128.0, 127.6, 118.4, 109.3, 102.7, 71.5, 70.2, 58.1, 45.0, 44.6, 35.9, 24.2; IR (NaCl, thin film, cm$^{-1}$) 3374, 3063, 3031, 2963, 2872, 1618, 1582, 1503, 1454, 1379, 1266, 1161, 1127, 1105, 1037, 833, 735, 697; HRMS (ESI-TOF) m/z calcd for C$_{19}$H$_{22}$NO$_2^+$ (M+H)$^+$296.1645, found 296.1644.

Example 18

General Procedure 9: Pyrrolidine N-Acetylation

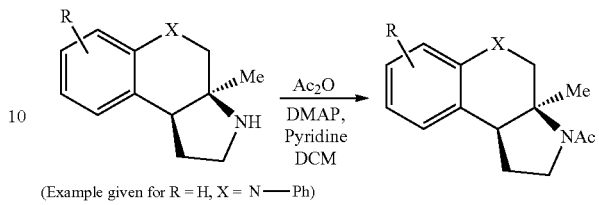

(Example given for R = H, X = N—Ph)

To a solution of amine MRP5017 (29 mg, 0.11 mmol) in DCM (0.8 mL) was sequentially added DMAP (1.0 mg, 8 μmol) and pyridine (10 μL, 0.12 mmol). The solution was cooled to 0° C. and Ac$_2$O (12 μL, 0.12 mmol) was added. The ice bath was then removed, and the solution was allowed to warm to rt. After 18 h, the solution was purified directly by column chromatography (0 to 70% gradient, i-PrOH in hexanes) afforded amide MRP5023 (25 mg, 0.08 mmol, 73%) as a clear oil.

Example 19

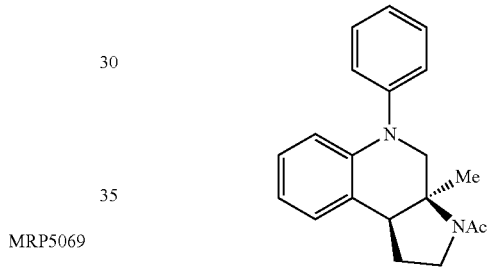
MRP5023

MRP5023: $^1$H NMR (500 MHz, CDCl$_3$) δ 7.32-7.28 (m, 2H), 7.18 (dd, J=7.7, 1.6 Hz, 1H), 7.17-7.14 (m, 2H), 7.05-7.02 (m, 1H), 7.02-6.99 (m, 1H), 6.92 (dd, J=8.4, 1.3 Hz, 1H), 6.84 (td, J=7.3, 1.3 Hz, 1H), 3.92 (d, J=12.2 Hz, 1H), 3.87 (d, J=12.2 Hz, 1H), 3.50-3.44 (m, 2H), 3.12 (t, J=7.4 Hz, 1H), 2.44 (dtd, J=12.2, 6.6, 5.3 Hz, 1H), 1.96-1.87 (m, 1H), 1.90 (s, 3H), 1.54 (s, 3H); $^{13}$C NMR (126 MHz, CDCl$_3$) δ 169.5, 147.4, 143.8, 130.0, 129.4, 126.9, 126.5, 123.1, 123.0, 119.8, 117.1, 62.6, 52.7, 48.6, 47.5, 33.1, 24.2, 22.8; IR (NaCl, thin film, cm$^{-1}$) 2967, 2929, 2869, 1644, 1496, 1408, 751; HRMS (ESI-TOF) m/z calcd for C$_{20}$H$_{22}$N$_2$ONa$^+$ (M+Na)$^+$329.1624, found 329.1628.

Example 20

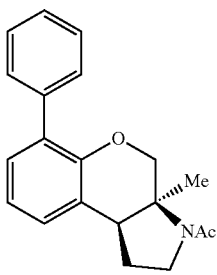
MRP5054

MRP5054: General procedure 9 was used and the product was isolated in 96% yield as a clear oil: $^1$H NMR (500 MHz, CDCl$_3$) δ 7.57-7.51 (m, 2H), 7.41 (dd, J=8.5, 6.9 Hz, 2H), 7.33 (tt, J=7.6, 1.4 Hz, 1H), 7.23 (dd, J=7.5, 1.7 Hz, 1H), 7.15 (dd, J=7.8, 1.7 Hz, 1H), 7.02 (t, J=7.5 Hz, 1H), 4.28 (d, J=10.8 Hz, 1H), 4.21 (d, J=10.7 Hz, 1H), 3.55 (dt, J=10.0, 7.1 Hz, 1H), 3.46 (ddd, J=10.0, 7.1, 5.3 Hz, 1H), 3.14 (t, J=7.2 Hz, 1H), 2.51-2.44 (m, 1H), 2.07 (s, 3H), 1.94 (dq, J=12.5, 7.5 Hz, 1H), 1.58 (s, 3H); $^{13}$C NMR (126 MHz, CDCl$_3$) δ 169.8, 151.9, 138.2, 130.6, 129.7, 129.2, 128.9, 128.2, 127.2, 124.5, 121.4, 67.9, 61.0, 47.8, 46.8, 32.5, 24.5, 21.4; IR (NaCl, thin film, cm$^{-1}$) 2968, 2929, 2873, 1645, 1429, 1409, 1216, 1029, 761, 698; HRMS (ESI-TOF) m/z calcd for C$_{20}$H$_{21}$NO$_2$Na$^+$ (M+Na)$^+$ 330.1465, found 330.1463.

Example 21

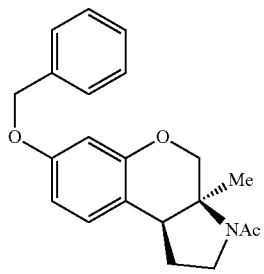

MRP5096

MRP5096: General procedure 9 was used and the product was isolated in 75% yield as a clear oil: $^1$H NMR (500 MHz, CDCl$_3$) δ 7.43 (d, J=7.0 Hz, 2H), 7.39 (t, J=7.4 Hz, 2H), 7.36-7.31 (m, 1H), 7.04 (d, J=8.4 Hz, 1H), 6.63 (dd, J=8.5, 2.6 Hz, 1H), 6.53 (d, J=2.6 Hz, 1H), 5.02 (s, 2H), 4.34 (d, J=10.8 Hz, 1H), 4.19 (d, J=10.8 Hz, 1H), 3.50 (dt, J=10.0, 6.8 Hz, 1H), 3.37 (dt, J=10.1, 6.6 Hz, 1H), 3.02 (t, J=6.7 Hz, 1H), 2.39 (dq, J=12.9, 6.5 Hz, 1H), 2.06 (s, 3H), 1.84 (dq, J=13.6, 6.9 Hz, 1H), 1.53 (s, 3H); $^{13}$C NMR (101 MHz, CDCl$_3$) δ 169.8, 158.6, 155.6, 137.1, 130.1, 128.8, 128.1, 127.7, 116.0, 109.7, 102.6, 70.2, 67.8, 61.0, 47.7, 45.8, 31.9, 24.5, 21.2; IR (NaCl, thin film, cm$^{-1}$) 2968, 2927, 2874, 1646, 1620, 1503, 1409, 1163, 738; HRMS (ESI-TOF) m/z calcd for C$_{21}$H$_{23}$NO$_3$Na$^+$ (M+Na)$^+$ 360.1570, found 360.1576.

Example 22

General Procedure 10: Pyrrolidine N-Methylation

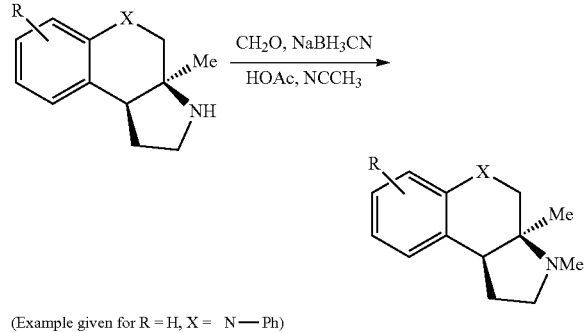

(Example given for R = H, X = N—Ph)

NaBH$_3$CN (9.1 mg, 0.15 mmol) was add to a solution of amine MRP5017 (29 mg, 0.11 mmol) and CH$_2$O (40 μL, 37% aq. solution) in acetonitrile (0.3 mL) at 0° C. After 15 min, glacial acetic acid (4 μL, 70 μmol) was added to the solution at 0° C. After an additional 15 min, the reaction was removed from the ice bath and allowed to warm to rt. After 18 h, the reaction mixture was directly purified by column chromatography (0 to 60% gradient, i-PrOH in 99:1 hexanes:NEt$_3$) afforded MRP5022 (27 mg, 0.10 mmol, 89%) as a clear oil.

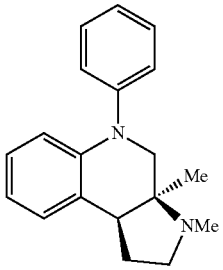

MRP5022

MRP5022: $^1$H NMR (500 MHz, CDCl$_3$) δ 7.38-7.32 (m, 2H), 7.25-7.21 (m, 2H), 7.16 (dd, J=7.7, 1.6 Hz, 1H), 7.09 (tt, J=7.3, 1.2 Hz, 1H), 6.96 (ddd, J=8.5, 7.1, 1.6 Hz, 1H), 6.83 (dd, J=8.4, 1.2 Hz, 1H), 6.79 (td, J=7.4, 1.2 Hz, 1H), 3.40 (d, J=11.6 Hz, 1H), 3.26 (dd, J=11.6, 1.2 Hz, 1H), 3.02-2.96 (m, 2H), 2.87 (td, J=9.1, 4.8 Hz, 1H), 2.49 (dddd, J=12.6, 9.4, 7.9, 4.7 Hz, 1H), 2.40 (s, 3H), 1.83 (dtd, J=12.7, 8.8, 6.5 Hz, 1H), 1.19 (s, 3H); $^{13}$C NMR (126 MHz, CDCl$_3$) δ 147.9, 143.1, 130.3, 129.5, 128.6, 126.4, 124.1, 123.5, 119.2, 115.5, 60.6, 52.8, 52.5, 48.0, 34.6, 32.9, 21.4; IR (NaCl, thin film, cm$^{-1}$) 3029, 2961, 2933, 2893, 2778, 1592, 1495, 1367, 1266, 1212, 747, 699; HRMS (ESI-TOF) m/z calcd for C$_{19}$H$_{23}$N$_2^+$ (M+H)$^+$ 279.1856, found 279.1867.

Example 23

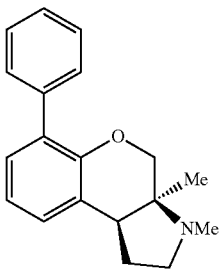

MRP5067

MRP5067: General procedure 10 was used and the product was isolated in 70% yield as a clear oil: $^1$H NMR (500 MHz, CDCl$_3$) δ 7.58-7.53 (m, 2H), 7.44-7.38 (m, 2H), 7.33 (tt, J=7.5, 1.4 Hz, 1H), 7.18 (dd, J=7.5, 1.8 Hz, 1H), 7.14 (dd, J=7.7, 1.7 Hz, 1H), 7.00 (t, J=7.5 Hz, 1H), 3.78 (s, 2H), 3.01 (t, J=8.7 Hz, 1H), 2.97-2.90 (m, 2H), 2.49 (ddt, J=12.5, 9.3, 5.9 Hz, 1H), 2.45 (s, 3H), 1.84 (dq, J=12.6, 7.9 Hz, 1H), 1.18 (s, 3H); $^{13}$C NMR (126 MHz, CDCl$_3$) δ 151.0, 138.6, 130.5, 129.7, 129.3, 128.6, 128.1, 128.0, 127.1, 121.3, 69.3, 59.3, 53.1, 46.3, 34.8, 32.6, 19.4; IR (NaCl, thin film, cm$^{-1}$) 3056, 2963, 2932, 2871, 1466, 1430, 1209, 1179, 1072, 1022, 759, 698; HRMS (ESI-TOF) m/z calcd for $C_{19}H_{22}NO^+$ (M+H)$^+$ 280.1696, found 280.1694.

Example 24

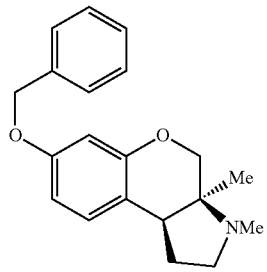

MRP5097

MRP5097: General procedure 10 was used and the product was isolated in 72% yield as a clear oil: $^1$H NMR (500 MHz, CDCl$_3$) δ 7.43 (d, J=7.2 Hz, 2H), 7.39 (t, J=7.4 Hz, 2H), 7.35-7.30 (m, 1H), 7.02 (d, J=8.5 Hz, 1H), 6.61 (dd, J=8.4, 2.6 Hz, 1H), 6.52 (d, J=2.5 Hz, 1H), 5.02 (s, 2H), 3.79 (d, J=11.0 Hz, 1H), 3.73 (d, J=10.9 Hz, 1H), 2.95-2.82 (m, 3H), 2.43 (s, 3H), 2.43-2.37 (m, 1H), 1.74 (dq, J=12.8, 7.6 Hz, 1H), 1.12 (s, 3H); $^{13}$C NMR (126 MHz, CDCl$_3$) δ 158.2, 154.5, 137.3, 130.4, 128.7, 128.1, 127.6, 119.7, 109.3, 102.9, 70.3, 69.0, 59.3, 53.1, 45.3, 34.7, 32.3, 18.7; IR (NaCl, thin film, cm$^{-1}$) 2962, 2931, 2783, 1618, 1583, 1503, 1454, 1266, 1163, 1036, 734, 696; HRMS (ESI-TOF) m/z calcd for $C_{20}H_{24}NO_2^+$ (M+H)$^+$ 310.1802, found 310.1804.

Example 25

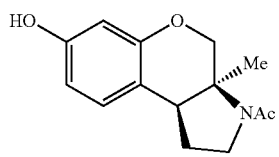

MRP5098

MRP5098: MRP5096 was used as the starting material. General procedure 7 was used and the product was isolated in 89% yield as a clear oil: $^1$H NMR (500 MHz, CD$_3$OD) δ 7.02 (d, J=8.4 Hz, 1H), 6.44 (dd, J=8.3, 2.5 Hz, 1H), 6.26 (d, J=2.5 Hz, 1H), 4.28 (d, J=10.8 Hz, 1H), 4.09 (d, J=10.7 Hz, 1H), 3.58 (dt, J=10.1, 6.8 Hz, 1H), 3.39 (dt, J=10.2, 6.7 Hz, 1H), 3.05 (t, J=6.6 Hz, 1H), 2.43 (dq, J=13.0, 6.6 Hz, 1H), 2.06 (s, 3H), 1.85 (dq, J=12.4, 6.9 Hz, 1H), 1.49 (s, 3H); $^{13}$C NMR (126 MHz, CD$_3$OD) δ 171.0, 156.7, 155.2, 129.8, 114.4, 109.3, 102.5, 66.8, 61.2, 47.3, 45.5, 31.3, 22.6, 19.7; IR (NaCl, thin film, cm$^{-1}$) 3417, 2917, 1616, 1505, 1455, 1417, 1160, 1113, 1043, 848, 630; HRMS (ESI-TOF) m/z calcd for $C_{14}H_{17}NO_3Na^+$ (M+Na)$^+$ 270.1101, found 270.1099.

Example 26

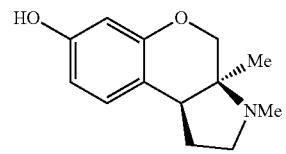

MRP5099

MRP5099: MRP5097 was used as the starting material. General procedure 7 was used and the product was isolated in 77% yield as a clear oil: $^1$H NMR (500 MHz, CD$_3$OD) δ 6.94 (d, J=8.2 Hz, 1H), 6.40 (dd, J=8.3, 2.5 Hz, 1H), 6.27 (d, J=2.5 Hz, 1H), 3.82 (d, J=11.0 Hz, 1H), 3.73 (dd, J=11.0, 1.0 Hz, 1H), 2.91-2.84 (m, 3H), 2.44 (ddt, J=12.8, 9.4, 6.4 Hz, 1H), 2.39 (s, 3H), 1.69 (dq, J=12.7, 7.7 Hz, 1H), 1.12 (s, 3H); $^{13}$C NMR (126 MHz, CD$_3$OD) δ 156.2, 154.1, 129.9, 117.8, 109.0, 102.7, 67.5, 59.4, 52.2, 44.7, 33.3, 31.6, 17.3; IR (NaCl, thin film, cm$^{-1}$) 3402, 2963, 1620, 1594, 1507, 1469, 1244, 1156, 1122, 1038, 842; HRMS (ESI-TOF) m/z calcd for $C_{13}H_{18}NO_2^+$ (M+H)$^+$ 220.1332, found 220.1328.

Example 27

Results from Psychoactive Drug Screening Program

Figure 14:
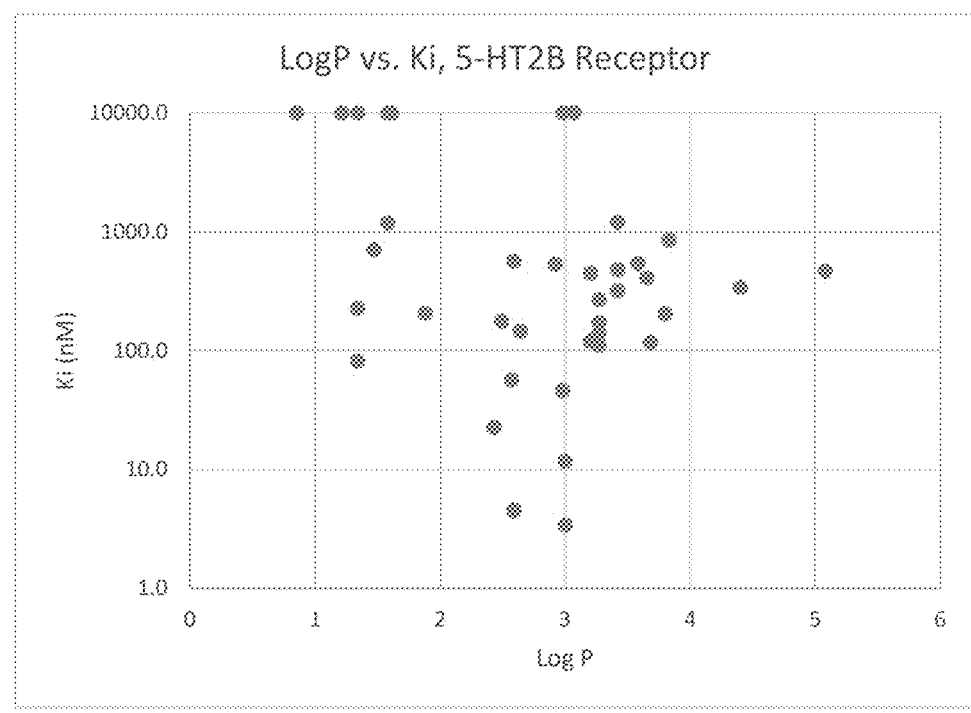
FIGS. 14-15 are graphical views of Log P vs. K$_i$, 5-HT$_2$B receptor and Log P vs. K$_i$, sigma-1 receptor, respectively, summarizing the data presented in Table 6, according to one or more embodiments of the present disclosure.
Figure 15:
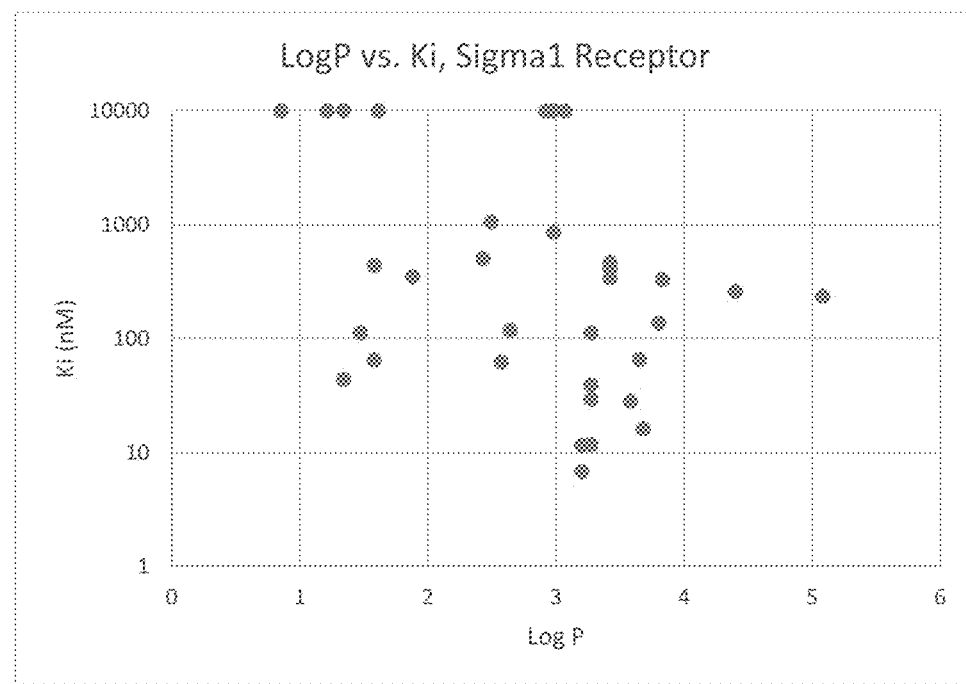
Figure 17:
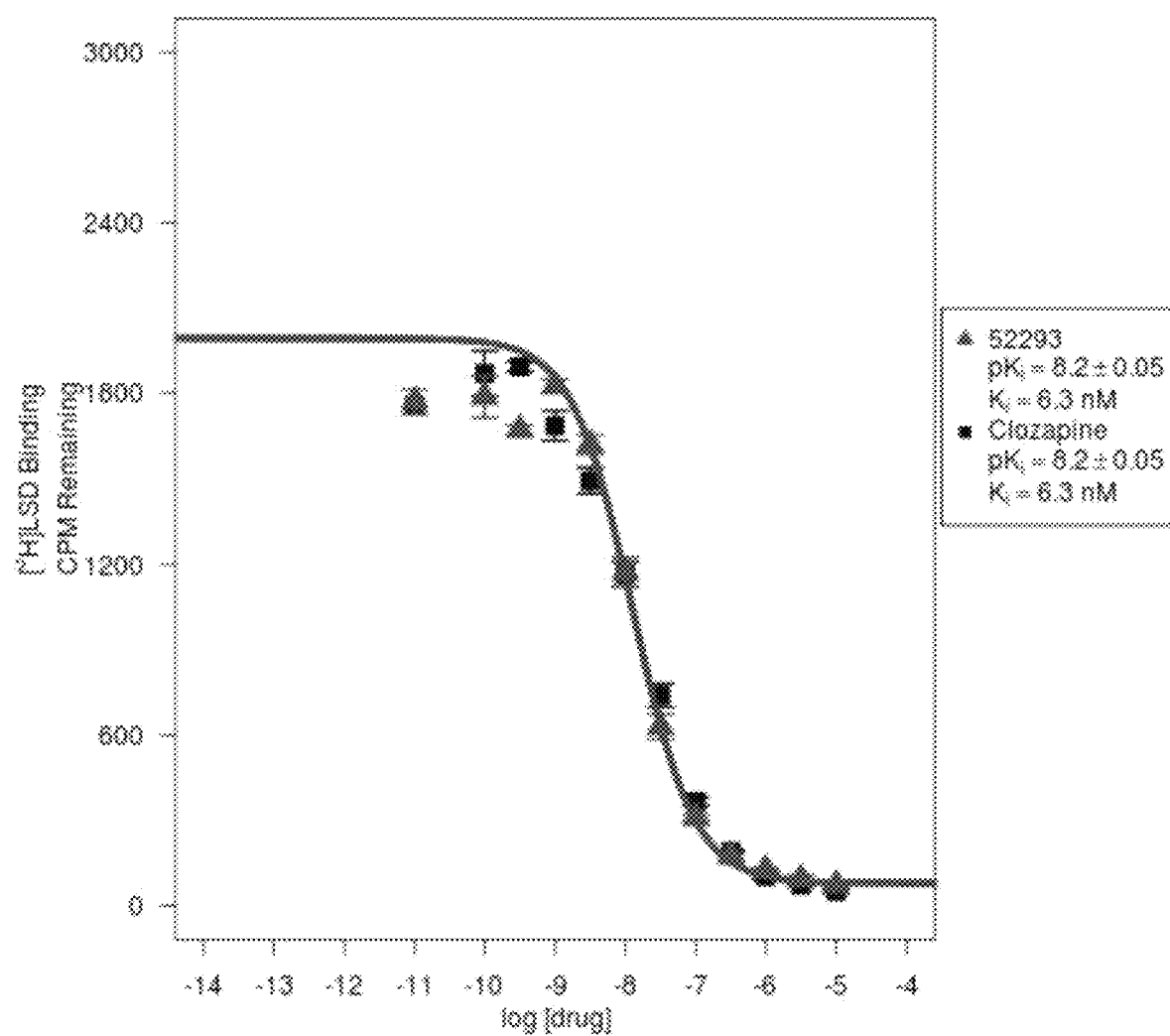
FIG. 17 is a graphical view of a competition binding curve for compound 52293 and clozapine as a reference compound, according to one or more embodiments of the present disclosure.
Figure 18:
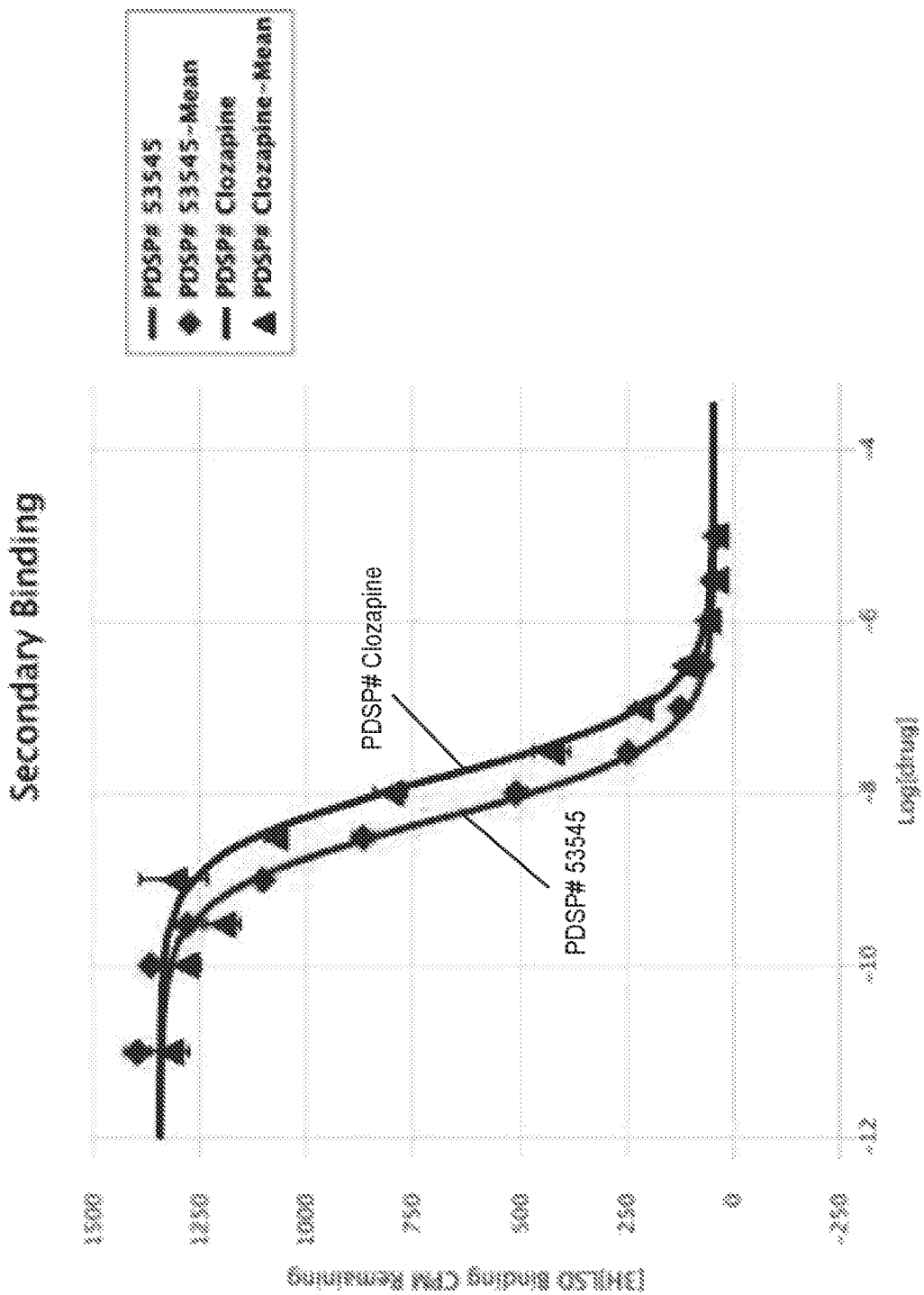
FIG. 18 is a graphical view of a competition binding curve for compound 53545 and clozapine as a reference compound, according to one or more embodiments of the present disclosure.
Figure 20:
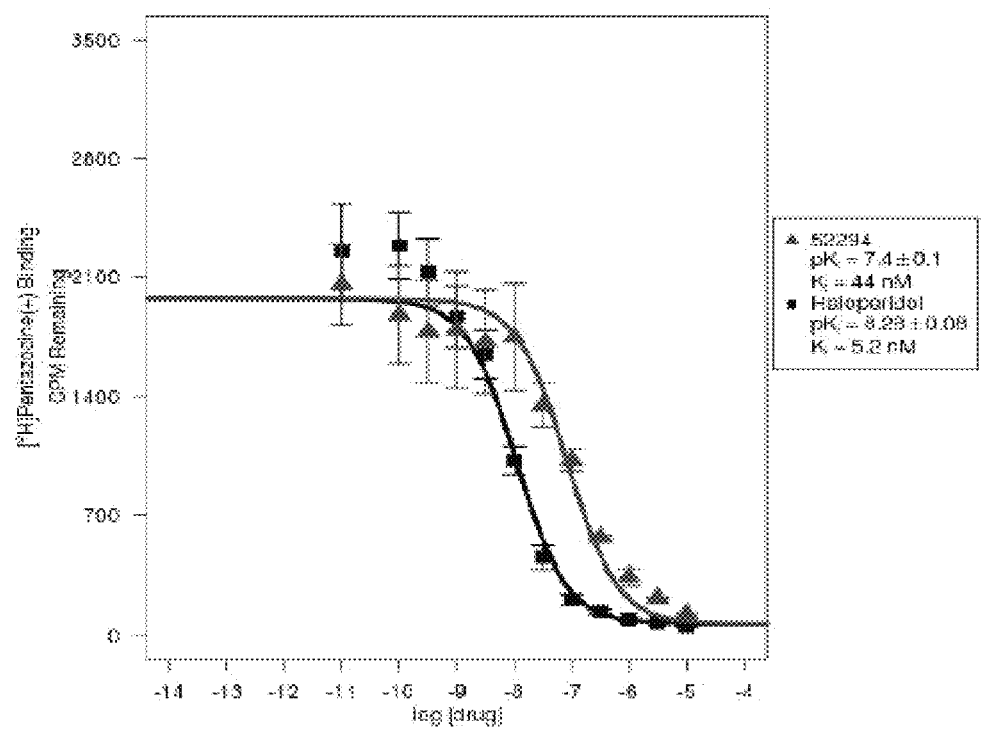
FIG. 20 is a graphical view of a competition binding curve for compound 52294 and haloperidol as a reference compound, according to one or more embodiments of the present disclosure.

FIGS. 13A-13E presents Table 6 which summarizes the binding affinity of various compounds against 5-HT$_{1A}$, 5-HT$_{2B}$, 5-HT$_7$, sigma-1, and sigma-2 GPCR receptors, according to one or more embodiments of the present disclosure. In particular, the $K_i$ (nM) value is provided. The structures for each of the compounds referred to in this paragraph can be determined with reference to FIGS. 13A-13E. FIGS. 14-15 are graphical views of Log P vs. $K_i$, 5-HT$_{2B}$ receptor and Log P vs. $K_i$, sigma-1 receptor, respectively, summarizing the data presented in Table 6, according to one or more embodiments of the present disclosure. Assay data for compound 52293 against 5-HT$_{7A}$ receptor, among others, is presented in FIGS. 16 (Table 7) and 17. Assay data for compound 53545 against 5-HT$_{7A}$ receptor is presented in FIG. 18 and Tables 8-9 provided below:

TABLE 8

| PDSP# | $K_i$ (nM) |
| --- | --- |
| 53545 | 2.39 |
| Clozapine | 7.23 |

TABLE 9

| Target | $K_i$ (nM) |
| --- | --- |
| 5-HT$_{1A}$ | 183 |
| 5-HT$_{1A}$ | 203 |
| 5-HT$_{1A}$ | 2.4 |
| Sigma-1 | 136 |
| Sigma-2 | 150 |
| >50 fold selective | |

Figure 21:
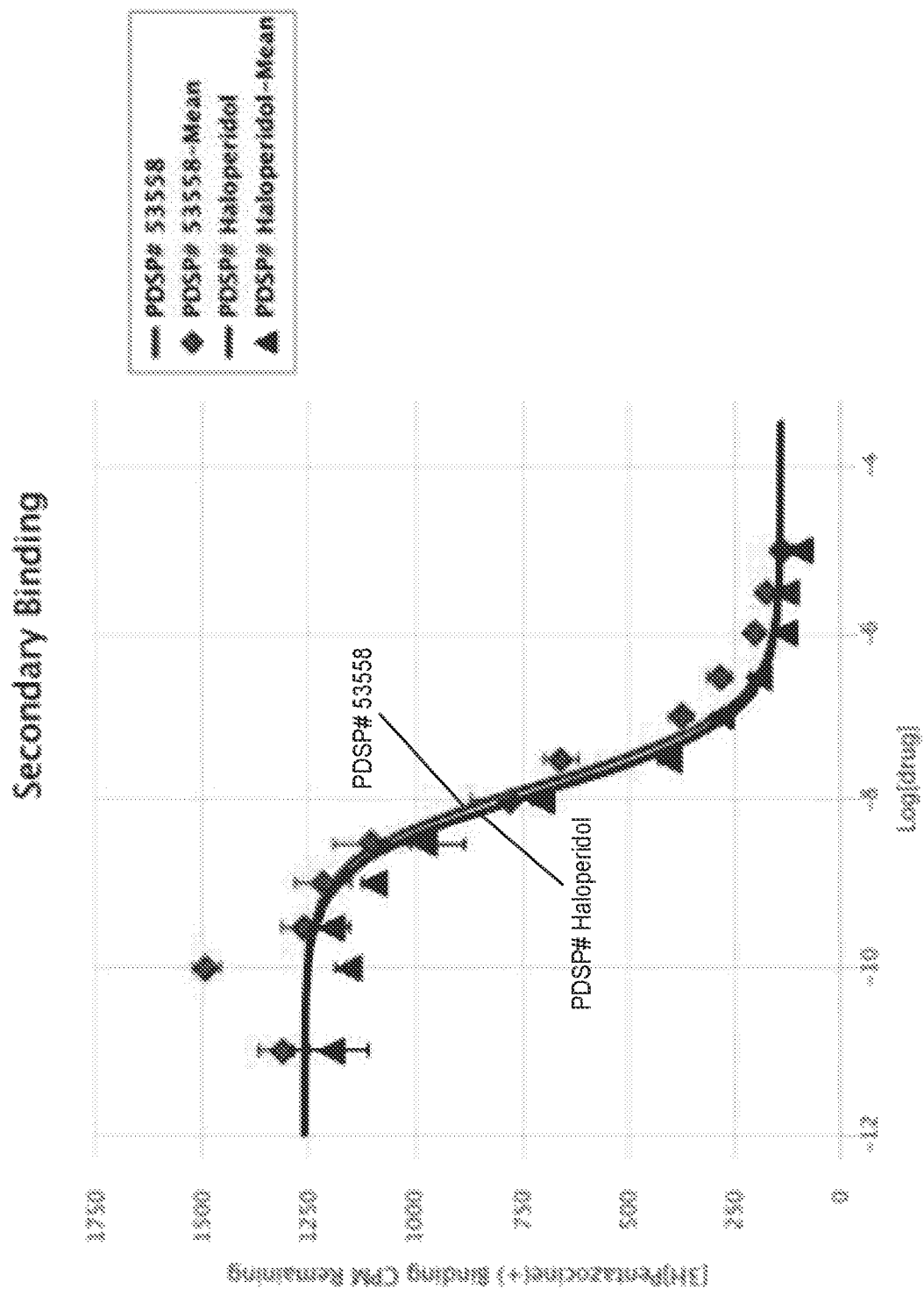
FIG. 21 is a graphical view of a competition binding curve for compound 53558 and haloperidol as a reference compound, according to one or more embodiments of the present disclosure.

Assay data for compound 52294 against sigma-1 receptor is presented in FIGS. 19 (Table 10) to 20. Assay data for compound 53558 against sigma-1 receptor is presented in FIG. 21 and Tables 10 and 11 below:

TABLE 10

| PDSP# | $K_i$ (nM) |
|---|---|
| 53558 | 6.51 |
| Haloperidol | 5.07 |

TABLE 11

| Target | $K_i$ (nM) |
|---|---|
| 5-HT$_{1A}$ | n/a |
| 5-HT$_{1A}$ | 448 |
| 5-HT$_{1A}$ | n/a |
| Sigma-1 | 6.8 |
| Sigma-2 | 125 |
| about 18 fold selective | |

Figure 22:
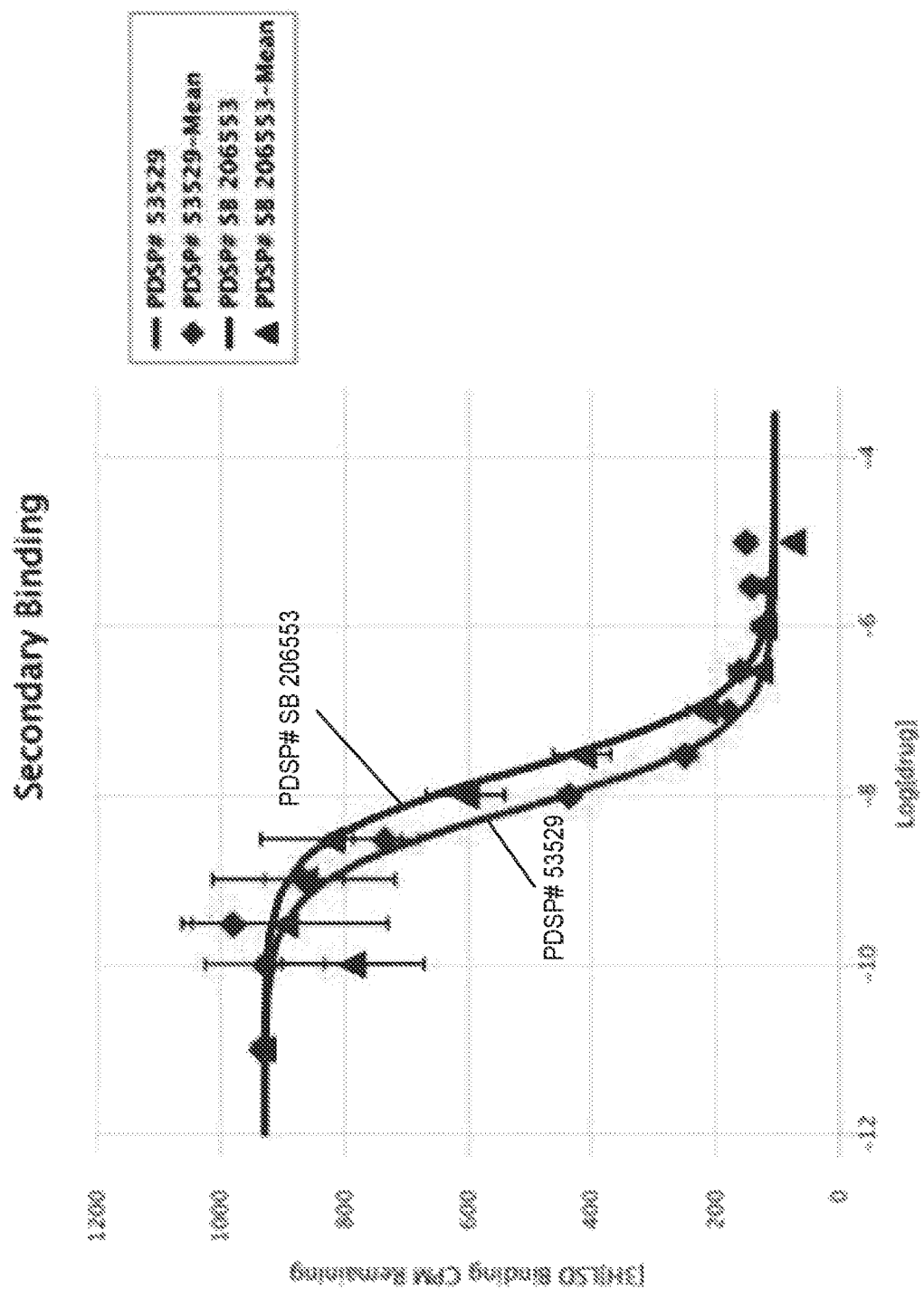
FIG. 22 is a graphical view of a competition binding curve for compound 53529 and SB 206553 as a reference compound, according to one or more embodiments of the present disclosure.

Assay data for compound 53529 against 5-HT$_{2B}$ receptor is presented in FIG. 22 and Tables 12-13 provided below:

TABLE 12

| PDSP# | $K_i$ (nM) |
|---|---|
| 53529 | 3.41 |
| SB 206553 | 9.79 |

TABLE 13

| Target | $K_i$ (nM) |
|---|---|
| 5-HT$_{1A}$ | 2200 |
| 5-HT$_{1A}$ | 3.4 |
| 5-HT$_{1A}$ | 960 |
| Sigma-1 | 3900 |
| Sigma-2 | 510 |
| about 150 fold selective | |

FIG. 23 presents Table 14 summarizing assay data for the compounds identified therein.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A compound of formula (I) or (II):

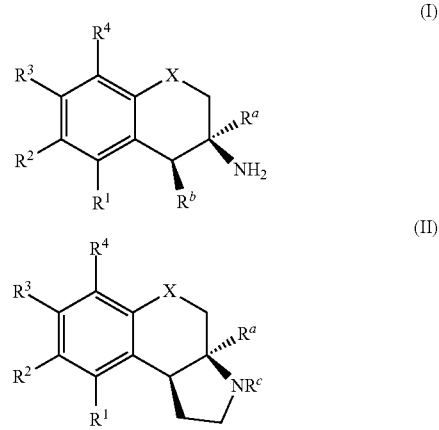

or a stereoisomer, tautomer, or pharmaceutically acceptable salt thereof, wherein:

X is selected from the group consisting of —O—, and —N(R')—, wherein R', if present, is selected from hydrogen, substituted or unsubstituted aryl group, and substituted or unsubstituted aryl sulfonyl group;

$R^a$ and $R^b$ are each independently selected from substituted or unsubstituted alkyl, substituted or unsubstituted alkenyl, and substituted or unsubstituted aralkyl;

$R^c$ is selected from hydrogen, substituted or unsubstituted alkyl, and substituted or unsubstituted aryl; and $R^1$, $R^2$, $R^3$, and $R^4$ are each, if present, independently selected from hydrogen, hydroxyl, halide, substituted or unsubstituted alkoxy, substituted or unsubstituted aralkoxy, substituted or unsubstituted alkyl, substituted or unsubstituted aryl, substituted or unsubstituted aryloxy, substituted or unsubstituted alkenyl, substituted or unsubstituted alkynyl, substituted or unsubstituted aralkyl, and substituted or unsubstituted alkaryl, or one of $R^1$ and $R^2$, $R^2$ and $R^3$, and $R^3$ and $R^4$ bind with each other to form an aromatic or non-aromatic 6-membered carbocyclic ring.

2. The compound of claim 1, wherein R' is selected from:

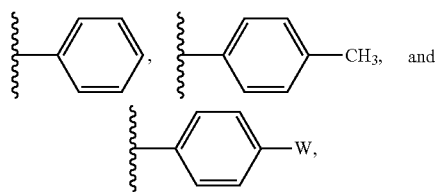

wherein W is a halogen.

3. The compound of claim 1, wherein $R^a$ is selected from —$CH_3$ and —$CH_2CH_2$-Ph.

4. The compound of claim 1, wherein $R^b$ is —$CH_2CH_3$ or —$CH=CH_2$.

5. The compound of claim 1, wherein $R^a$ is —$CH_3$ and $R^b$ is —$CH_2CH_3$.

6. The compound of claim 1, wherein $R^c$ is selected from —H, —$CH_3$, and -Ac.

7. The compound of claim 1, wherein $R^a$ is —$CH_3$ and $R^c$ is selected from —H, —$CH_3$, and -Ac.

8. The compound of claim 1, wherein $R^1$, $R^2$, $R^3$, and $R^4$ are each independently selected from —H, —OH, —$CH_3$, —Br, —Cl, —I, -Ph, —$OCH_3$, and —OBn.

9. The compound of claim 1, wherein the compound is selected from:

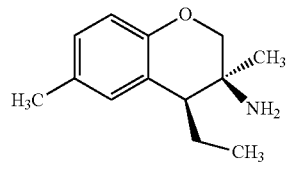
(I-2a)

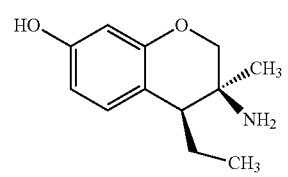
(I-2b)

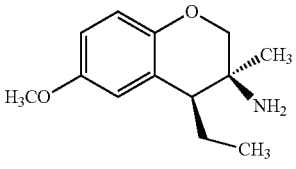
(I-2c)

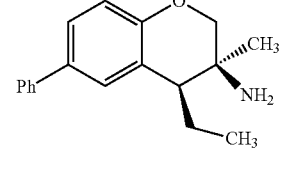
(I-2d)

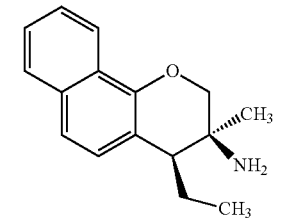
(I-2e)

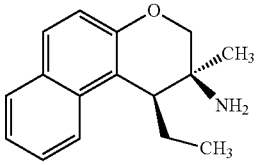
(I-2f)

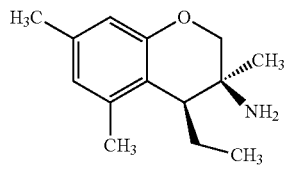
(I-2g)

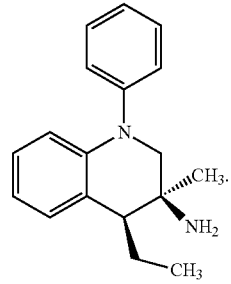
(I-3a)

10. The compound of claim 1, wherein the compound is selected from:

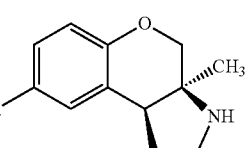
(II-2a)

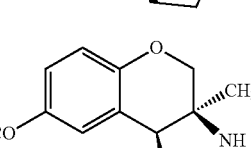
(II-2b)

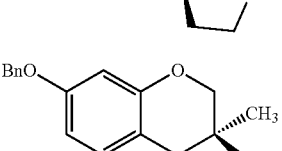
(II-2c)

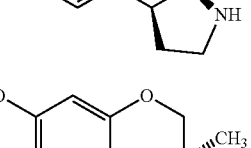
(II-2d)

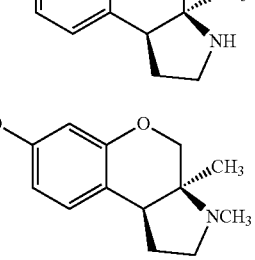
(II-2e)

(II-2f)
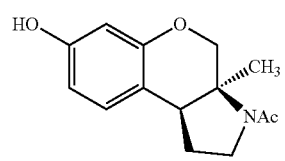
(II-2g)
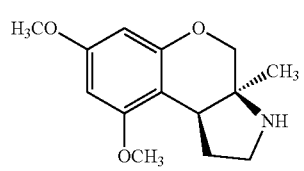
(II-2h)
(II-2i)
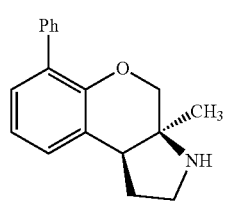
(II-2j)
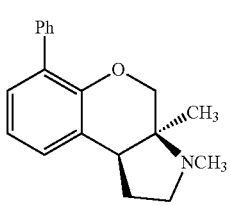
(II-2k)
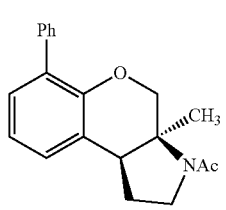
(II-2l)
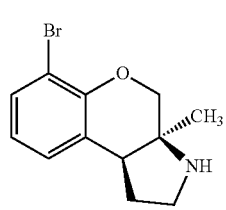
(II-2m)
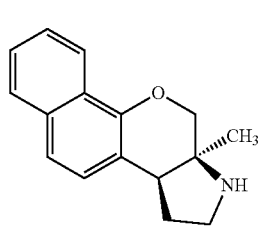
(II-2n)
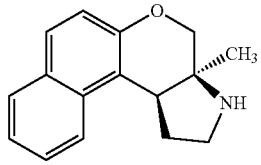
(II-2o)
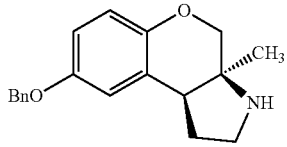
(II-2p)
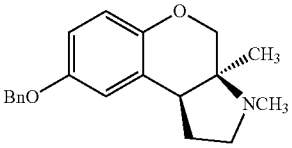
(II-2q)
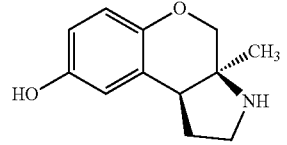
(II-2r)
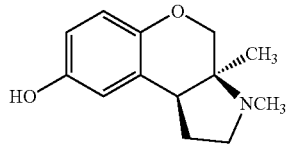
(II-2s)
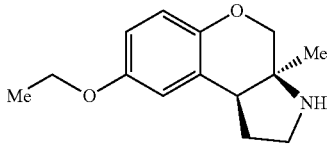
(II-2t)
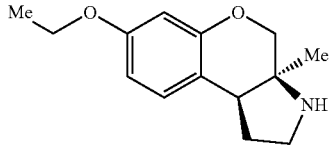
(II-2u)
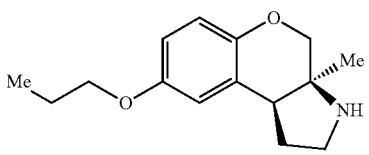
(II-2v)
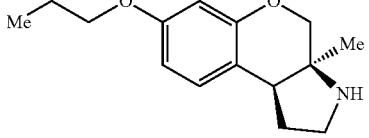
(II-2w)
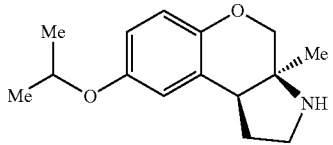

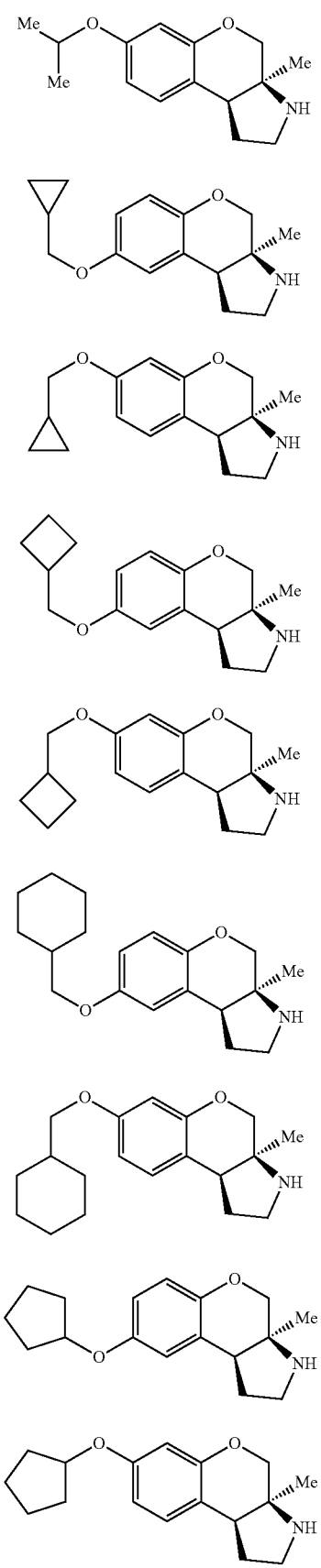
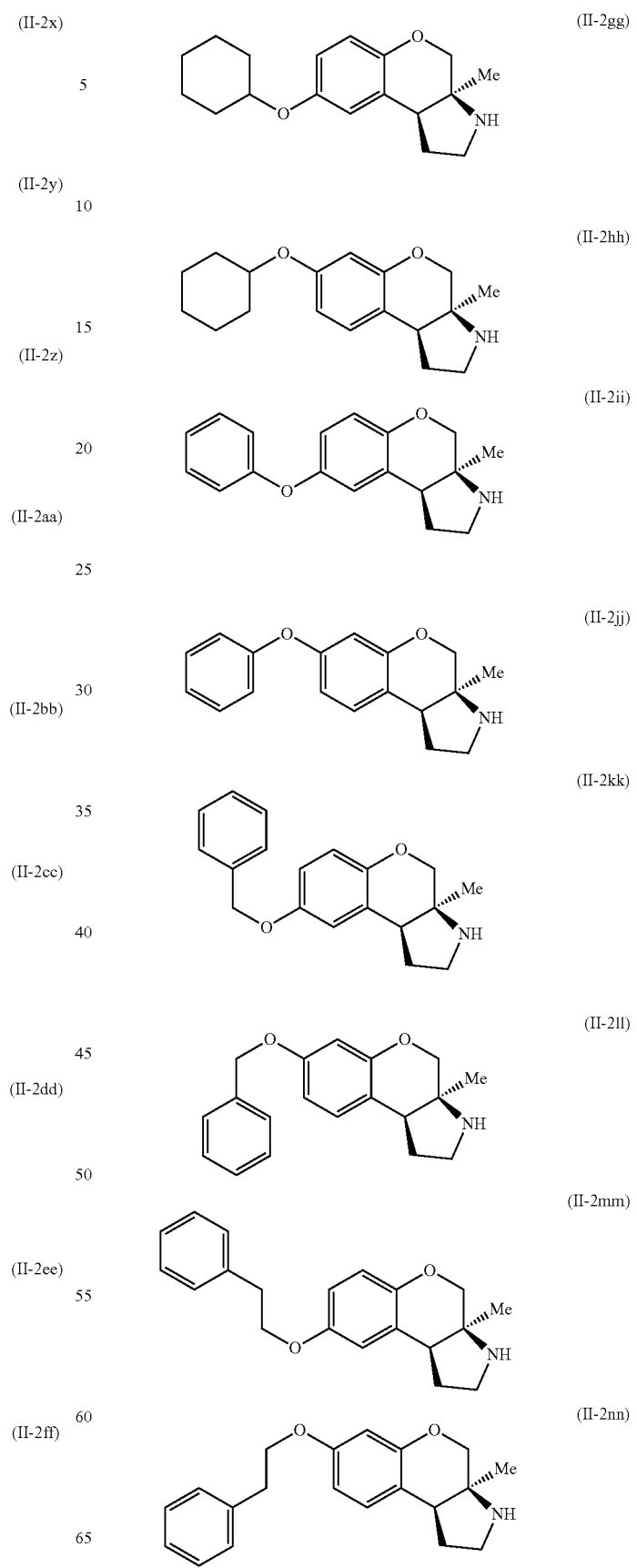

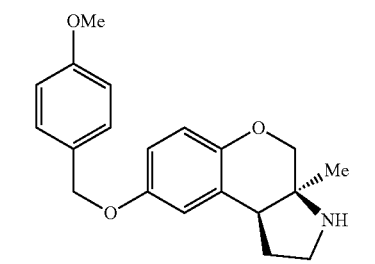
(II-2oo)
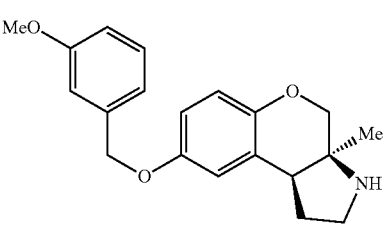
(II-2pp)
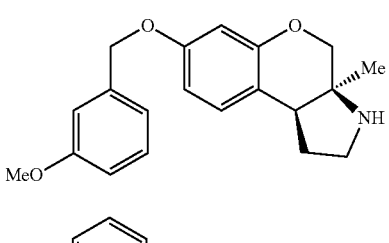
(II-2qq)
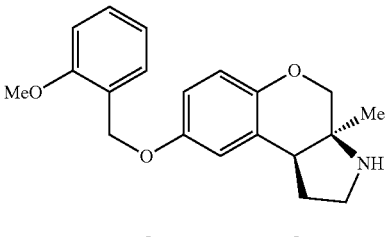
(II-2rr)
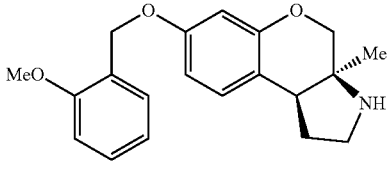
(II-2ss)
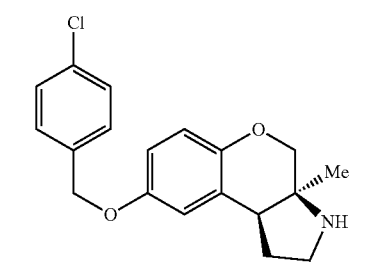
(II-2tt)
(II-2uu)
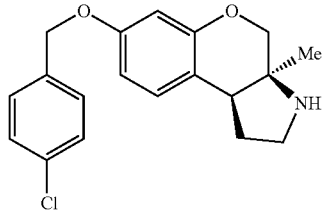
(II-2vv)
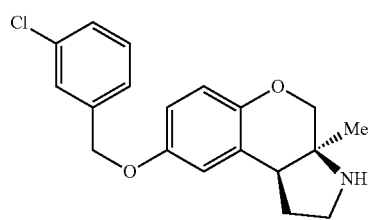
(II-2ww)
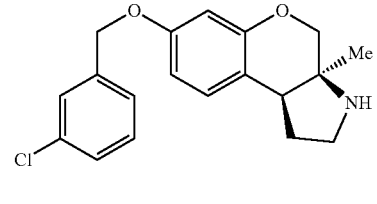
(II-2xx)
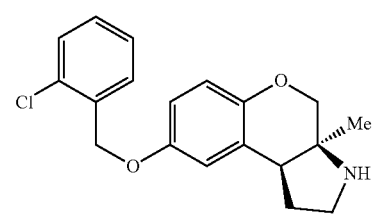
(II-2yy)
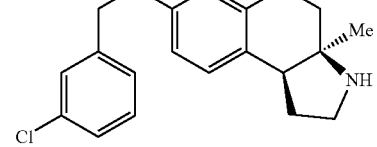
(II-2zz)
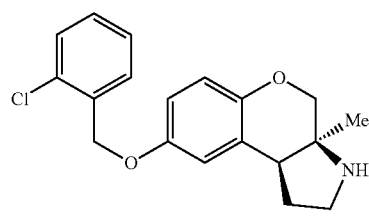
(II-2aaa)
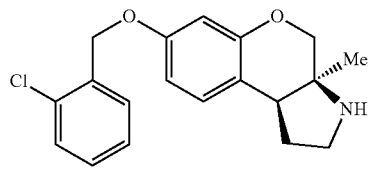
(II-2bbb)

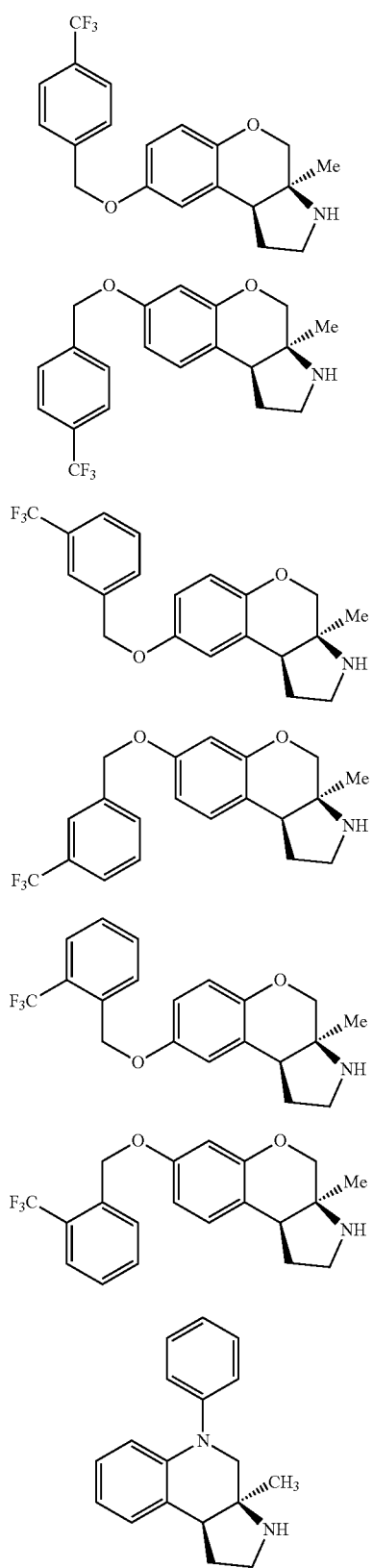
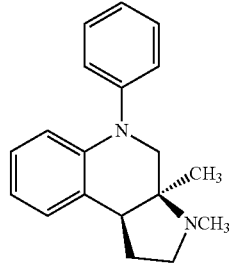
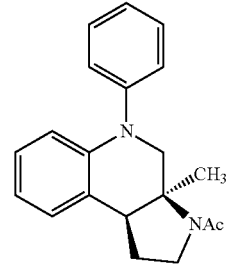
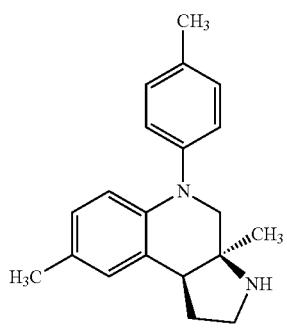
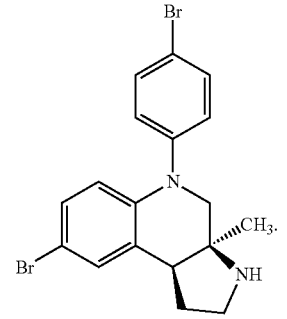
11. A pharmaceutical composition comprising a therapeutically effective amount of the compound of claim 1, or a pharmaceutically acceptable salt thereof, in combination with one or more pharmaceutically acceptable carriers.
* * * * *